(12) United States Patent
Funane et al.

(10) Patent No.: US 9,198,624 B2
(45) Date of Patent: Dec. 1, 2015

(54) BIOLOGICAL PHOTOMETRIC DEVICE AND BIOLOGICAL PHOTOMETRY METHOD USING SAME

(75) Inventors: Tsukasa Funane, Fujimi (JP); Hirokazu Atsumori, Kawagoe (JP); Takusige Katura, Fujimi (JP); Masashi Kiguchi, Kawagoe (JP); Tsuyoshi Takatera, Kashiwa (JP); Michiyuki Fujiwara, Kashiwa (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 3 days.

(21) Appl. No.: 13/806,790

(22) PCT Filed: Jul. 6, 2011

(86) PCT No.: PCT/JP2011/065505
§ 371 (c)(1),
(2), (4) Date: Dec. 24, 2012

(87) PCT Pub. No.: WO2012/005303
PCT Pub. Date: Jan. 12, 2012

(65) Prior Publication Data
US 2013/0102907 A1     Apr. 25, 2013

(30) Foreign Application Priority Data

Jul. 6, 2010  (JP) ................................. 2010-153801

(51) Int. Cl.
*A61B 6/00* (2006.01)
*A61B 5/00* (2006.01)
(Continued)

(52) U.S. Cl.
CPC ................ *A61B 6/00* (2013.01); *A61B 5/0075* (2013.01); *A61B 5/6814* (2013.01); *G01N 21/359* (2013.01); *G01N 21/49* (2013.01)

(58) Field of Classification Search
CPC ...... A61B 5/0075; A61B 5/6814; A61B 6/00; G01N 21/359; G01N 21/49
USPC .......... 600/310, 323, 324, 331, 473, 476, 477
See application file for complete search history.

(56) References Cited

U.S. PATENT DOCUMENTS 5,349,961 A    9/1994  Stoddart et al.
5,902,235 A    5/1999  Lewis et al.
(Continued)

FOREIGN PATENT DOCUMENTS

JP       9-19408      1/1997
JP    2001-178708     7/2001
(Continued)

OTHER PUBLICATIONS

Atsushi Maki et al., spatial and temporal analysis of human motor activity using noninvasive NIR topography, Medical Physics, Dec. 1995, vol. 22, No. 12.
(Continued)

*Primary Examiner* — Michael Rozanski
(74) *Attorney, Agent, or Firm* — Baker Botts L.L.P.

(57) ABSTRACT

The present invention is capable of separating/removing the influence of skin blood flow contained in near infrared spectroscopy (NIRS) signals and extracting a brain- or brain cortex-origin signal. Moreover, the present invention enables versatile separation of brain-origin and skin-origin signals in view of differences among individuals. A biological photometric device, wherein light transmitters and light receivers are located in such a manner that measurement can be conducted at a plurality of source-detector (SD) distances and light received by the individual light-receivers can pass through the gray matter to thereby separate a brain-origin signal and a skin-origin signal. Individual component analysis (ICA) is conducted on data obtained at the individual measurement points. Then, it is determined whether each individual component originates in the brain or in the skin with the use of the SD distance-dependency of the weighted value of each of the separated components.

17 Claims, 39 Drawing Sheets

(51) Int. Cl.
  *G01N 21/359* (2014.01)
  *G01N 21/49* (2006.01)

(56) References Cited

U.S. PATENT DOCUMENTS

| | | | |
|---|---|---|---|
| 7,072,701 | B2 | 7/2006 | Chen et al. |
| 2003/0088162 | A1 | 5/2003 | Yamamoto et al. |
| 2005/0148857 | A1 | 7/2005 | Maki et al. |
| 2009/0299160 | A1 | 12/2009 | Moridaira et al. |

FOREIGN PATENT DOCUMENTS

| | | |
|---|---|---|
| JP | 2002-527134 | 8/2002 |
| JP | 2005-245636 | 9/2005 |
| JP | 2006-280421 | 10/2006 |
| JP | 2007-44104 | 2/2007 |
| JP | 2007-044104 | 2/2007 |
| JP | 2007-111461 | 5/2007 |
| JP | 2008-064675 | 3/2008 |
| JP | 2008-64675 | 3/2008 |
| JP | 2009-148338 | 7/2009 |
| JP | 2009-148388 | 7/2009 |
| JP | 2010-104649 | 5/2010 |
| JP | 2010-240298 | 10/2010 |
| WO | WO 00/21435 A1 | 4/2000 |

OTHER PUBLICATIONS

Rolf B. Saager et al., Direct characterization and removal of interfering absorption trends in two-layer turbid media, J. Opt. Soc. Am., Sep. 2005, pp. 1874-1882, vol. 22, No. 9.

Quan Zhang et al., Adaptive filtering for global interference cancellation and real-time recovery of evoked brain activity: a Monte Carlo simulation study, Journal of Biomedical Optics, 044014, Jul./Aug. 2007, vol. 12(4).

Vladislav Toronov et al., Study of local cerebral hemodynamics by frequency-domain near-infrared spectroscopy and correlation with simultaneously acquired functional magnetic resonance imaging, Optics Express, Oct. 8, 2001, pp. 417-427, vol. 9, No. 8.

Satoru Kohno et al., Removal of the skin blood flow artifact in functional near-infrared spectroscopic imaging data through independent component analysis, Journal of Biomedical Optics, 062111, Nov./Dec. 2007, vol. 12(6).

Tsuyoshi Yamamoto et al, Arranging optical fibres for the spatial resolution improvement of topographical images, Physics in Medicine and Biology, 2002, pp. 3429-3440, vol. 47.

EPO Communication, Extended European Search Report and the EPO Search Opinion for EP Application No. 11803637.5, dated Mar. 3, 2014.

Office Action, mailed Jul. 7, 2015, which issued during the prosecution of Japanese Patent Application No. 2014-126138, which corresponds to the present application (with English translation attached).

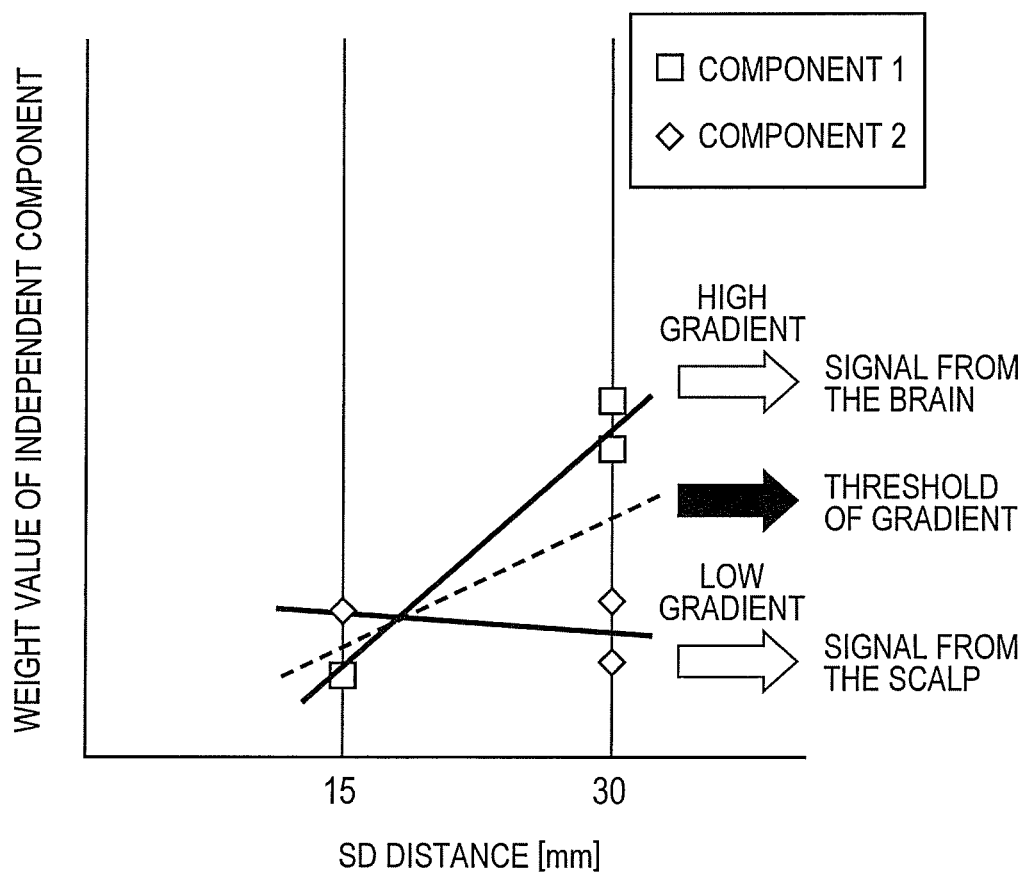

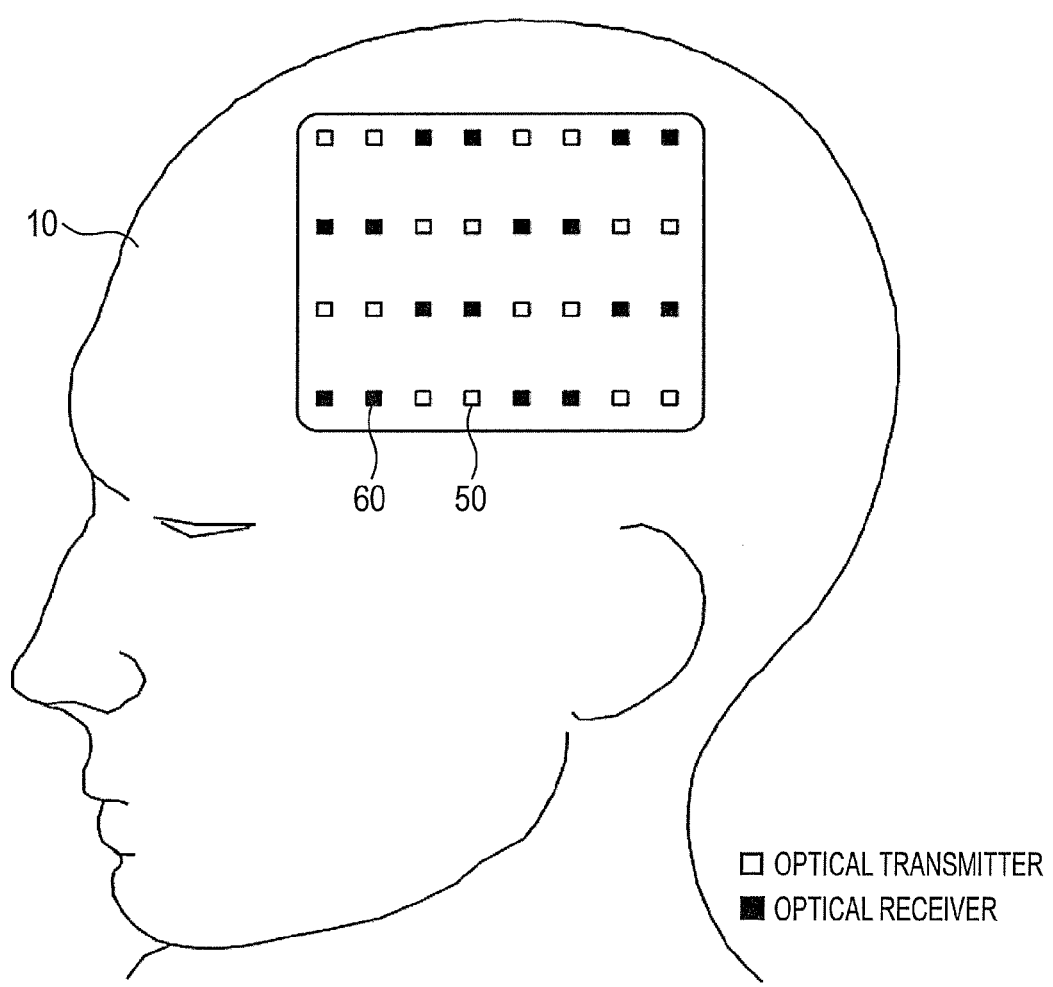

|     | AD1 | BD1 | AD2 | BD2 | AD3 | BD3 | AD4 | BD4 | AD5 | BD5 | AD6 | BD6 | AD7 | BD7 | AD8 | BD8 |
|-----|-----|-----|-----|-----|-----|-----|-----|-----|-----|-----|-----|-----|-----|-----|-----|-----|
| AS1 | ○ |   |   |   | ○ |   |   |   |   |   |   |   |   |   |   |   |
| BS1 | ◎ | ○ |   |   |   | ○ |   |   |   |   |   |   |   |   |   |   |
| AS2 | ○ | ◎ | ○ |   |   |   | ○ |   |   |   |   |   |   |   |   |   |
| BS2 |   | ○ | ◎ | ○ |   |   |   | ○ |   |   |   |   |   |   |   |   |
| AS3 | ○ |   |   |   | ○ | ◎ | ○ |   | ○ |   |   |   |   |   |   |   |
| BS3 |   | ○ |   |   |   | ○ | ◎ | ○ |   | ○ |   |   |   |   |   |   |
| AS4 |   |   | ○ |   |   |   | ○ | ◎ |   |   | ○ |   |   |   |   |   |
| BS4 |   |   |   | ○ |   |   |   | ○ |   |   |   | ○ |   |   |   |   |
| AS5 |   |   |   |   | ○ |   |   |   | ○ |   |   |   | ○ |   |   |   |
| BS5 |   |   |   |   |   | ○ |   |   | ◎ | ○ |   |   |   | ○ |   |   |
| AS6 |   |   |   |   |   |   | ○ |   | ○ | ◎ | ○ |   |   |   | ○ |   |
| BS6 |   |   |   |   |   |   |   | ○ |   | ○ | ◎ | ○ |   |   |   | ○ |
| AS7 |   |   |   |   |   |   |   | ○ |   |   |   |   | ○ | ◎ | ○ |   |
| BS7 |   |   |   |   |   |   |   |   | ○ |   |   |   |   | ○ | ◎ | ○ |
| AS8 |   |   |   |   |   |   |   |   |   |   | ○ |   |   |   | ○ | ◎ |
| BS8 |   |   |   |   |   |   |   |   |   |   |   | ○ |   |   |   | ○ |

○ : SD = 30 mm
◎ : SD = 15 mm
BLANK : UNUSED

FIG. 20

| SELECT PROBE ARRANGEMENT ▼ |
|---|
| 4 × 8 |
| 3 × 10 |
| OTHER |

SD DISTANCE SETTING
- ⦿ MANUAL SETTING
- ○ AUTO SETTING
- ○ AUTO SETTING (SD=30 mm ONLY)
- ○ SET USED SD DISTANCE 110    111

SD DISTANCE INPUT (UNIT: mm)

|     | AD1 | BD1 | AD2 | BD2 | AD3 | BD3 | AD4 | BD4 | AD5 | BD5 | AD6 | BD6 | AD7 | BD7 | AD8 | BD8 |
|-----|-----|-----|-----|-----|-----|-----|-----|-----|-----|-----|-----|-----|-----|-----|-----|-----|
| AS1 | 30  |     |     |     | 30  |     |     |     |     |     |     |     |     |     |     |     |
| BS1 | 15  | 30  |     |     |     | 30  |     |     |     |     |     |     |     |     |     |     |
| AS2 | 30  | 15  | 30  |     |     |     | 30  |     |     |     |     |     |     |     |     |     |
| BS2 |     | 30  | 15  | 30  |     |     |     | 30  |     |     |     |     |     |     |     |     |
| AS3 | 30  |     |     |     | 30  | 15  | 30  |     | 30  |     |     |     |     |     |     |     |
| BS3 |     | 30  |     |     |     | 30  | 15  | 30  |     | 30  |     |     |     |     |     |     |
| AS4 |     |     | 30  |     |     |     | 30  | 15  |     |     | 30  |     |     |     |     |     |
| BS4 |     |     |     | 30  |     |     |     | 30  |     |     |     | 30  |     |     |     |     |
| AS5 |     |     |     |     | 30  |     |     |     | 30  |     |     |     | 30  |     |     |     |
| BS5 |     |     |     |     |     | 30  |     |     | 15  | 30  |     |     |     | 30  |     |     |
| AS6 |     |     |     |     |     |     | 30  |     | 30  | 15  | 30  |     |     |     | 30  |     |
| BS6 |     |     |     |     |     |     |     | 30  |     | 30  | 15  | 30  |     |     |     | 30  |
| AS7 |     |     |     |     |     |     |     |     | 30  |     |     |     | 30  | 15  | 30  |     |
| BS7 |     |     |     |     |     |     |     |     |     | 30  |     |     |     | 30  | 15  | 30  |
| AS8 |     |     |     |     |     |     |     |     |     |     | 30  |     |     |     | 30  | 15  |
| BS8 |     |     |     |     |     |     |     |     |     |     |     | 30  |     |     |     | 30  |

112                                                 113      114

[ OK ]   CANCEL

BIOLOGICAL PHOTOMETRIC DEVICE AND BIOLOGICAL PHOTOMETRY METHOD USING SAME

TECHNICAL FIELD

The present invention relates to a technology that separates and removes influence of a surface component such as a scalp blood flow component to be mixed in a signal component in a biological photometric device using visible light or near-infrared light.

BACKGROUND ART

A brain function measuring device that uses a near-infrared spectroscopy (NIRS) may be used as medical and laboratory instruments or used for verification of educational effect or a rehabilitation effect, health management in homes, and market research such as product monitoring. Further, the near-infrared spectroscopy may also be used for a tissue oxygen saturation measurement or muscle oxygen metabolism measurement by using the same method. Further, the near-infrared spectroscopy may also be used not only for the measurement of sugar content of a fruit but also for a general absorption spectroscopic device.

The brain function measuring device using the near-infrared spectroscopy according to a related art includes an optical topographic method that noninvasively forms an image of a local hemodynamic change near a surface layer of a human brain. The optical topographic method irradiates light having a wavelength which belongs to a visible range to an infrared range onto a subject, detects the light which passes into the subject using a light detector at a point separated by several centimeters, and measures an amount of change in a hemoglobin concentration "(or change in multiplication of a hemoglobin concentration and an optical path") to form a two dimensional image (for example, see Patent Literature 1 and Non-Patent Literature 1). The optical topographic method is less restrictive for the subject than a brain function measuring technology such as a nuclear magnetic resonance imaging (MRI) or a positron emission tomography (PET). In a clinical site, a verbal function or a visual function is measured.

In a photo detecting signal or a biological signal (hereinafter, referred to as an NIRS signal) obtained by a noninvasive optical brain function imaging using the NIRS including an optical topographic method, there is a report saying that since the light is irradiated from a scalp, a scalp blood flow change in the scalp may affect the photo detecting signal or the biological signal. A method that extracts and removes such a component has been studied in consideration of the influence of the scalp blood flow. Most of them obtain a signal component from portions having different depths by a method of a distance between a plurality of irradiators-detectors (optical transmitter-optical receiver) (hereinafter, referred to as SD (source detector) distance) and remove a scalp blood flow signal which may be considered to influence measurement data of shallow layers using the signal component. Hereinafter, a measurement method at a plurality of SD distances is referred to as a multiple SD distance method.

For example, there is a method that determines an absorption coefficient in a scalp and a brain (gray matter) by a simultaneous equation using an optical path length in the scalp and the brain (gray matter) in a short SD distance and a long SD distance (for example, see Non-Patent Literature 2). In the method, a head structure is assumed as a two layered structure and it is required to assume a partial mean optical path length of each of layers. However, it is difficult to estimate an optical path length of a subject.

Further, a subtraction method that uses an adaptive filtering is suggested. In the method, a value obtained by multiplying an appropriate coefficient by measurement data in the short SD distance (hereinafter, referred to as short SD distance data) is subtracted from measurement data in a long SD distance (hereinafter, referred to as long SD distance data) to remove a scalp blood flow signal (for example, see Non-Patent Literature 3). In addition, as a subtraction method that uses linear regression, a method that obtains a brain activity signal by subtracting a fitting signal that is obtained by linearly regressing the short SD distance data to the long SD distance data from the long SD distance data is suggested (for example, see Non-Patent Literature 4).

Following methods are disclosed as a technology related thereto.

In Patent Literature 2, in order to provide a photometric device that is capable of removing unnecessary information by scalp blood flow using an optical transceiver including a plurality of optical transmitting probes and a plurality of optical receiving probes, a method that disposes a pair of a plurality of irradiators and detectors at the same center point, performs measurement, and removes unnecessary information by an arithmetic processing is disclosed. Further, in Patent Literature 3, with a device configuration that uses two detectors for one light source, a method that appropriately distinguish information obtained from two detectors to obtain a result that mainly characterizes a state in a brain tissue without being influenced by an overlapped adjacent tissue is disclosed. In addition, in Patent Literatures 4, 5, and 6, a method that calculates change in absorbance and performs operation such as subtraction with the long SD distance data and the short SD distance data is disclosed. However, these methods have the following problems.

First, in the operation such as subtraction between measurement data in each of the SD distances, it is difficult to determine various coefficients. In such an operation, since the various coefficients may influence the result, it is required to set an appropriate value. Further, when the short SD distance data is obtained, since the SD distance is often set to be 10 mm or less and a signal component which depends on the change in the absorption only on the scalp but not the brain blood flow is obtained, an amplitude ratio of brain•scalp components is unknown. Therefore, it is difficult to determine an appropriate coefficient by the operation. In order to appropriately correct long SD distance measurement data including scalp contribution and brain contribution, there is a need to know a contribution ratio and an optical path length ratio of each of the scalp and the brain.

Further, when the short SD distance data is fitted to the long SD distance data, if the scalp blood flow signal and the brain blood flow signal are not independent from each other, that is, if the scalp blood flow signal is correlated with the brain blood flow signal, the brain blood flow signal may be undesirably removed from the long SD distance data.

As a method that does not use a multiple SD-distance method, a method that extracts the brain activity using a signal separating method is studied. For example, there is a study saying that a spatial homogeneity (broad spectrum) of independence components extracted using an independent component analysis (ICA) is indexed and if the homogeneity is high, simultaneously measured LDF signals show significantly high correlation (see Non-Patent Literature 5). In the study, without using information such as task time, the scalp blood flow is tried to be discriminated only using the independence and the spatial distribution of the NIRS signals. As related patents, in Patent Literature 7, a method that divides a signal into a plurality of independent components by the independent component analysis and removes unnecessary components using the broad spectrum thereof is disclosed. Further, in Patent Literature 8, a method that divides a signal into a plurality of independent components by the independent component analysis and removes the unnecessary components using a reference signal other than a brain function measurement signal is disclosed. The method is an analysis method based on an assumption that the scalp blood flow has a broad spectrum. If the assumption is not satisfied, the method cannot be applied. Therefore, in order to discriminate a signal from the brain and a signal from the scalp, robust and general analysis method and device configuration are required.

CITATION LIST

Patent Literature

Patent Literature 1: Japanese Patent Application Laid-Open Publication No. Hei9 (1997)-019408
Patent Literature 2: Japanese Patent Application Laid-Open Publication No. 2008-64675
Patent Literature 3: Japanese Unexamined Patent Application Publication No. 2002-527134
Patent Literature 4: U.S. Pat. No. 7,072,701 B2
Patent Literature 5: U.S. Pat. No. 5,349,961
Patent Literature 6: U.S. Pat. No. 5,902,235
Patent Literature 7: Japanese Patent Application Laid-Open Publication No. 2005-245636
Patent Literature 8: Japanese Patent Application Laid-Open Publication No. 2006-280421
Patent Literature 9: Japanese Patent Application Laid-Open Publication No. 2001-178708

Non-Patent Literatures

Non-Patent Literature 1: A. Maki et al., "Spatial and temporal analysis of human motor activity using noninvasive NIR topography," Medical Physics, Vol. 22, No. 12, p. 1997-2005 (1995)
Non-Patent Literature 2: R. B. Saager and A. J. Berger: Direct characterization and removal of interfering absorption trends in two-layer turbid media: J. Opt. Soc. Am. A Opt. Image. Sci. Vis. 22(9), p. 1874-1882 (2005)
Non-Patent Literature 3: Q. Zhang, E. N. Brown and G. E. Strangman: Adaptive filtering for global interference cancellation and real-time recovery of evoked brain activity: a Monte Carlo simulation study: J. Biomed. Opt. 12(4), 044014 (2007)
Non-Patent Literature 4: V. Toronov, et al.: Study of local cerebral hemodynamics by frequency-domain near-infrared spectroscopy and correlation with simultaneously acquired functional magnetic resonance imaging: Opt. Express 9(8), p. 417-427 (2001)
Non-Patent Literature 5: S. Kohno, et al., "Removal of the skin blood flow artifact in functional near-infrared spectroscopic imaging data through independent component analysis," J Biomed Opt 12(6), 062111 (2007)
Non-Patent Literature 6: T. Yamamoto et al., "Arranging optical fibres for the spatial resolution improvement of topographical images," Phys. Med. Biol., Vol. 47, p. 3429-3440 (2002)

SUMMARY OF INVENTION

Technical Problem

An object of the present invention is to remove influence of a tissue component other than a brain including a local scalp blood flow contained in near infrared spectroscopy (NIRS) signals, discriminate and extract only a signal from the brain or the cerebral cortex, and more generally discriminate and extract a brain component, a scalp component, and a component which is shared by the brain and the scalp. Further, another object of the invention is to discriminate the signal from the brain and the signal from the scalp in consideration of the personal difference of the contribution ratio of the signal from the brain and the signal from the scalp.

Solution to Problem

In order to address the above problems, in a biological photometric device according to the present invention, in order to discriminate the signal from the brain and the signal from the scalp, optical transmitters and optical receivers are disposed so as to achieve the measurement by a plurality of SD distances and propagate light which is received by the optical receivers in both a gray matter and the scalp. At the time of measurement, the measurement is performed by appropriately switching the power on/off or high/low power of a light source or on/off or high/low gain of the detector if necessary so that the signals from the plurality of light sources are not interrupted from each other at the time of detecting the signal and each of the optical receivers receives light with an appropriate intensity level. Further, at the time of analysis, a signal separating method such as independent component analysis (ICA) is performed using data at measurement points and it is determined whether the separated component is a signal component from the brain or a scalp signal component using an SD distance dependency of a weight value at each of the measurement points of one or a plurality of obtained separated components. In addition, only using one or the plurality of separated components, a measurement signal in each of the SD distances is reconstructed.

Configurations of the present invention will be described below.

A biological photometric device includes one or a plurality of light irradiating units that irradiates light on a subject; one or a plurality of light detecting units that detects the light, which is irradiated on an irradiation point on the subject from the one or plurality of light irradiating units and propagated in the subject, at a detection point on the subject; a controller that controls the one or plurality of light irradiating units and the one or plurality of light detecting units; an analysis part that analyzes the signal obtained by the one or plurality of light detecting units; and a display that displays an analysis result in the analysis part. Each of the light irradiating units and each of the light detecting units are disposed on the subject such that SD distance defined on the subject as a distance between the irradiation point and the detection point is of at least two types, and the analysis part extracts one or a plurality of separated components using a signal separation method from the plurality of measurement data measured by a combination of the light irradiating unit and the light detecting unit and selects the separated components based on the SD distance dependency of the separated components and reconstructs measurement data using the selected separated component.

In the biological photometric device, the SD distance dependency may be a model parameter of a regression curve when a functional value determined by at least one of an amplitude value, an amplitude value standard deviation, and a weight value at each measurement point of the one or the plurality of separated components is plotted with respect to the SD distance or a partial optical path length in the gray matter to perform regression analysis.

In the biological photometric device, the analysis part may use the parameter to calculate a contribution ratio of a deep portion and a shallow portion in the component which is commonly included in the shallow portion and the deep portion of the subject and may use a weight which is proportional to the contribution ratio to reconstruct the deep portion component and the shallow portion component.

In the biological photometric device, the one or plurality of light detecting units may be disposed so as to detect a signal from at least two light irradiating units having different SD distances among the signals from the plurality of light irradiating units which are disposed within a radius of 60 mm from the light detecting unit on the subject.

In the biological photometric device, the one or plurality of light detecting units may detect a signal from at least two kinds of the plurality of light irradiating units at different timings.

In the biological photometric device, the one or plurality of light detecting units may be disposed so as to detect the light that is irradiated from the one or plurality of light irradiating units and propagated in a gray matter of the subject.

In the biological photometric device, the functional value may be $g(w, u, \sigma) = w \times (u^2 + \sigma^2)^{(0.5)}$ or $g(w) = w$ (w is a weight value, u is a mean amplitude value of the separated component, and $\sigma$ is a standard deviation of an amplitude value of the separated component).

In the biological photometric device, the controller may control a power of the light irradiated from the light irradiating units depending on the SD distance or a power of the light detected by the light detecting units.

In the biological photometric device, the controller may switch the use or no use of the light irradiating units or the light detecting units in accordance with the time.

In the biological photometric device, the display may display the separated components so as to divide the separated components into a shallow portion signal, a deep portion signal, a signal which is commonly included in the shallow portion and the deep portion or divide the signals in a plurality of SD distances, or divide signals in a measurement point including at least one of a frontal region, a temporal region, a parietal region, and an occipital region of head of the subject, or divide the separated components into a response signal of a task including at least one of a memory task, a motor task, a verbal task, and a visual task.

The biological photometric device may further include: a support that supports the light irradiating units and the light detecting units. The support additionally or detachably supports an auxiliary light detecting unit in order to increase the measurement points, and the auxiliary light detecting unit detects the light at a timing when the auxiliary light detecting unit is synchronized with at least one of the plurality of light detecting units.

The biological photometric device may further include an input unit that manually inputs a control method in the controller and an analysis method in the analysis part.

In the biological photometric device, the plurality of light irradiating units and the plurality of light detecting units may be disposed such that the SD distance in at least two measurement points is larger than approximately 10 mm.

In the biological photometric device, a component including at least one of a biological signal in a shallow portion of the subject, a biological signal in a deep portion, a systemic biological signal, a device noise, and a noise due to a body motion may be separated and extracted.

A biological photometric method uses a biological photometric device including one or a plurality of light irradiating units that irradiates light on a subject; one or a plurality of light detecting units that detects the light, which is irradiated on an irradiation point on the subject from the one or plurality of light irradiating units and propagated in the subject, at a detection point on the subject; a controller that controls the one or plurality of light irradiating units and the one or plurality of light detecting units; and an analysis part that analyzes the signal obtained by the one or plurality of light detecting units, the method includes disposing each of the light irradiating units and each of the light detecting units on the subject such that SD distance defined on the subject as a distance between the irradiation point and the detection point is of at least two types; extracting one or a plurality of separated components using a signal separation method from the plurality of measurement data measured by a combination of the light irradiating unit and the light detecting unit; and selecting the separated components based on the SD distance dependency of the separated components and reconstructing measurement data using the selected separated component.

Advantageous Effects of Invention

In a typical human head structure, change in a partial mean optical path length of a scalp (skin) is smaller than change in an SD distance. In contrast, in a partial mean optical path length of a gray matter (brain), the SD distance is substantially linearly increased in a range of about 10 mm or larger and 40 mm or smaller. Therefore, in the human head structure, the partial mean optical path length of a layer inherently has SD distance dependency. Further, an amplitude of an NIRS signal which is analyzed based on a Modified Beer-Lambert law is proportional to the partial optical path length in a hemodynamic variation region. From these reasons, from the SD distance dependency of a weigh value (corresponding to contribution for amplitude value) of separated components obtained from measurement data by the signal separating method, the separated signals may be discriminated into a signal from the brain or a signal from the scalp. The SD distance dependency of the partial mean optical path length of each layer depends only on the head structure and an optical property and has almost similar tendency regardless of the subjects. Therefore, even though an optical path length shows personal difference, it is possible to discriminate the signal from the brain and the signal from the scalp by adjusting a threshold value when the separated component is selected as a brain component or a scalp component.

According to the aspects of the invention, in consideration of the personal difference, it is possible to accurately discriminate the signal from the brain and the signal from the scalp and measure a variation in a tissue blood volume in accordance with the purpose such as extracting the signal from the brain or the signal from the scalp or extracting an overlapping signal of the signal from the brain and the signal from the scalp. Further, in a device configuration to achieve the above object, it is possible to efficiently obtain a signal while avoiding interference between the measurement points by arrangement of the probes of a multiple SD distance method.

BRIEF DESCRIPTION OF DRAWINGS

FIG. 5 is a view explaining component discrimination of independent components by the weight value gradient.

FIG. 6 is a view illustrating an example of probe arrangement in a human head.

FIG. 20 is a view illustrating a setting screen of the probe arrangement and the SD distance.

DESCRIPTION OF EMBODIMENTS

Hereinafter, embodiments of the invention will be described with reference to the drawings.

First Embodiment

Figure 1:
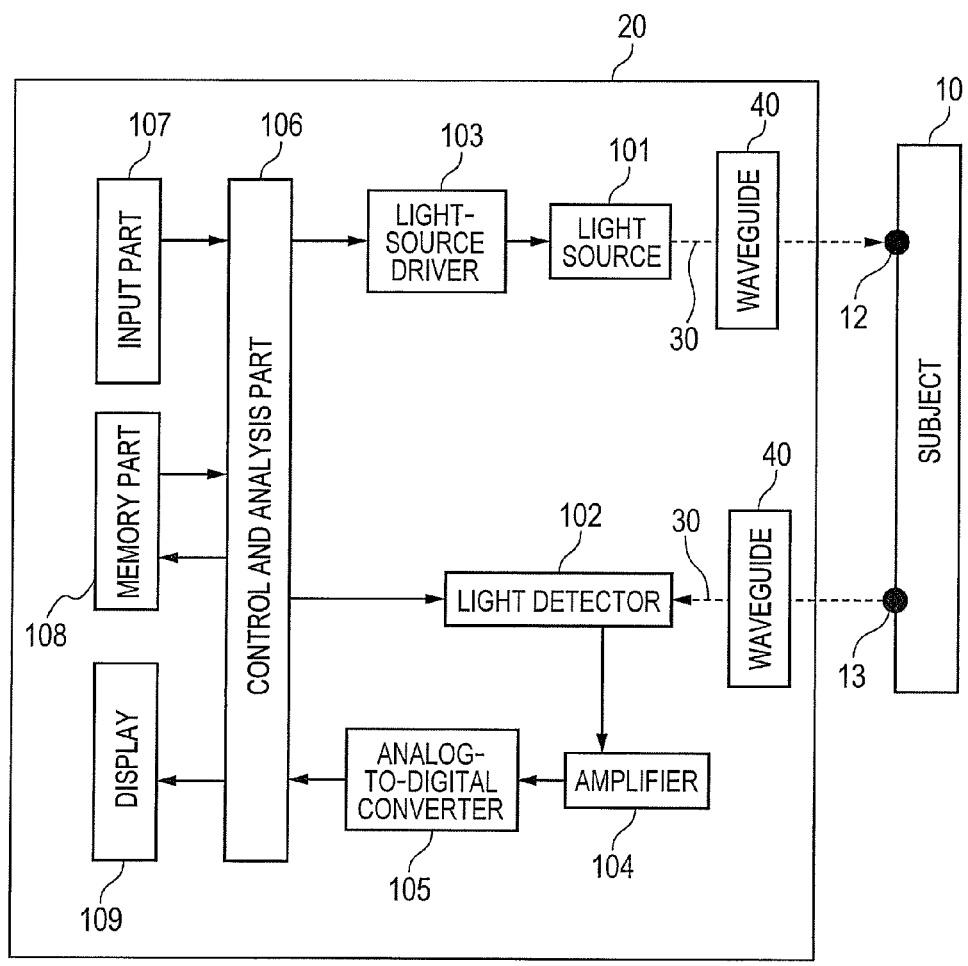
FIG. 1 is a view illustrating a configuration of a device according to the present invention.

FIG. 1 shows an example of a configuration of a device according to the present invention. In a biological photometric device that detects light which enters into a biological body, scattered, absorbed, and propagated in the biological body and then exits from the biological body, the light 30 which is irradiated from one or a plurality of light sources 101 included in a main body 20 enters into a subject 10 through a waveguide 40. The light 30 that enters into the subject 10 from an irradiation point 12 and then is transmitted and propagated in the subject 10 is detected by one or a plurality of light detectors 102 from a detection point 13 which is spaced apart from the irradiation point 12 through the waveguide 40. An SD distance is defined by a distance between the irradiation point 12 and the detection point 13 as described above.

Here, one or the plurality of light sources 101 may be a laser diode (LD) or a light emitting diode (LED) and one or the plurality of light detectors may be an avalanche photo-diode (APD), a photodiode (PD), or a photomultiplier tube (PMT). Further, the waveguide 40 may be an optical fiber, glass, or a light guide.

The light source 101 is driven by a light source driver 103 and a gain of one or the plurality of light detectors 102 is controlled by a control and analysis part 106. The control and analysis part 106 also controls the light source driver 103 and receives conditions from an input part 107.

An electric signal which is photoelectrically converted by the light detector 102 is amplified by an amplifier 104, analog to digital converted by an analog-to-digital converter 105 and then sent to the control and analysis part 106 to be processed.

In the control and analysis part 106, analysis is performed based on a signal detected by the light detector 102. Specifically, a digital signal converted by the analog-to-digital converter 105 is received and an oxygenated hemoglobin concentration length change and deoxygenated hemoglobin concentration length change (oxy-Hb and deoxy-Hb) are calculated from change in a detected light intensity or change in an absorbance based on the digital signal on the basis of, for example, a method disclosed in Non-Patent Literature 1. Here, the concentration length change is a changed amount of a product of the concentration and an optical path length.

Here, it is assumed that the control and analysis part 106 drives the light source 101, controls a gain of the light detector 102, and processes a signal from the analog-to-digital converter 105. However, individual control parts may be provided and a unit that combines the individual control parts may be provided to perform the same function as the control and analysis part 106.

Further, the measurement data and the hemoglobin concentration length change calculating result are stored in a memory part 108 and the measurement result may be displayed on a display 109 based on the analysis result and/or stored data.

Even though an optical transmitter 50 and an optical receiver 60 are not illustrated in FIG. 1, the optical transmitter 50, for example, includes the waveguide 40 at a light source 101 side and disposed so as to be in contact with or almost contact with the subject 10. The optical receiver 60, for example, includes the waveguide 40 at a light detector 102 side and disposed so as to be in contact with or almost contact with the subject 10. In this case, on the subject 10, the optical transmitters 50 and the optical receivers 60 are disposed such that light which is received by each optical receiver is propagated in both the gray matter and the scalp. This is because the signal from the brain needs to be included when the gradient is calculated in order to assume that the signal from the brain included in an optical receiving signal is approximately and linearly increased in accordance with the SD distance in the analyzing method described below. If the SD distance is significantly short and thus a mean optical path length of the gray matter is short, it is difficult to precisely calculate the gradient for the SD distance of the signal component from the brain.

Next, a method of separating and extracting a signal from the brain and a signal from the scalp using the measurement data and the hemoglobin concentration length change calculating result will be described. The method uses independent component analysis (ICA) to extract a plurality of independent components from the NIRS signal obtained by the measurement and classifies the independent components into a brain component or a scalp component. The independent component analysis is an analysis method that is capable of separating linearly mixed signals without requiring transcendental information as one of signal separating methods. The method is effective in analyzing data which has a plurality of signal sources and is measured at plural points.

Hereinafter, a method that applies the independent component analysis only to oxy-Hb having a larger amplitude between two components of the hemoglobin concentration length change obtained by the NIRS measurement and separates the signal from the brain and the signal from parts other than the brain from the result will be described. However, deoxy-Hb or all of hemoglobin concentration length changes (oxy-Hb+deoxy-Hb) may be used.

Figure 2:
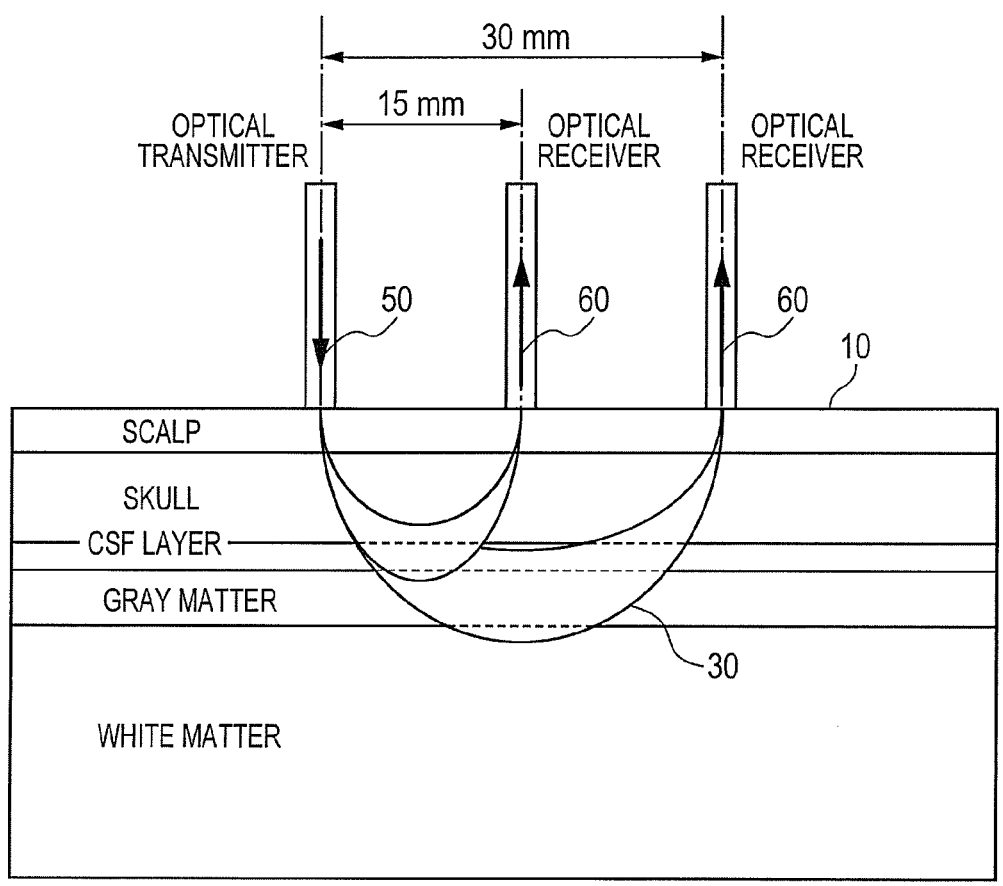
FIG. 2 is a view illustrating an example of a measurement cross-sectional view of a multiple SD distance method.
Figure 3:
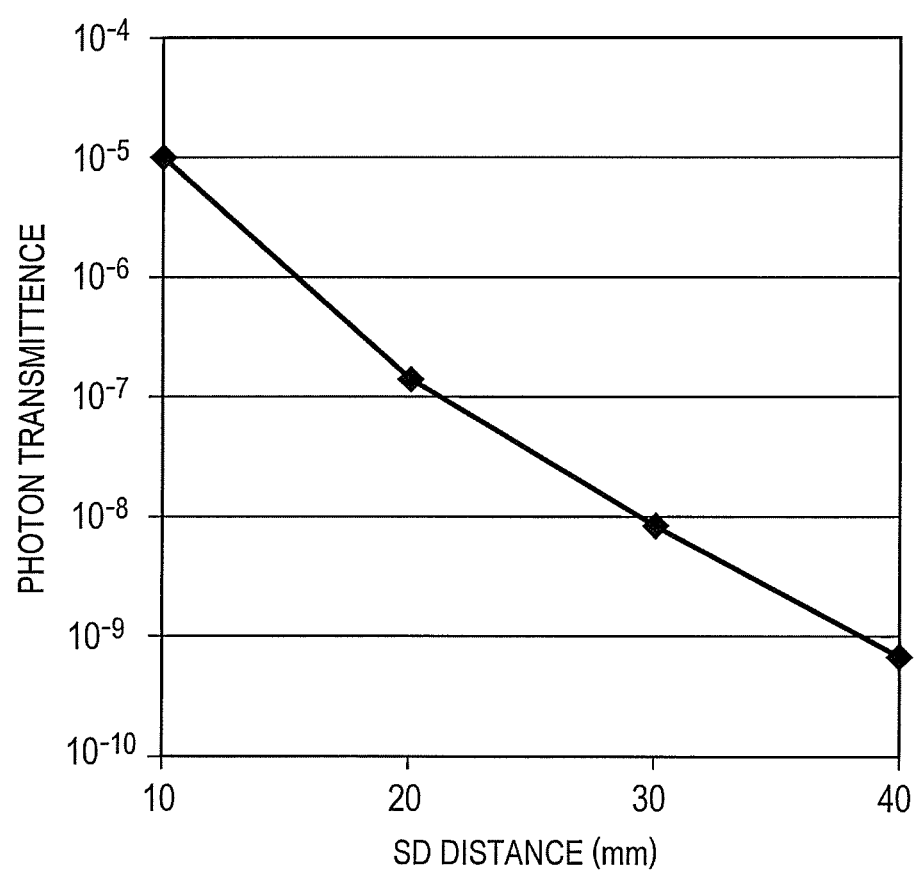
FIG. 3 is a view illustrating relationship between an SD distance and a photon transmittance in a typical head model.

FIG. 2 illustrates an example of a measurement cross-sectional view of a multiple SD distance method. The light 30 which is irradiated from the optical transmitter 50 enters from the upper portion of the scalp and is propagated in a tissue in all directions. If the optical receivers 60 are disposed at an SD distance of 15 mm and an SD distance of 30 mm, as illustrated in FIG. 2, the light 30 which is received by the optical receiver 60 at the SD distance of 15 mm transmits an averagely shallower region than light 30 which is received by the optical receiver 60 at the SD distance of 30 mm. FIG. 3 shows a result obtained by calculating the relationship between the SD distance and the photon transmittance in a typical head model by Monte Carlo simulation. In the case of the SD distance of 15 mm and the SD distance of 30 mm, as illustrated in FIG. 3, the difference of the photon transmittances is approximately double digits. The difference is caused by the different mean optical path lengths in the tissue. Here, the partial mean optical path length on every layer of the head is changed by the SD distance.

Figure 4A:
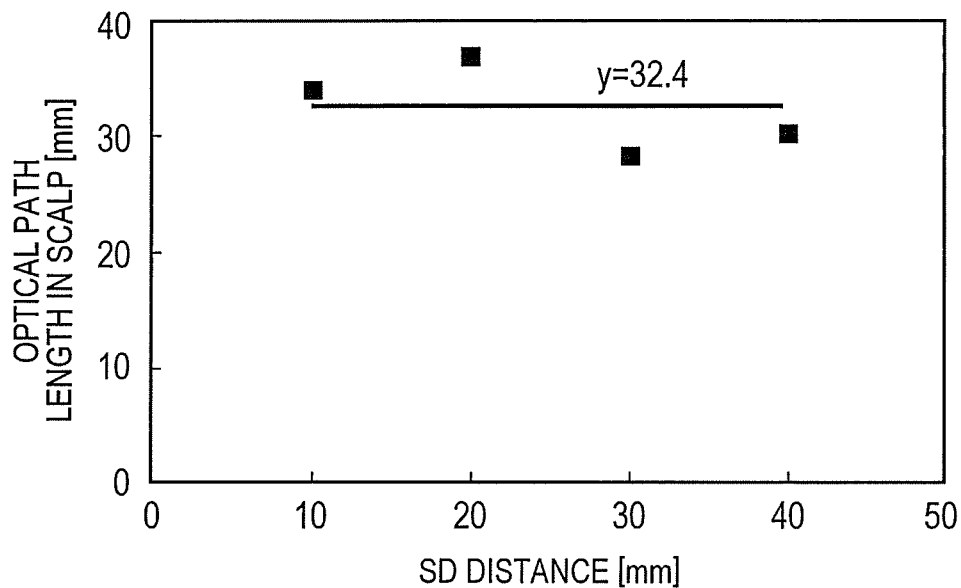
FIG. 4A is a view illustrating a relationship between the SD distance and a partial mean optical path length in a scalp.
Figure 4B:
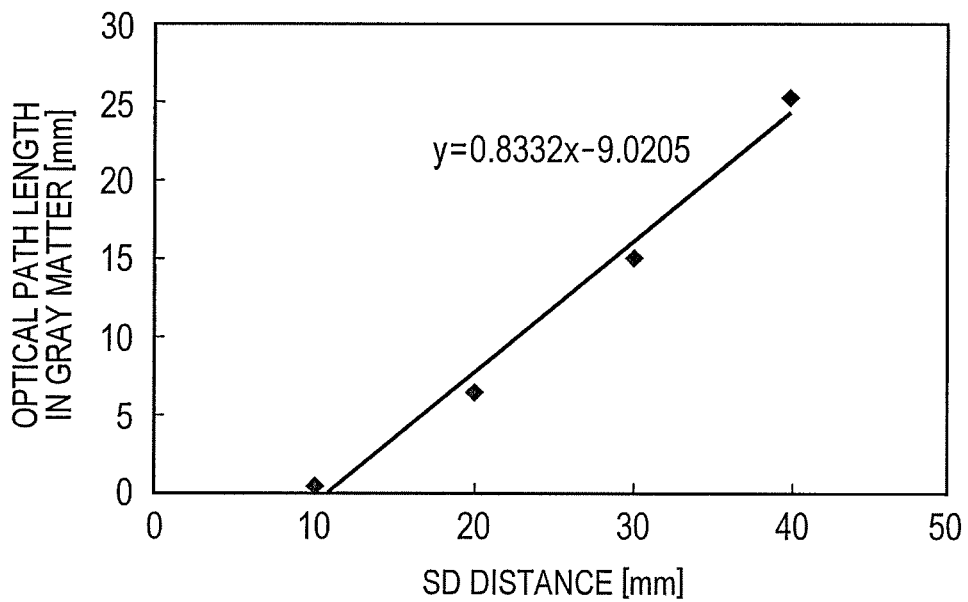
FIG. 4B is a view illustrating a relationship between the SD distance and a partial mean optical path length in a gray matter.

FIGS. 4A and 4B are views illustrating a relationship between the SD distance and partial mean optical path lengths in the scalp and the gray matter obtained by the Monte Carlo simulation in which FIG. 4A illustrates the relationship between the SD distance and the partial mean optical path length in the scalp and FIG. 4B illustrates the relationship between the SD distance and the partial mean optical path length in the gray matter. A horizontal axis represents the SD distance (mm) and a vertical axis represents the optical path lengths (mm) in the scalp and the gray matter. The partial optical path length in the scalp does not exhibit the SD distance dependency but the partial optical path length in the gray matter exhibits the linear SD distance dependency. The partial mean optical path length in the scalp is varied because the number of calculated photons of the simulation is small and thus the result is not converged. Since the NIRS signal intensity is proportional to the partial optical path length of a region where the blood flow is changed (see Non-Patent Literature 1) (it is assumed that the blood flow is uniformly changed in the partial optical path), as illustrated in FIGS. 4A and 4B, if the SD distance is increased, it is expected that the brain component in the NIRS measurement signal is increased but the scalp component is not changed. The present invention focuses on changed amount of the signal intensity with respect to the SD distance, that is, the gradient (slope).

As illustrated in FIGS. 4A and 4B, if the partial optical path length in the gray matter is Lgray (mm) and the SD distance is SD (mm), the relationship therebetween is represented by Equation 1.

[Equation 1]

$$L_{gray} = 0.833 \times SD - 9.020 [mm] \quad (1)$$

Here, if it is assumed that the partial optical path length (Lgray (mm)) in the gray matter is not temporally changed and a general amplitude ΔCL (changed amount of a product of a hemoglobin concentration and the optical path length) of the NIRS measurement signal is 0.1 mMmm (=(mmol/l)×(mm)) for descriptive purposes (Equation 2), and L=Lgray=15.97 mm (in case of SD=30 mm in FIG. 4) is substituted, ΔC is obtained as represented in Equation 3.

[Equation 2]

$$\Delta C \times L_{gray} = 0.1 [mMmm] \quad (2)$$

[Equation 3]

$$\Delta C = 0.1/L_{gray} = 0.1/15.97 = 6.26 \times 10^{-3} [mM] \quad (3)$$

Therefore, Equation 4 is obtained by multiplying both sides of Equation 1 by ΔC.

[Equation 4]

$$\Delta CL_{gray} = 0.0052 \times SD - 0.056 [mMmm] \quad (4)$$

Here, if an amplitude value of an i-th independent component is Ui(t) as a function of time and a weight value of the i-th independent component at the SD distance of s (mm) is W (i, s) (i=1, 2, . . . , n) when the number of independent components is n, the NIRS signal ΔCL (s, t) at each timing in each SD distance is represented by linear coupling of the independent components as represented in Equation 5.

[Equation 5]

$$\Delta CL(s,t) = W(1,s) \times U_1(t) + \ldots + W(n,s) \times U_n(t) [mMmm] \quad (5)$$

Here, a root mean square Urms of the independent components is represented by Equation 6 using a time average Umean and a standard deviation Ustd of the independent components.

[Equation 6]

$$U_{rms} = \sqrt{U_{mean}^2 + U_{std}^2} \quad (6)$$

Since a contribution portion which is proportional to the optical path length is reflected on the relationship of Equation 5 and data which is simultaneously measured at a plurality of SD distances, it is considered that the gradient d (|W×Urms|)/d (SD) (mMmm/mm) of an absolute value of the product of the weight value and the root mean square of the independent component is ideally equal to a gradient d (ΔCL)/d (SD)=0.0052 (mMmm/mm) with respect to the SD distance of an amplitude of the NIRS signal derived from Equation 4 so that Equation 7 is obtained.

[Equation 7]

$$d(|W \times Urms|)/d(SD) = d(\Delta CL)/d(SD) = 0.0052 [mMmm/mm] \quad (7)$$

Equation 7 assumes a typical head model. Further, the amplitude value of the NIRS measurement signal is assumed as ΔCL=0.1 (mMmm) for descriptive purposes as described above. Here, using the gradient d (|W×Urms|)/d (SD) (mMmm/mm) of the absolute value of the product of the weight value and the root mean square of the independent component, in order to separate the signal from the brain (specifically, gray matter) and the signal from the skin (scalp), a threshold value of d (|W×Urms|)/d (SD) (mMmm/mm) is set and it is assumed that an independent component which is smaller than the threshold value is not the brain component. Such a component is considered as a scalp component or a noise component. The gradient may be calculated by obtaining the regression line by the least-square method. As described above, after separating the independent components by the ICA, results of reconfiguration using an independent component which is equal to or larger than the threshold value and an independent component which is smaller than the threshold value become the signal from the brain and the signal from the scalp. A method that makes the threshold value, for example, approximately half the gradient calculated here is considered. However, in principle, an optical path length of the head is varied for every subject and the signal amplitude is varied for every task. Therefore, it is desirable to optimize the threshold value for every subject and for every task.

Here, the regression to a linear function will be described. However, if the partial mean optical path length of the gray matter with respect to the SD distance in FIG. 4 depends on the head structure but is not a linear function, more general polynomial regression or a method that regresses to an exponential function, a logarithm function, a hyperbolic function, or any other functions may be used.

FIG. 5 plots a weight value of each of the independent components with respect to the SD distance when two types of SD distances, that is, 15 mm (one point) and 30 mm (two points) are used and two types of independent components extracted from the signals are used. The horizontal axis is the SD distance and the vertical axis is the weight value of the independent component. A straight line obtained in each of the independent component by the least-square method and a straight line corresponding to the threshold value of the gradient are simultaneously illustrated. In FIG. 5, since a gradient of a component 1 is the threshold value or higher, the component 1 is determined as a brain component. Further, since a gradient of a component 2 is lower than the threshold value, the component 2 is determined as a scalp component.

In the method, since the gradient of the weight value of the independent component with respect to the SD distance is used, measurement data having an SD distance of approximately 10 mm or longer is required so that the partial mean optical path length of the gray matter is 0 or larger. Here, approximately 10 mm means 7 mm or longer and 13 mm or shorter.

In FIG. 5, the weight value of the independent component is used as the function value. However, an amplitude value or a standard deviation of the amplitude values may be used.

Further, a method that calculates the gradient using the absolute value of the product of the weight value and the root mean square of the independent component as the threshold value has been described. However, if the independent components are appropriately normalized, the gradient may be calculated only using the weight value of the independent component. In other words, a gradient of the function g with respect to the SD distance when a function g determined by any one of the weight value, the mean amplitude value, and the standard deviation of the amplitude values is g (w, u, σ)=w×(u^2+σ^2)^(0.5) or g(w)=w (w is a weight value, u is a mean amplitude value of the separated component, and σ is a standard deviation of amplitude values of the separated component) may be used as the threshold value.

Further, the terminologies used here "brain component" and "scalp component" are expediential terms and are NIRS signals reconfigured by an independent component which is formally separated by the gradient of the weight value with respect to the SD distance by the above method and a plurality of separated independent components. Therefore, for example, it is considered that the "brain component" may include a blood variation component in a blood vessel in the skull in addition to a biological signal of a deep tissue including the brain. In addition, the "scalp component" may include non-brain component, that is, a systemic biological signal, device noise, or noise caused by the body motion in addition to a biological signal of a shallow tissue.

Here, even though an independent component analysis is described as a signal separating method, the method of the present invention may be carried out even when a signal separating method such as main component analysis, factor analysis, multiple regression analysis, or cluster analysis is used.

Figure 7A:
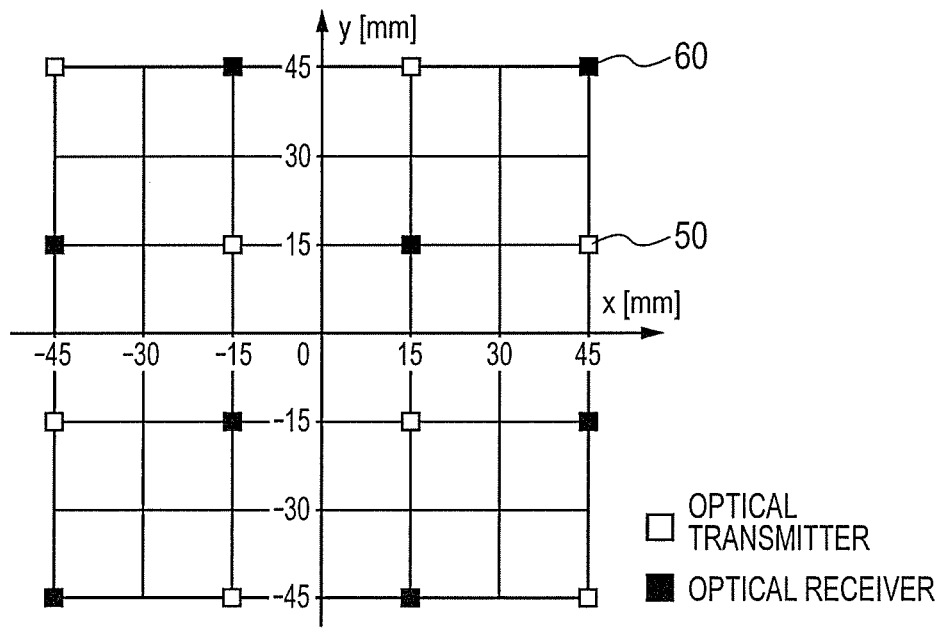
FIG. 7A is a view illustrating an example of a matrix type probe arrangement in a related art.
Figure 7B:
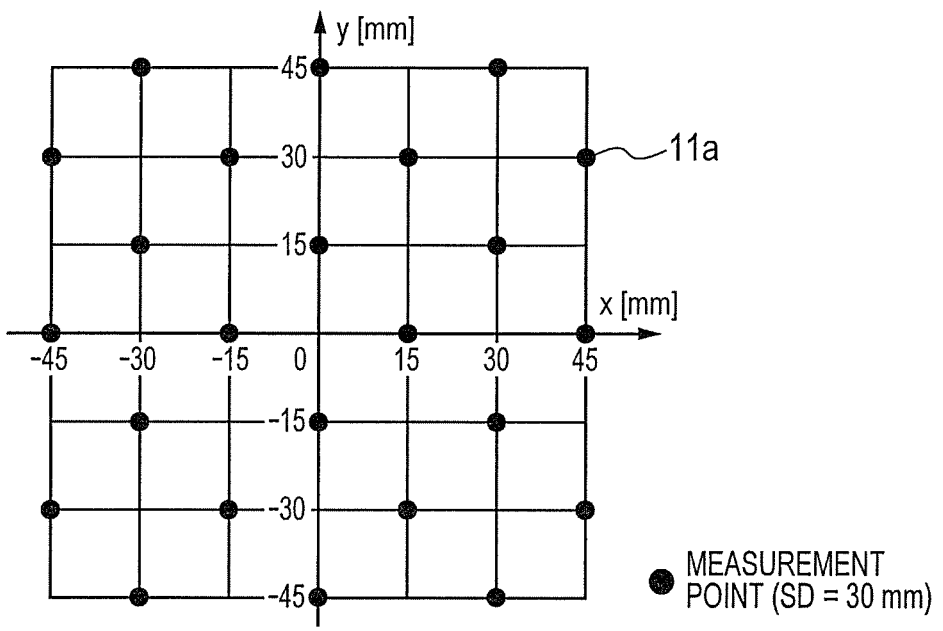
FIG. 7B is a view illustrating an example of arrangement of measurement points of the matrix type probe arrangement of in a related art

Next, it is described that the above method is applied to the measurement with actual probe arrangement. FIG. 6 illustrates an example of a probe arrangement in the human head. The probe may be arranged in the entire head including a frontal region, a temporal region, a parietal region, and an occipital region. FIG. 7A illustrates a matrix type probe arrangement in the related art (for example, see Non-Patent Literature 1) and FIG. 7B illustrates arrangement of measurement points. In the arrangement, an interval between the optical transmitter 50 and the optical receiver 60 is usually approximately 30 mm and a substantially center point becomes a measurement point 11a. "□", "■", and "●" indicate the optical transmitter, the optical receiver, and the measurement point, respectively. In the arrangement, the SD distance is 30 mm at all measurement points 11a. Even though the measurement may be performed at the combination with the SD distance of 60 mm, the signal to noise ratio (SNR) becomes smaller and the method is not realistic.

Figure 8A:
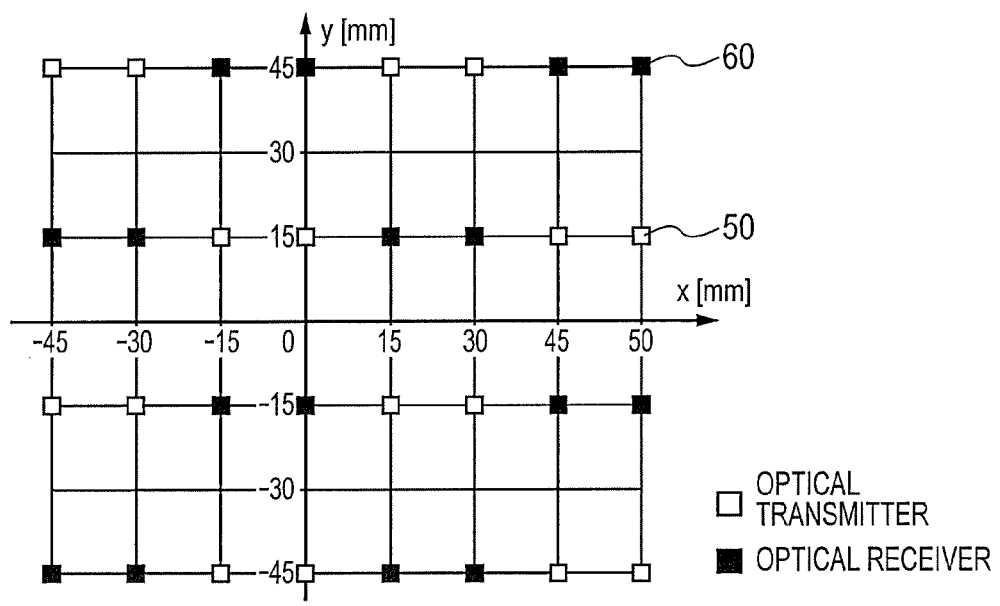
FIG. 8A is a view illustrating an example of double density probe arrangement.
Figure 8B:
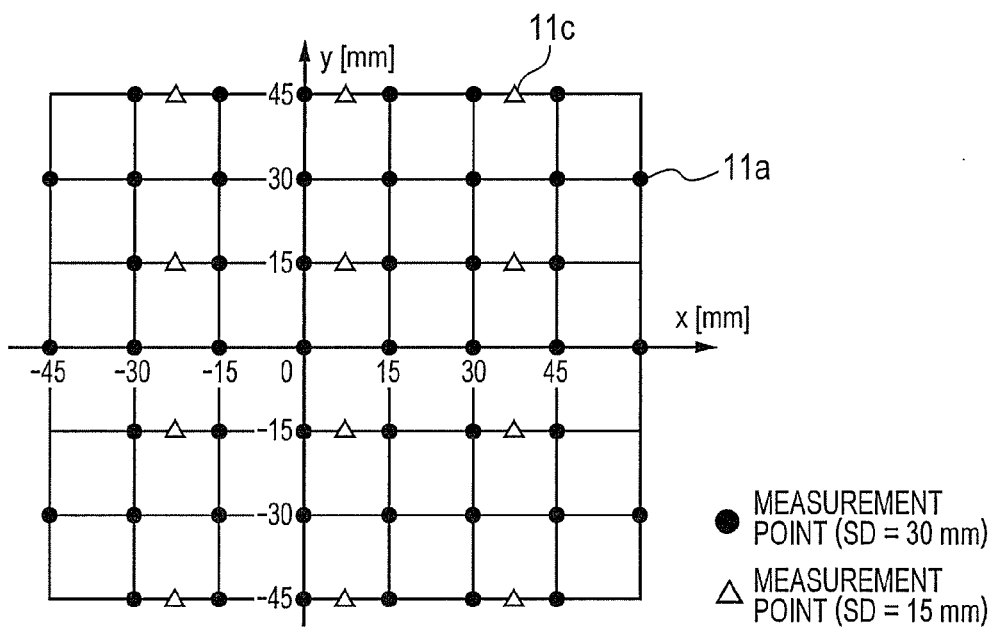
FIG. 8B is a view illustrating an example of arrangement of measurement points in the double density probe arrangement.

FIG. 8A illustrates double density probe arrangement and FIG. 8B illustrates the arrangement of measurement points. The probe arrangement is disclosed in Patent Literature 9 and Non-Patent Literature 6. The arrangement is an arrangement where the matrix type probe arrangement of FIG. 7 is shifted by 15 mm on the X-axis to overlap with each other. "□", "■", "●", and "Δ" indicate the optical transmitter 50, the optical receiver 60, the measurement point 11a at the SD distance of 30 mm, and the measurement point 11c at the SD distance of 15 mm, respectively.

Here, in order to extract the signal from the scalp, measurement signals at measurement points in a plurality of SD distances are used. The signal is used to select a component to be used after separating the components of the signals. In the case of mapping by the interpolation only using the measurement signal at the same SD distance, for example, if the SD distance is approximately 15 to 20 mm, a map in which contribution of a signal from a shallow portion including the scalp is large is obtained.

Here, by the SD distance, if imaging is performed only using data at the same SD distance, the number of measurement points is small. Therefore, the resolution may be lowered. In the example of FIGS. 8A and 8B, the number of the measurement points in the SD distance of 15 mm is smaller than that of the measurement points in the SD distance of 30 mm and thus the distribution density is small. Even the measurement data in the SD distance whose distribution density is small is effective in extracting a signal (the signal from the brain or the signal from the scalp) which will be separated from the data at the measurement point in the SD distance of 30 mm. Therefore, even when the number of the measurement points is small, effective measurement data may be obtained.

Figure 9A:
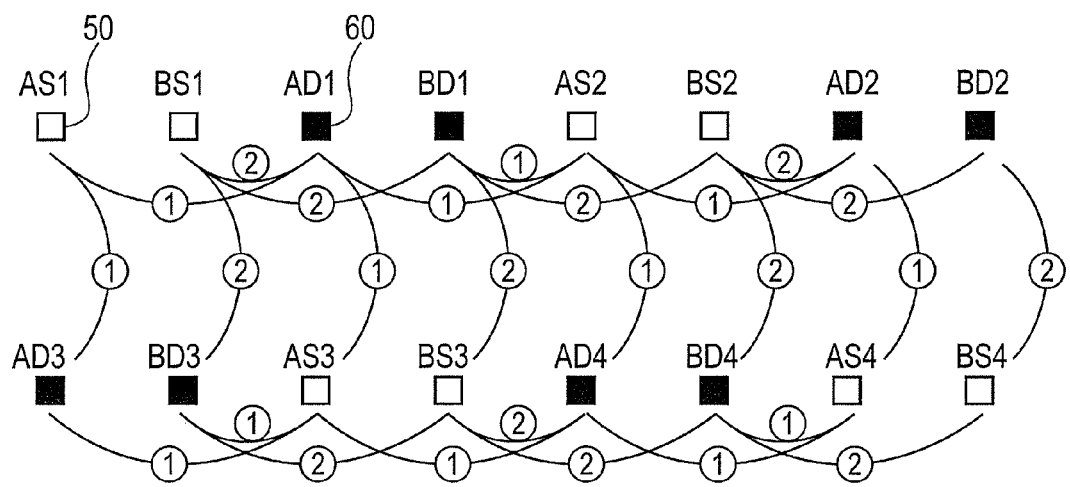
FIG. 9A is a view illustrating a first example of the probe arrangement and a lighting order of light sources.
Figure 9B:
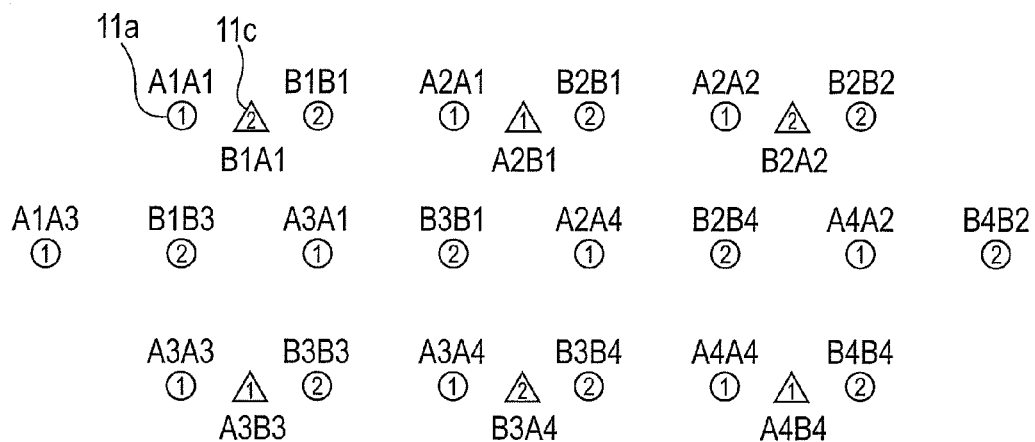
FIG. 9B is a view illustrating a first example of the arrangement of measurement points and a measuring order.
Figure 10:
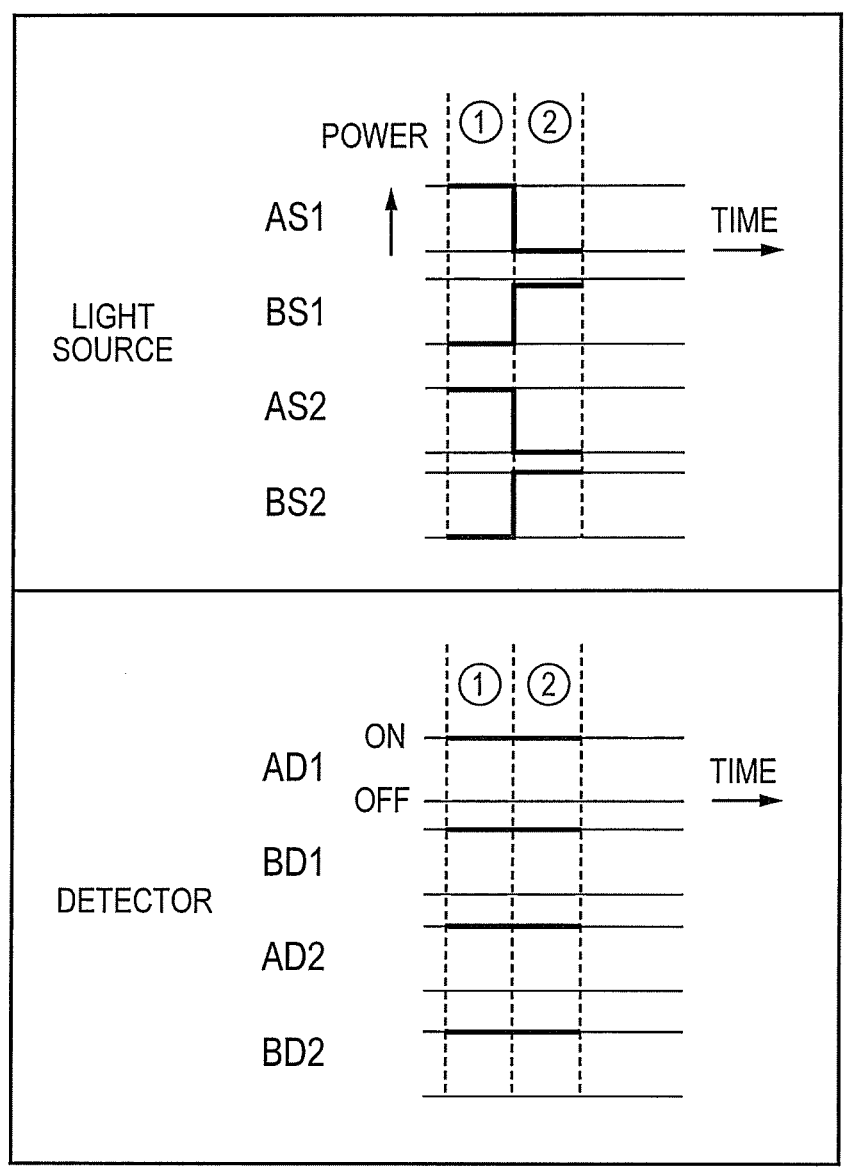
FIG. 10 is a view illustrating a first example of a lighting order of the light sources and a measuring order by a detector.

In order to perform measurement in two types of SD distances as described above, a method that switches the lighting order of the light sources will be described below. If all light sources are simultaneously turned on, each of the detectors receives a signal of the SD distance of 15 mm and a signal of the SD distance of 30 mm simultaneously and the difference of the received light intensity is two digits (FIG. 3). Therefore, the SNR of the signal in the SD distance of 30 mm may be undesirably lowered by the influence of photocurrent shot noise accompanied by receiving the light in the SD distance of 15 mm. Therefore, if the irradiation powers of the light sources are constant, the signals in the SD distances of 15 mm and 30 mm are desirably detected at different timings. As a first method that switches the lighting order of the light sources, a first example of the probe arrangement and the lighting order of the light sources is illustrated in FIGS. 9A and 9B. FIG. 9A illustrates an upper half of the probe arrangement of FIG. 8A. "□" and "■" indicate the optical transmitter 50 and the optical receiver 60, respectively. Circled numerals 1 and 2 indicate the lighting order of the light sources. Symbols written on each probe indicate a surface (A surface/B surface), a light source/detector (S: source/D: detector), and the probe number. For example, AS1 denotes a light source No. 1 on the A surface. The probe arrangement overlaps two matrix type probe arrangements of the related art in FIG. 7A. If the probe arrangements are referred to as the A surface and the B surface, in the lighting order illustrated in FIG. 9A, the light sources on the A surface and the B surface are alternately turned on. FIG. 9B illustrates the arrangement of measurement points and the measuring order. A circle indicates the measurement point in the SD distance of 30 mm and a triangle indicates the measurement point in the SD distance of 15 mm, and the symbol written on or below the measurement point indicates a corresponding light source number and a corresponding detector number. FIG. 10 illustrates a first example of the light order of the light sources and the measuring order by the detector. Here, only a light source 1 (AS1) and a light source 2 (AS2) on the A surface, a light source 1 (BS1) and a light source 2 (BS2) on the B surface, a detector 1 (AD1) and a detector 2 (AD2) on the A surface, a detector 1 (BD1) and a detector 2 (BD2) on the B surface are illustrated. The detectors are always turned on and the light sources alternately switch the A surface and the B surface. By adopting the lighting order, the same intensity modulation frequency or lock-in frequency may be used on the A surface and the B surface and the kinds of necessary frequency may be halved. Therefore, it is easy to design the band width of the intensity modulation frequency between the light sources so as not to overlap each other.

Figure 11A:
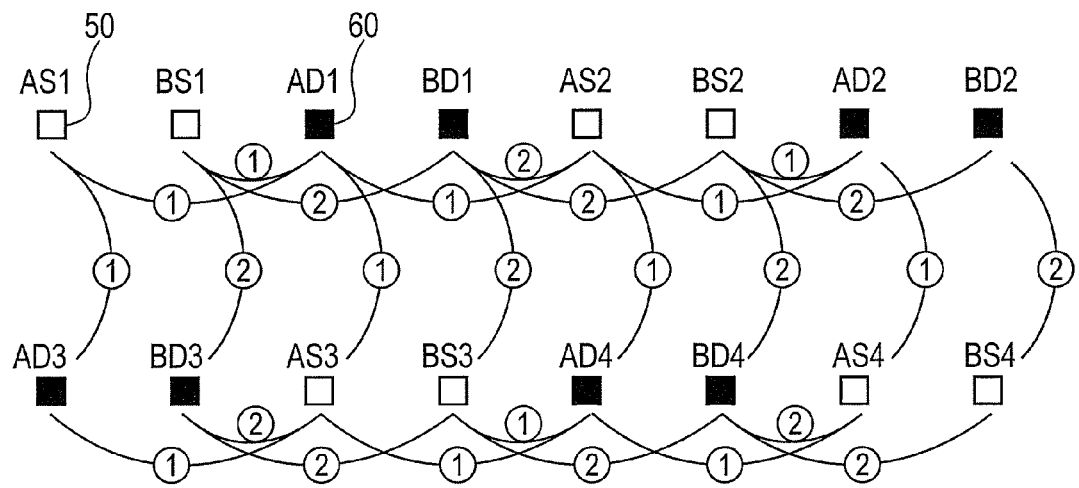
FIG. 11A is a view illustrating a second example of the probe arrangement and a lighting order of light sources.
Figure 11B:
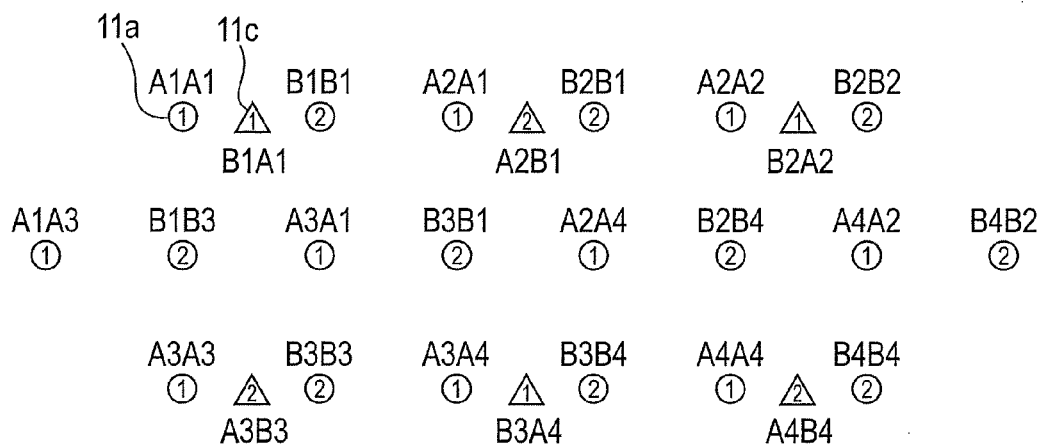
FIG. 11B is a view illustrating a second example of the arrangement of measurement points and a measuring order.
Figure 12:
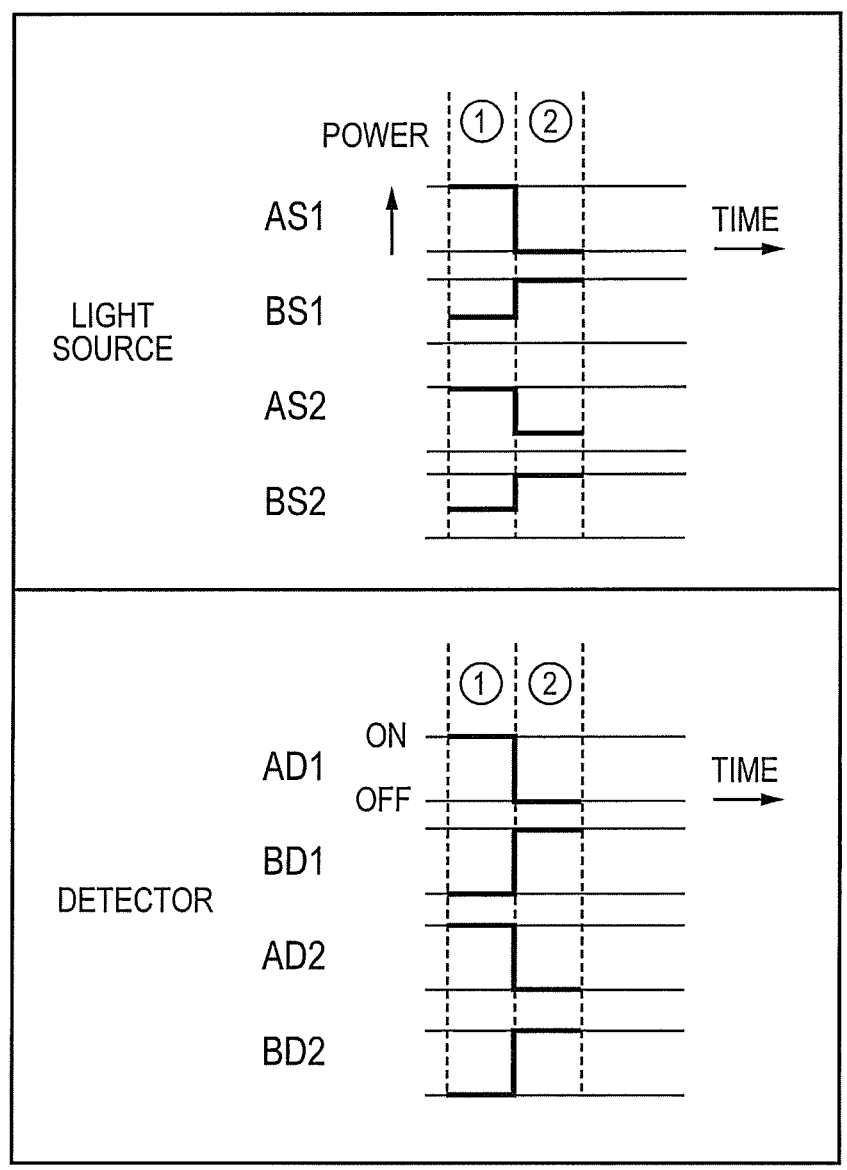
FIG. 12 is a view illustrating a second example of a lighting order of the light sources and a measuring order by a detector.

As a second method that switches the lighting order of the light sources, a second example of the probe arrangement and the lighting order of the light sources is illustrated in FIGS. 11A and 11B. The reference symbols are same as in FIGS. 9A and 9B. According to the lighting order, in the light source, the measurement in the SD distance of 15 mm and the measurement in the SD distance of 30 mm are performed at different timings. Therefore, the light amount is adjusted in accordance with the SD distances to easily adjust the gain without saturating the detector. In FIG. 12, a second example of the lighting order of the light sources and the measuring order by the detector is illustrated. The reference symbols are same as in FIG. 10. Even though the light source is always turned on, the power of the light source is set to be small at the timing in the SD distance of 15 mm and the power of the light source is set to be large at the timing in the SD distance of 30 mm. The detector simultaneously receives a signal in the SD distance of 15 mm and a signal in the SD distance of 30 mm while being used, but is turned off during a timing when the detector is not used. Since the detector is turned off while being unused, it is possible to reduce the power consumption of the detector.

Figure 13A:
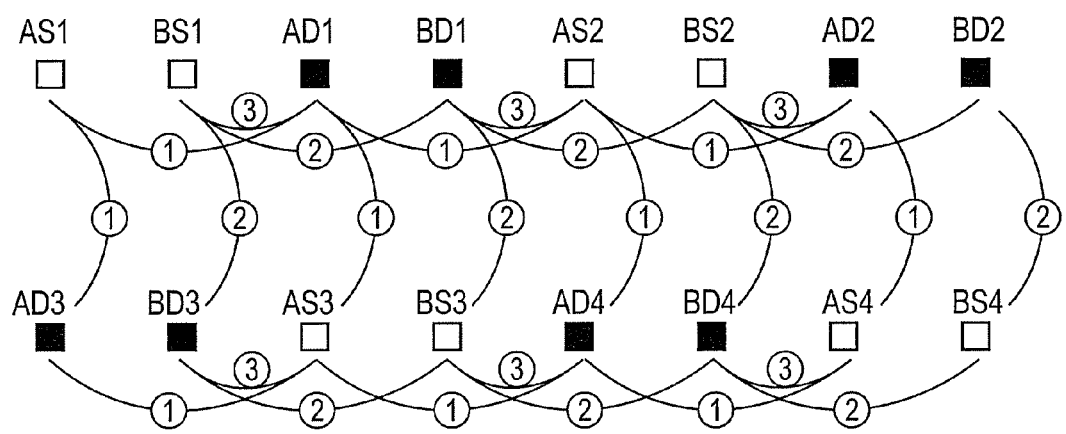
FIG. 13A is a view illustrating a third example of the probe arrangement and a lighting order of light sources.
Figure 13B:
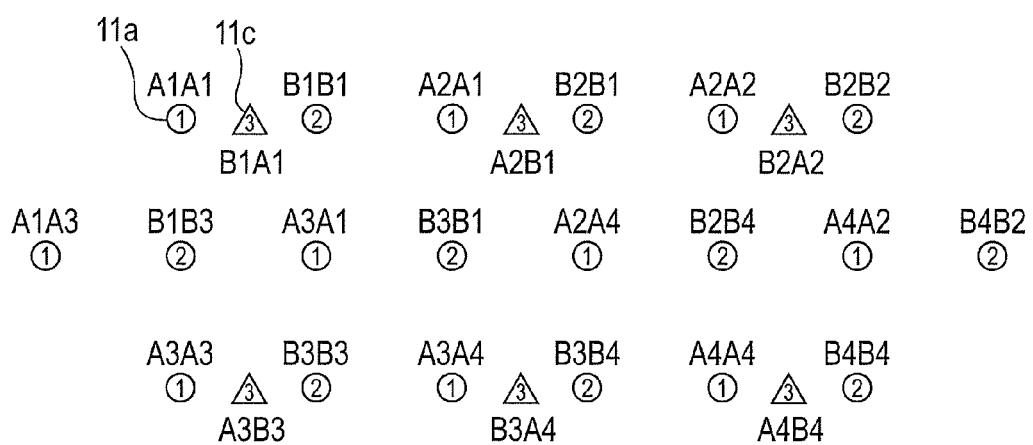
FIG. 13B is a view illustrating a third example of the arrangement of measurement points and a measuring order.
Figure 14:
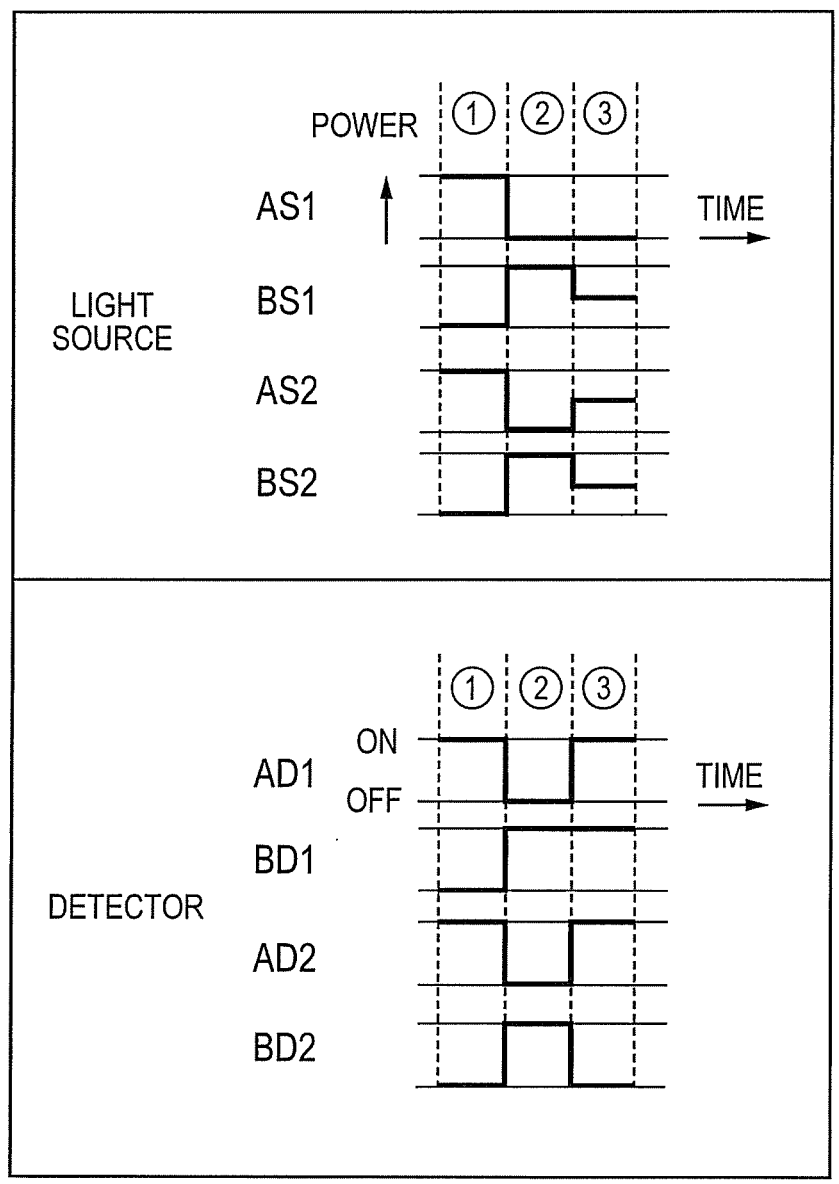
FIG. 14 is a view illustrating a third example of a lighting order of the light sources and a measuring order by a detector.
Figure 15A:
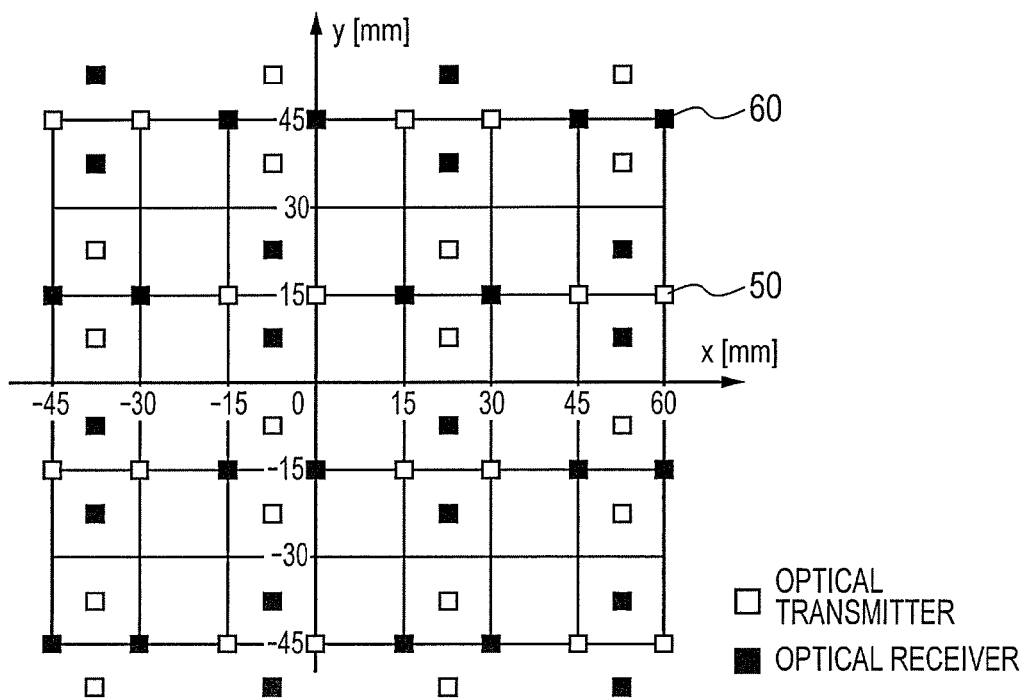
FIG. 15A is a view illustrating an example of quadruple density probe arrangement A.
Figure 15B:
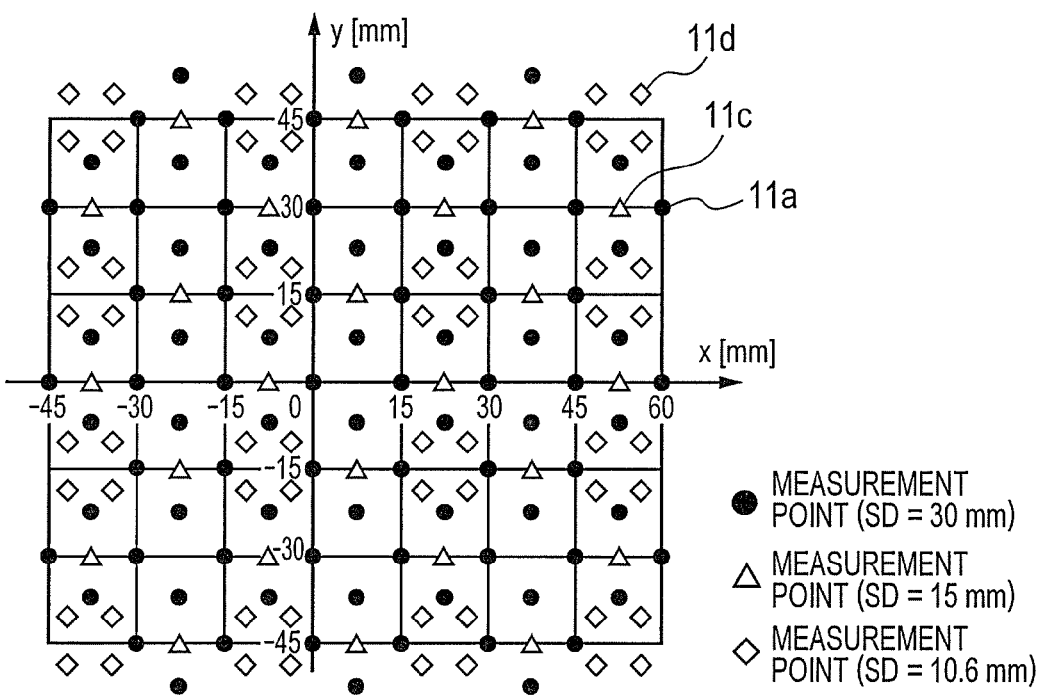
FIG. 15B is a view illustrating an example of arrangement of measurement points of the quadruple density probe arrangement A.
Figure 16A:
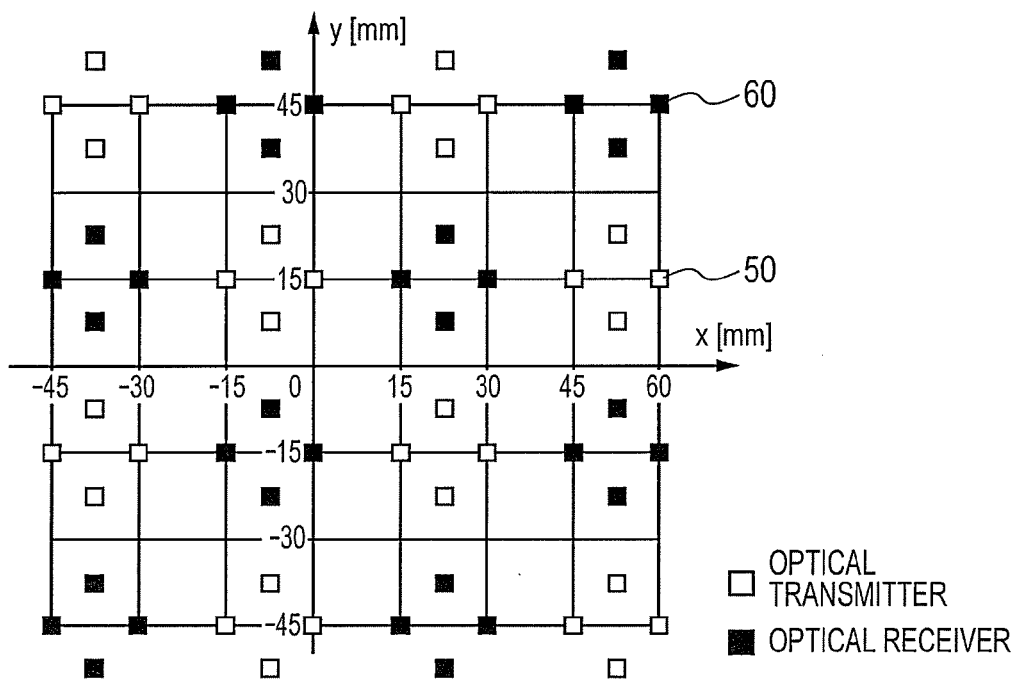
FIG. 16A is a view illustrating an example of quadruple density probe arrangement B.
Figure 16B:
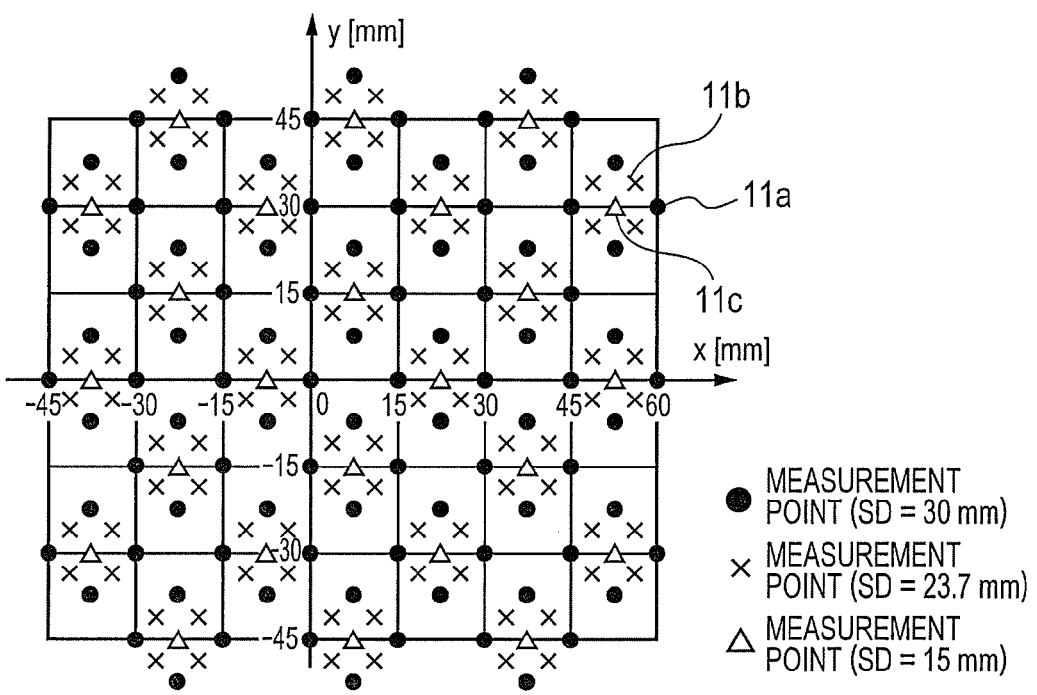
FIG. 16B is a view illustrating an example of arrangement of measurement points of the quadruple density probe arrangement B.
Figure 17A:
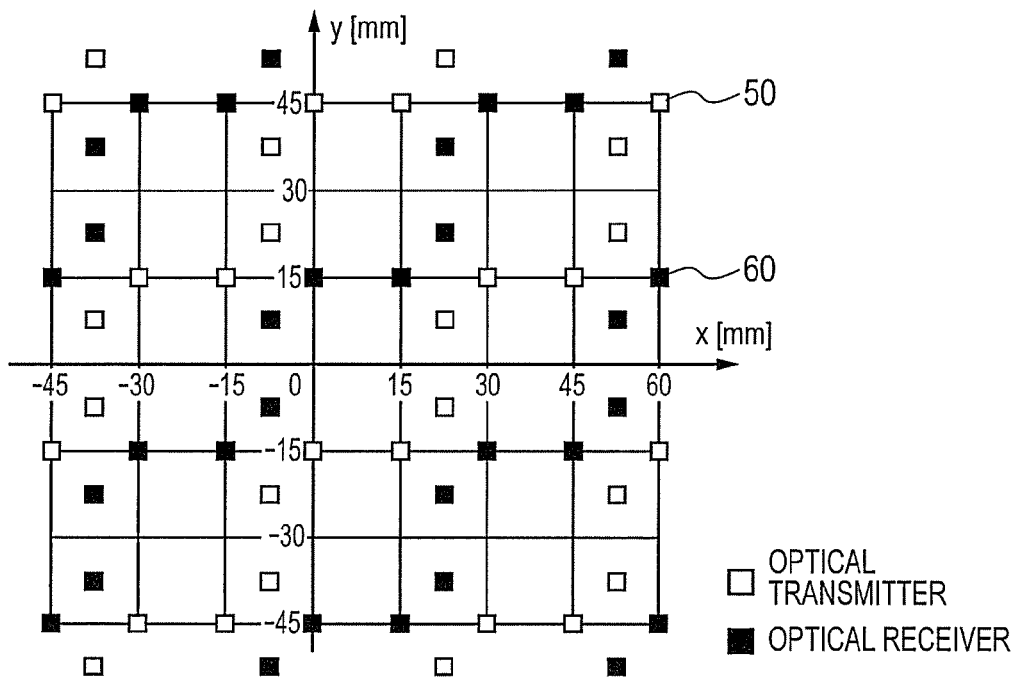
FIG. 17A is a view illustrating an example of quadruple density probe arrangement C.
Figure 17B:
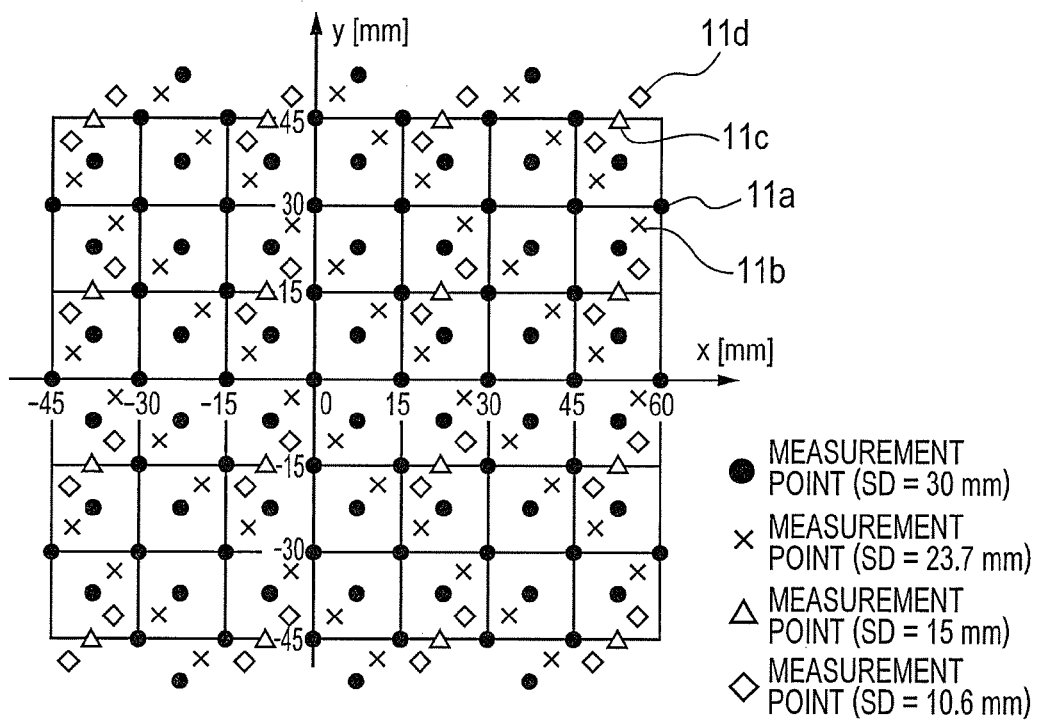
FIG. 17B is a view illustrating an example of arrangement of measurement points of the quadruple density probe arrangement C.
Figure 18A:
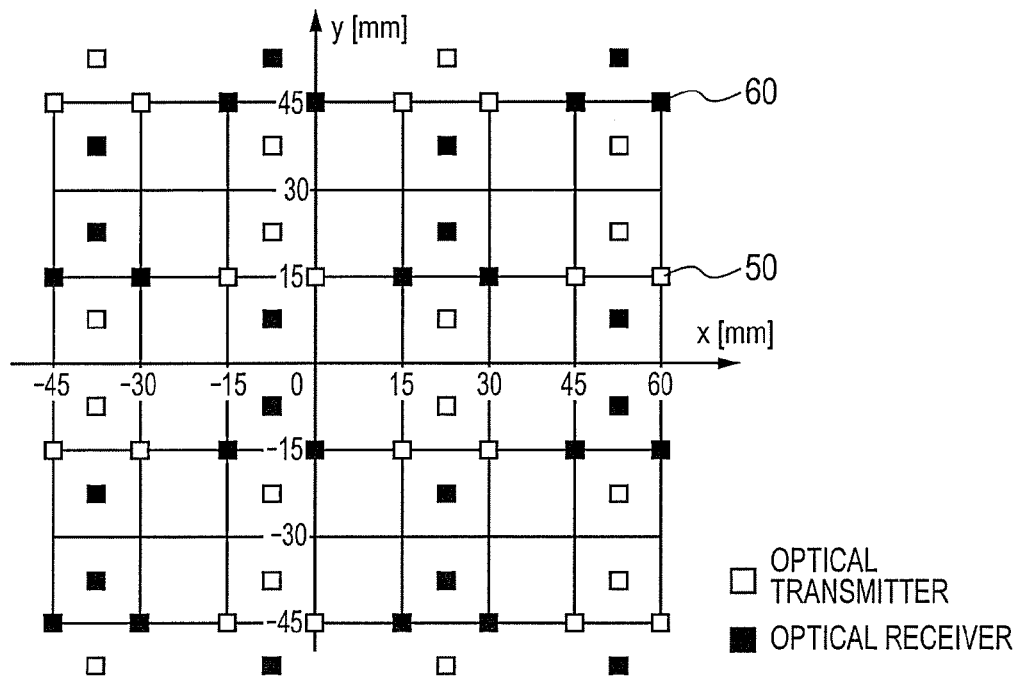
FIG. 18A is a view illustrating an example of quadruple density probe arrangement D.
Figure 18B:
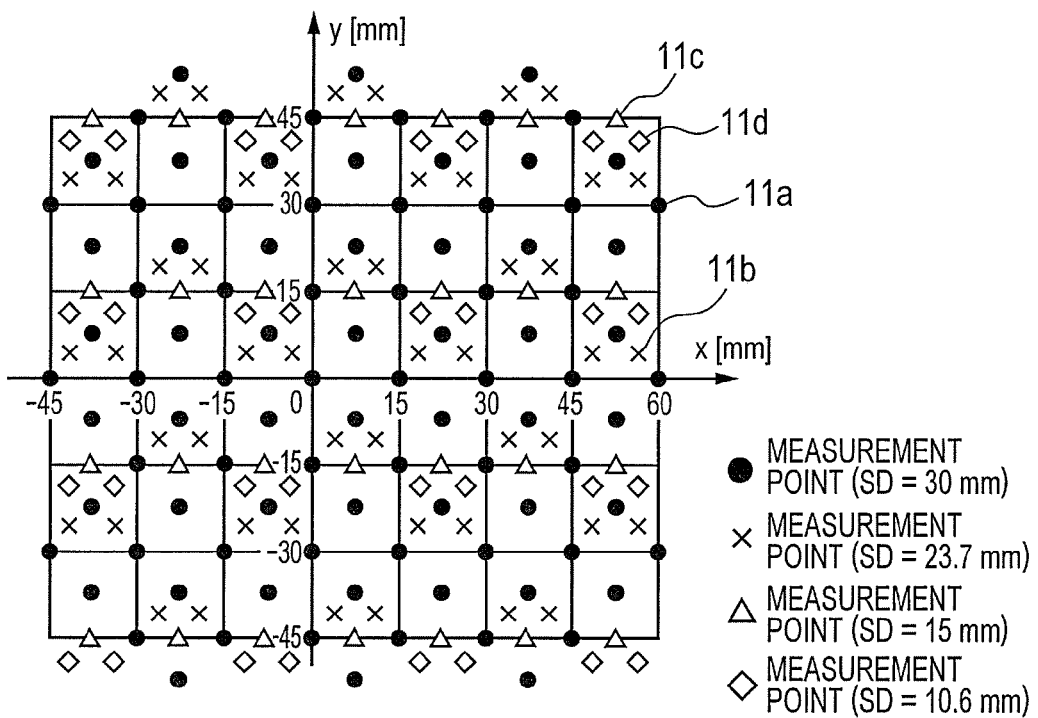
FIG. 18B is a view illustrating an example of arrangement of measurement points of the quadruple density probe arrangement D.

As a third method that switches the lighting order of the light sources, a third example of the probe arrangement and the lighting order of the light sources is illustrated in FIGS. 13A and 13B. The reference symbols are same as in FIGS. 9A and 9B. According to the lighting order, the measuring timings in the SD distance of 30 mm on the A surface and the B surface are different and a timing when the SD distance of 15 mm is measured is separately set. Even though the time resolution is lowered, an average power is lowered so that the shot noise due to the photocurrent in each detector may be lowered and the detectors are hardly saturated. In FIG. 14, a third example of the lighting order of the light sources and the measuring order by the detector is illustrated. The reference symbols are same as in FIG. 10. The light source is turned on for measurement in the SD distance of 30 mm on any one of the A surface and the B surface and also turned on for measurement in the SD distance of 15 mm. Therefore, among three lighting timings, the light source is turned on two times and turned off one time. However, since AS1 is disposed at an edge and no detector that measures the SD distance of 15 mm is provided at AS1, among three lighting timings, the light source is turned off two times.

In the above description, even though a device that uses a lock-in detecting method is supposed, in addition to the CDMA method, a time divisional detecting method that sequentially turns on the light sources at the respective lighting timings may be used. In the time divisional detecting method, only one light source is simultaneously turned on. Therefore, there is no need to consider the interference between the light sources at the time of detection and an average irradiating power for the subject 10 is lowered so that a peak power per one light source may be increased.

FIGS. 15 to 18 illustrate quadruple density probe arrangements A to D and arrangement of measurement points. The quadruple density probe arrangement A of FIGS. 15A and 15B is disclosed in Non-Patent Literature 6. In each drawing, "□", "■", "●", "X", "Δ", and "◇" indicate the optical transmitter 50, the optical receiver 60, a measurement point 11a in the SD distance of 30 mm, a measurement point 11b in the SD distance of 23.7 mm, a measurement point 11c in the SD distance of 15 mm, and a measurement point 11d in the SD distance of 10.6 mm, respectively. In any of probe arrangements in FIGS. 15 to 18, the arrangements of measurement points in the SD distance of 30 mm are same. In this case, the distance between the measurement points in the SD distance of 30 mm is 10.6 mm and a spatial distribution density of the measurement points is increased and the spatial resolution is also increased. Further, the number of usable SD distances is increased and the distribution density is increased so that it is effective in performing the method of separating and extracting the signals from the brain and the scalp. Further, since in addition to the SD distance illustrated in FIGS. 15 to 18, a measurement point may be obtained by combining the optical transmitter 50 and the optical receiver 60 likes an SD distance of 45 mm, the arrangement of measurement points including such a measurement point may be used. In this case, there is a need to appropriately set the lighting order of the light sources by the arrangement of the measurement points.

Figures 19A, 19B:
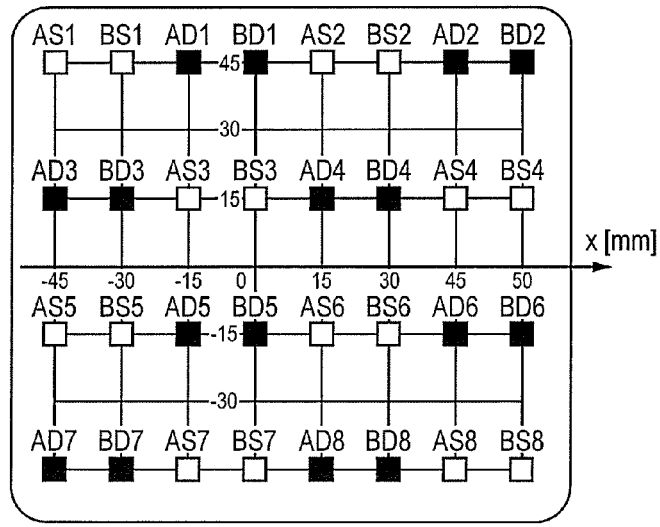
FIG. 19A is a view illustrating an example of a double density probe arrangement.
FIG. 19B is a view illustrating a set of used light source and detector in measurement points of the double density probe.

When the method of separating and extracting the signals from the brain and the scalp is performed, the SD distance which is uniquely determined by the pair of the optical transmitter 50 and the optical receiver 60 is stored by the memory part 108 of the biological photometric device of the present invention and thus the control and analysis part 106 needs to use the value to perform analysis. FIG. 19A illustrates a double density probe arrangement and FIG. 19B illustrates a set of used light source and detector at the measurement point available at that time. In FIG. 19B, "○" indicates a measurement point in the SD distance of 30 mm and "⊙" indicates a measurement point in the SD distance of 15 mm. A blank cell indicates that the measurement is not performed in the combination of the corresponding light source and detector and thus is unused. The correspondence relationship is input by the input part 107 or read out from the memory part 108.

FIG. 20 illustrates a setting screen of the probe arrangement and the SD distance. In the setting screen, setting lists are input from a key board or a mouse included in the input part 107. In a combo box 110 that selects the probe arrangements, the probe arrangement is selected. For example, an arrangement with four optical transmitting/receiving probes in a vertical direction and eight optical transmitting/receiving probes in a horizontal direction (4×8) and an arrangement with three optical transmitting/receiving probes in a vertical direction and ten optical transmitting/receiving probes in a horizontal direction (3×10) are displayed as an example. In these arrangements, since the positions of the measurable measurement points or the SD distance are determined in advance, there is no need to input the SD distance and the like. If "Other" is selected or a SD distance or the combination of the light source and detector to be used in the probe arrangement of "4×8" or "3×10" is manually set, the following selection is performed using a radio button 111 for SD distance setting. In the "manual setting", both the combination of light source and detector to be used and the SD distance are manually set. In the "automatic setting", both the combination of light source and detector to be used and the SD distance are automatically set. In this case, for example, it is set to measure all measurement points in SD distances of approximately 10 to 40 mm. In "auto setting of only SD distance of 30 mm", among all combinations of light source and detector, only the SD distance of 30 mm is automatically set to be used and the others may be manually set. "Set used SD distance" will be described with reference to FIG. 21. When the combination of light source and detector to be used and the SD distance are manually set, the setting is available by inputting numbers in a cell 112 for inputting the SD distance. If an experimenter stores the setting conditions, the experimenter presses an OK button 113. In contrast, if the experimenter does not store the setting conditions, the experimenter presses a cancel button 114. In the example, even though the SD distances of 30 mm and 15 mm are displayed, the control and analysis part 106 may automatically calculate all SD distances of the optical transmitter 50 and the optical receiver 60 to display the SD distances in the cell. In this case, in the setting screen of FIG. 20, by adding "use" and "no use" buttons, use or no use of a cell corresponding to each of the measurement points may be set on the screen.

Figure 21:
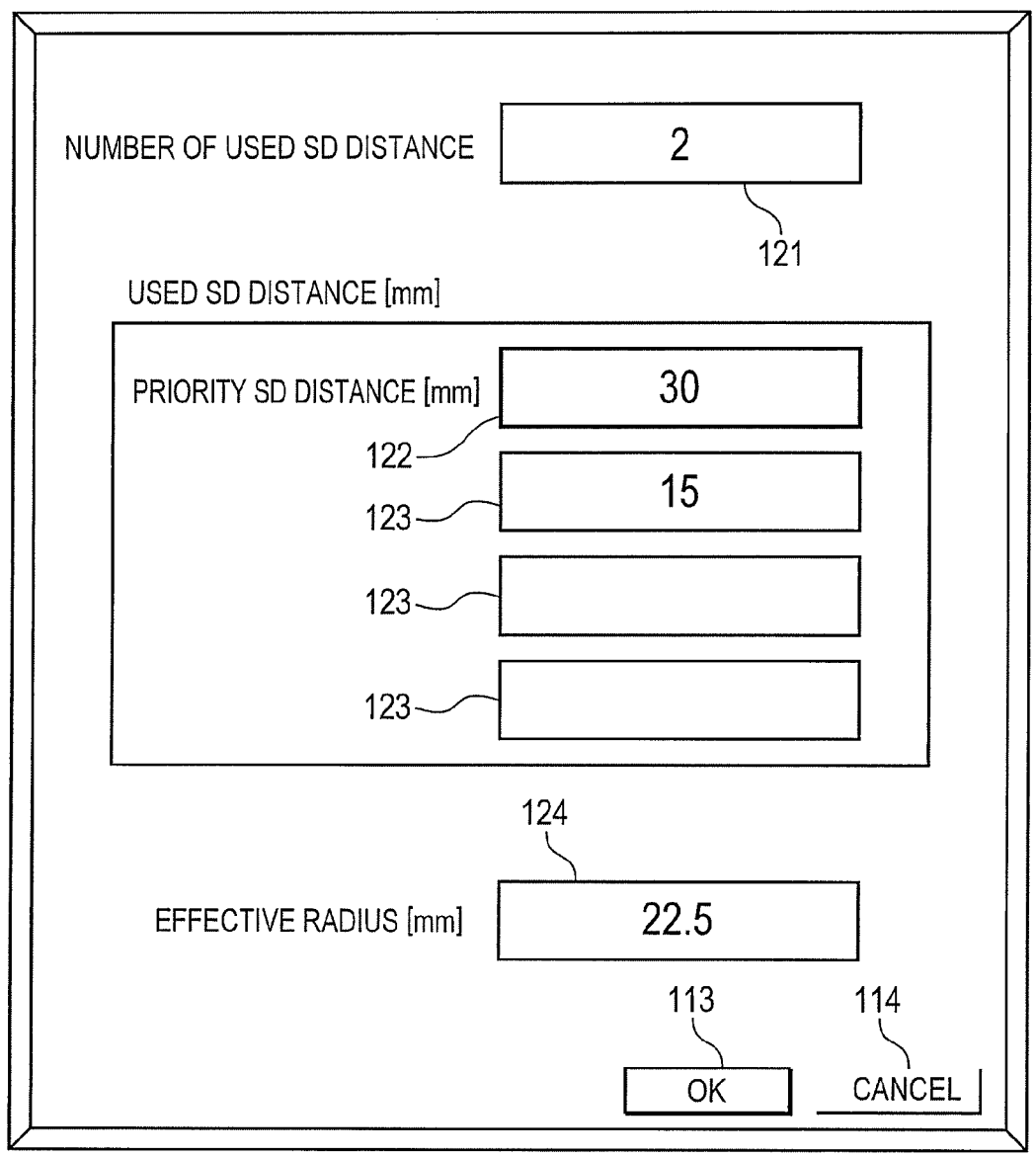
FIG. 21 is a view illustrating a setting screen of a used SD distance and an effective radius.

FIG. 21 illustrates a setting screen of the used SD distance and an effective radius. Since plural kinds of SD distances are considered from the probe arrangement which is actually used, the setting screen is provided so as to select a used SD distance among the plural SD distances. In a text box 121, the number of kinds of used SD distances is input. In text boxes 122 and 123 in which the used SD distances are input, a priority SD distance and the other SD distances are input, respectively. In the text box 124, an effective radius is input. Here, all measurement points of priority SD distances are measured. At the measurement point in the priority SD distance, the signal from the brain and the signal from the scalp are separated and reconstructed. A used distance range from the measurement point of the priority SD distance of the used SD distances other than the priority SD distance is input to the text box 124 of the "effective radius". Further, all measurement points of the SD distances within the effective radius in the text box 123 are used. By the method, the SNR at all measurement points is allowed to be in a predetermined range and the priority SD distance is set so that the analysis and the display are allowed in accordance with the purpose. In addition, according to the system, since the measurement points to be used are selected and used without omission, it is possible to precisely perform the method of separating and extracting the signal from the brain and the signal from the scalp with a high reproducibility. The OK button 113 and the cancel button 114 are used similarly to FIG. 20.

Figure 22:
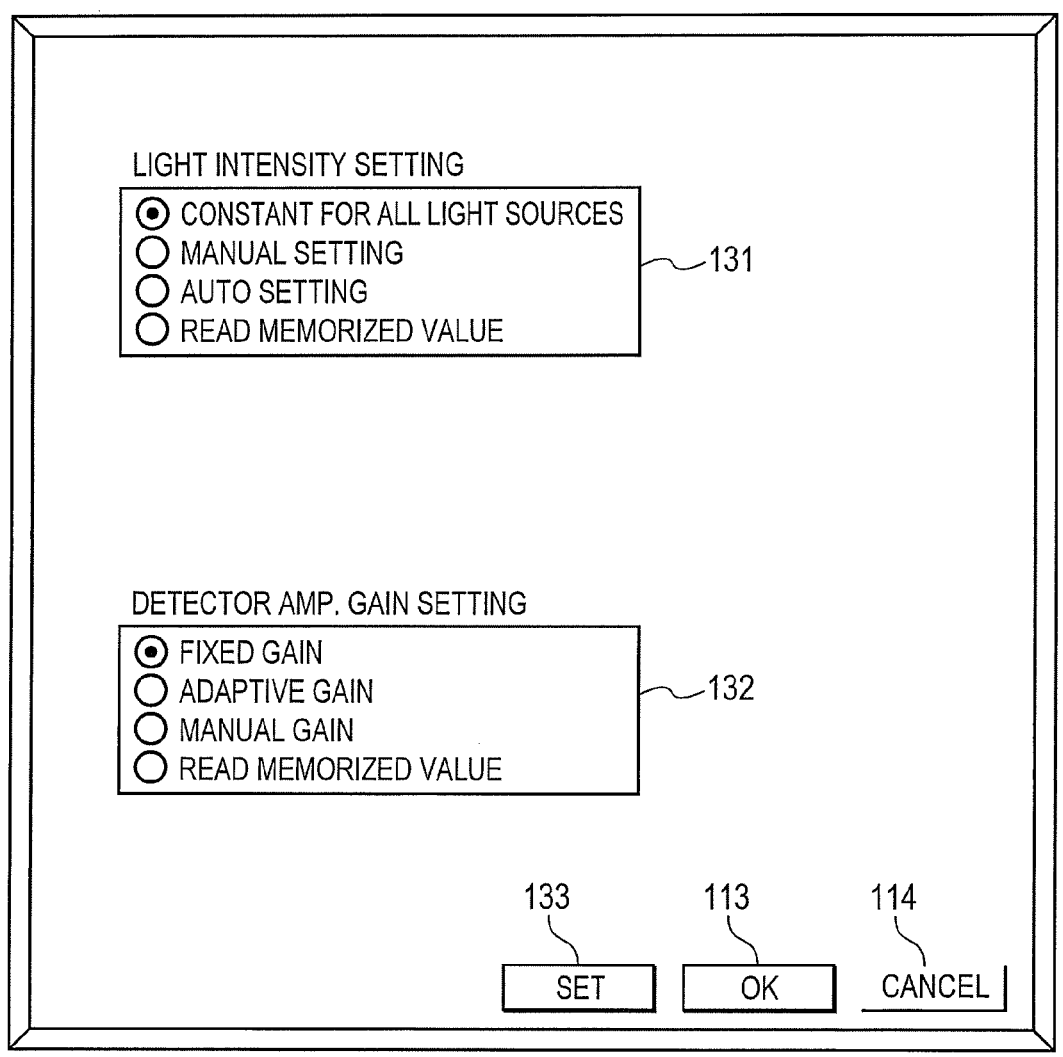
FIG. 22 is a view illustrating a setting screen of a light intensity and a gain of a detector.

FIG. 22 illustrates a setting screen of a light intensity and a gain of the detector. An operator sets the light intensity and the gain of the detector using the input part 107. The light intensity is set in following four setting modes by a radio button 131 that sets the light intensity. In "constant for all light sources" mode, the light intensity is set for all light sources to be constant. For example, the mode is used when a temporal average is constantly maintained due to restriction such as a safety criterion. In a "manual setting" mode, a light intensity of each of the light sources is manually set one by one. In an "automatic setting" mode, the light intensity of each of the light sources is automatically set. In this case, the light intensity is set so as to avoid the saturation of the detector, maintain the light intensity to be below a predetermined threshold value, or maximize the signal to noise ratio (SNR). The threshold value is, for example, set to be 3 mW which is below the safety criterion. In a "read memorized value" mode, a memorized value of a previous setting value is used.

By the radio button 132 for setting the gain of the detector, the gain of the detector is set in following four modes. In a "fixed gain" mode, the gain set in the detector is temporally constant. For example, the gain is set to be half the level where the detector is saturated so as not to be saturated at an irradiating timing with the largest detected light intensity. In an "adaptive gain" mode, an optimal gain is set at irradiating timing of each of the light sources. In a "manual gain" mode, the gain of each of the light sources is manually input and set. In a "read memorized value" mode, a memorized value of a previous setting value is used. In these setting modes, the setting button 133 is pressed so that the setting condition is effective. When the setting condition is stored, the OK button 113 is pressed. When the setting condition is not stored, the cancel button 114 is pressed.

By changing the setting of the light intensity and the gain of the detector, the measurement conditions are optimized in the measurement at various probe arrangements and SD distances and the conditions may be unified for every subject. Further, the reproducibility may be improved for the same subject.

Figure 23:
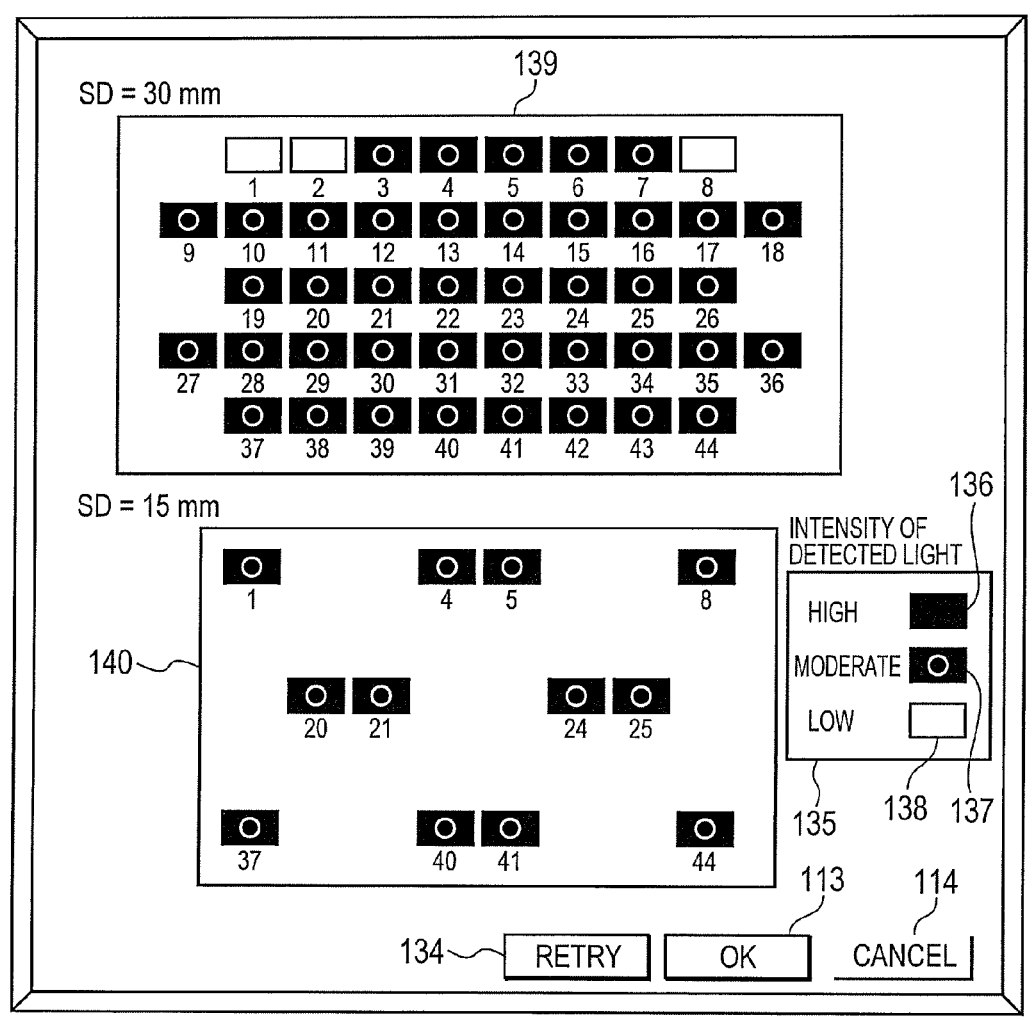
FIG. 23 is a view illustrating a detector gain automatic adjusting screen.

FIG. 23 illustrates a detector gain automatic adjusting screen. In the detector gain condition set in FIG. 22, in cases of "fixed gain" setting or the "adaptive gain" setting, the gain of the detector is automatically adjusted. The automatic gain setting result 139 at the measurement point in the SD distance of 30 mm is illustrated on an upper part of the screen, and the automatic gain setting result 140 at the measurement point in the SD distance of 15 mm is illustrated on a lower part of the screen. An indication method is as illustrated in a legend 135. An indication 136 indicating that an intensity of the detected light is high by coloring the cell of the measurement position with black, an indication 137 indicating that the intensity of the detected light is moderate by coloring the cell of the measurement position with gray with a circle (○) at a center thereof, and an indication 138 indicating that the intensity of the detected light is low by coloring the cell of the measurement position with white are used. Since the result of the intensity of the detected light largely depends on a mounted state of the probe, when the intensity of detected light is low at some of measurement points, the probe is fixed to be mounted to improve the intensity. In this case, after changing the mounted state of probe, a retry button 134 of the gain adjustment is pressed to adjust the gain of the detector again.

Figure 24:
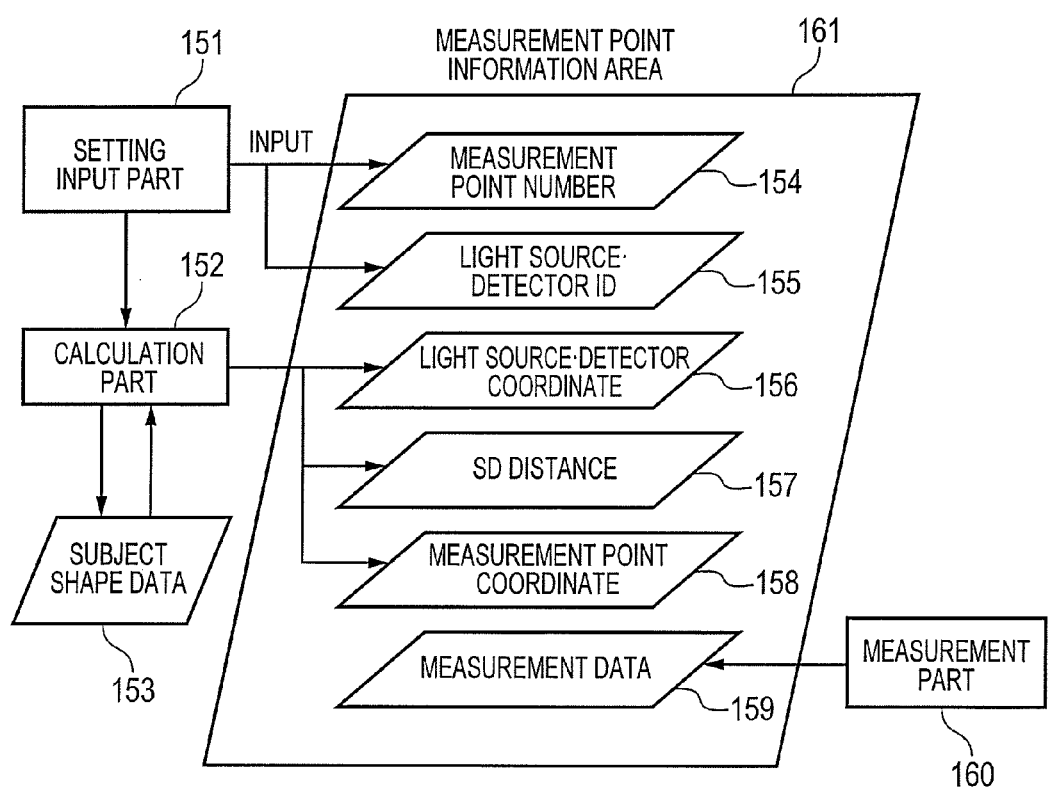
FIG. 24 is a view illustrating data structure of measurement point information.

In order to apply the method that separates and extracts the signal from the brain and the signal from the scalp to a broader measurement, the method may be desirably applied for all probe arrangements. Therefore, various information for each of the measurement points is stored in database and then the information is used at the time of analysis to efficiently separate and extract the signal from the brain and the signal from the scalp. FIG. 24 illustrates data structure of measurement point information. In a measurement point information region 161, six kinds of information, that is, a measurement point number 154, a light source/detector ID 155, a light source/detector coordinate 156, an SD distance 157, a measurement point coordinate 158, measurement data 159 are stored. The measurement data 159 is data which is stored by being sent from a measurement part 160. An operator of experiment inputs a pair of optical transmitter and optical receiver to be used, arrangement of the optical transmitter and the optical receiver, a positional reference with respect to the subject, and a number of the measurement point using a setting input part 151. Here, the positional reference adopts, for example, an international 10-20 rule used to dispose brain wave electrodes as a reference. Based on the input information, data corresponding to the measurement point number 154 and the light source/detector ID 155 in the measurement point information region 161 is input. Further, the light source/detector coordinate 156, the SD distance 157, and the measurement point coordinate 158 are calculated by a calculation part 152 and then stored as data. Further, at the time of calculation, a subject shape data 153 is read to be used. The subject shape data 153 includes, for example, head shape data by a nuclear magnetic resonance imaging (MRI) or an X ray CT or head shape data of the subject which is measured by a three dimensional position measurement system that uses magnetism.

Figure 25:
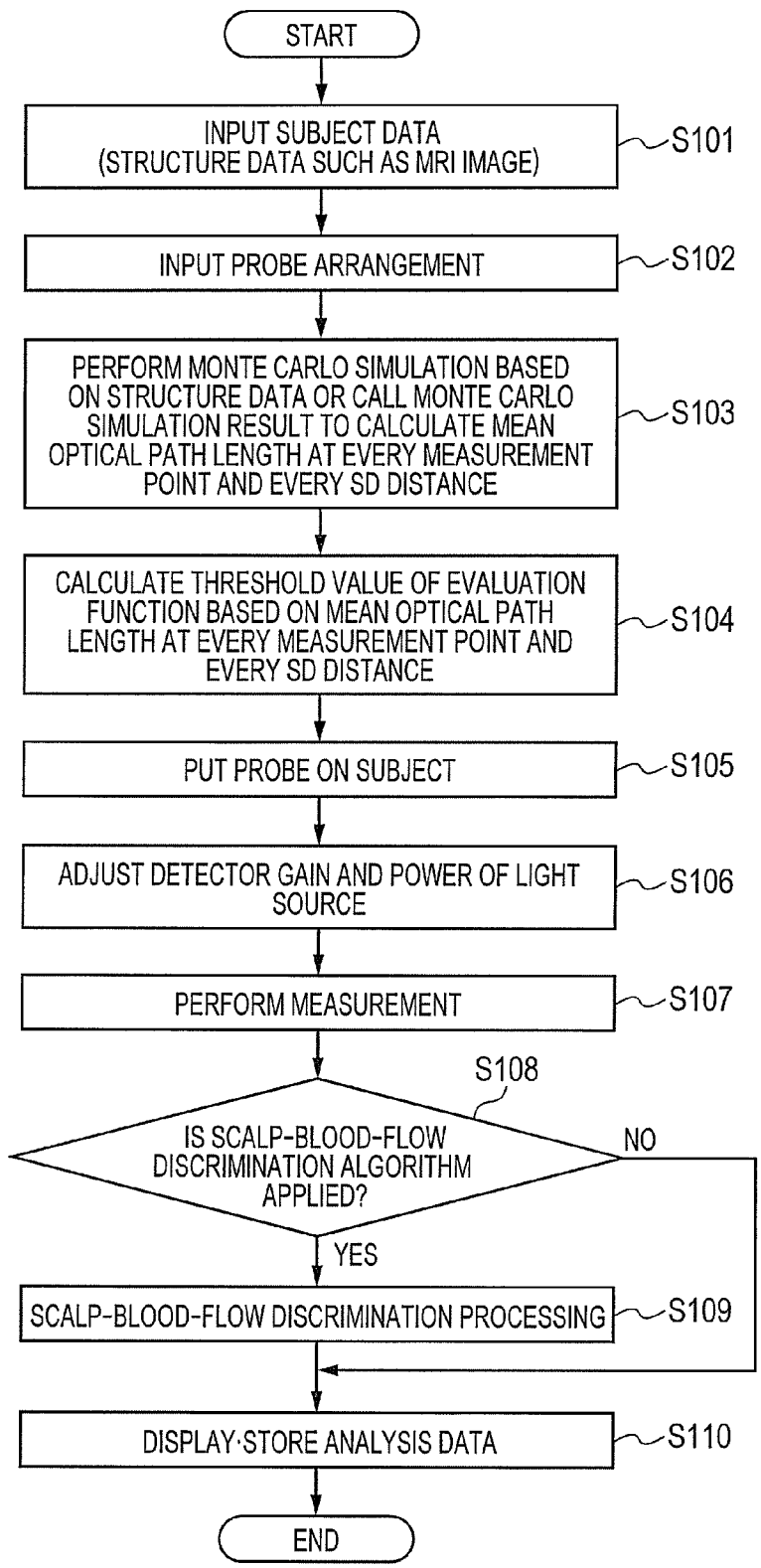
FIG. 25 is a view illustrating a measurement flowchart.

A flow of the measurement in the embodiment will be described. FIG. 25 illustrates a measurement flowchart in the embodiment. At first, the operator inputs subject data (structure data such as an MRI image) (S101). Then, the operator inputs probe arrangement (S102). The calculation part 152 performs Monte Carlo simulation based on the structure data or calls a Monte Carlo simulation result and calculates a mean optical path length at every measurement point and every SD distance (S103). The calculation part 152 calculates a threshold value of an evaluation function (for example, a gradient of weight values with respect to the SD distance) based on the mean optical path length at every measurement point and SD distance (S104). Next, the operator mounts the probe on the subject (S105) and adjusts a detector gain and power of a light source (S106) and performs the measurement (S107). Next, the calculation part 152 determines whether a scalp blood flow discrimination algorithm is applied (S108). If the algorithm is applied, the scalp blood flow discrimination processing is performed (S109) and then the analysis data is displayed and stored (S110). If the algorithm is not applied, the analysis data is displayed and stored (S110) without performing the scalp blood flow discrimination processing (S109). As described above, by using an optimal threshold value to the subject which is calculated and estimated from the structure data, it is possible to improve the precision of the scalp blood flow discrimination algorithm. Further, even when the structure data is not provided, it is considered to use the same value for every subject as a threshold value calculated from an experimental value of the threshold value or a threshold value calculated from standard human head structure data. In this case, the threshold may be selected between 0.0015 and 0.0055 mMmm/mm.

As a method that optimizes a threshold value of a weight value gradient with respect to the SD distance for every subject, there is a method that calculates an optical path length based on the head structure data of each subject on the basis of the Monte Carlo simulation or numerical analysis by an optical diffusion equation and determines an optimal threshold value so as not to be contradictory with the result. However, the head structure data requires MRI or X ray CT measurement data and it is not sure if the head structure data is available for all subjects. Therefore, other method is required. In this case, a method that temporally sets the threshold value to approximately 0.0015 to 0.0055 mMmm/mm and performs measurement for the same subject in the same task several times and searches for the threshold value separated into the brain component and the scalp component for every time or as many times as possible is considered. According to the method, since a subject dependent factor is considered by selecting a threshold value having a high reproducibility of the separation result, the method may be a robust method as compared with a method that uses a fixed threshold value.

Figure 26:
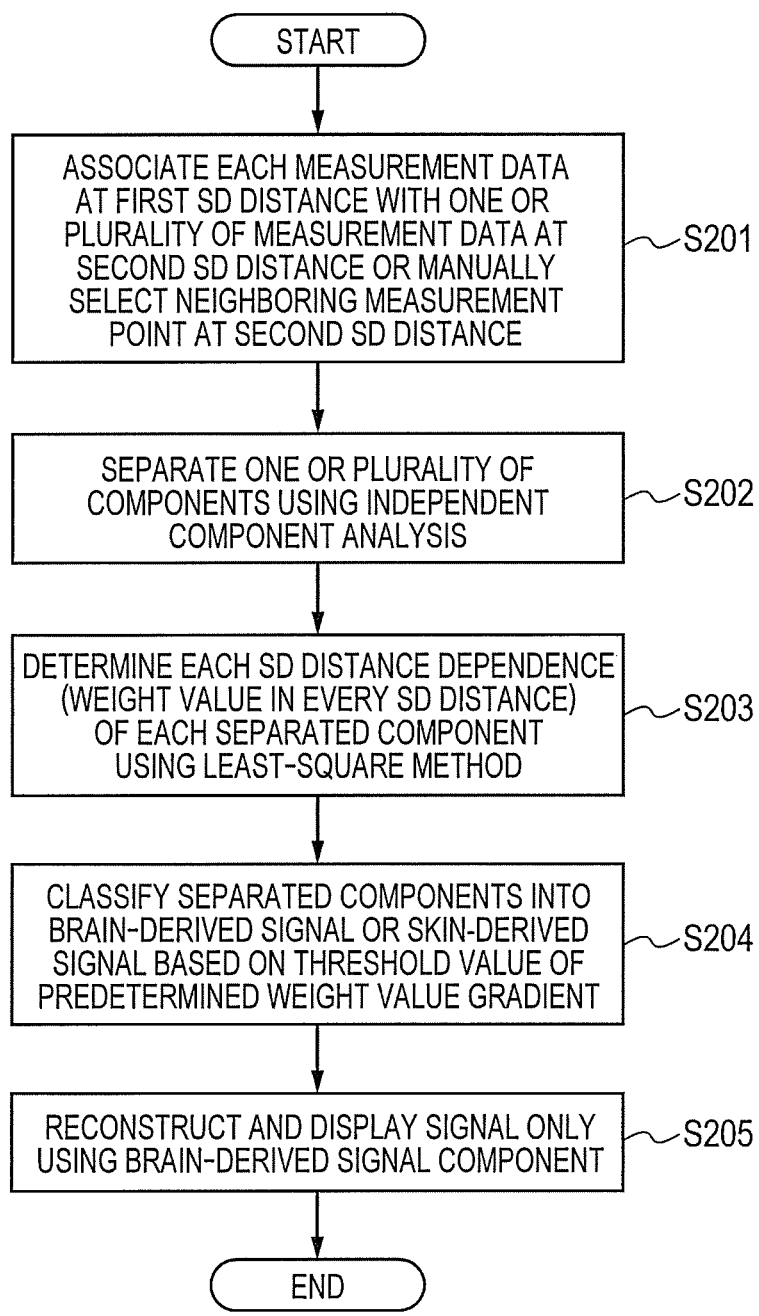
FIG. 26 is a flowchart of scalp blood flow discrimination.

FIG. 26 illustrates a flowchart of scalp blood flow discrimination. At first, the calculation part 152 associates one or a plurality of measurement data at a second SD distance with each measurement data in a first SD distance. Alternatively, the operator manually selects a neighboring measurement point at the second SD distance (S201). Next, the calculation part 152 separates one or plurality of components using a signal separating method such as independent component analysis (S202) and determines SD distance dependency (weight value gradient in every SD distance) of the separated components using a least-square method (S203). The calculation part 152 classifies the separated components into a signal from brain or a signal from the scalp based on a predetermined evaluation function (S204). Finally, the calculation part 152 reconstructs a signal only using the signal component from the brain to be displayed (S205).

In the flowchart, only independent component analysis has been described. However, a signal separating method that applies principle component analysis, factor analysis, multiple linear regression analysis, or cluster analysis may be used. Further, when the calculation part 152 calculates the dependency on the SD distance of the separated components, a model equation is not limited to a linear function, but may be a method that performs a least square fitting on an appropriate order of polynomial equation, an exponential function, a logarithm function, or a hyperbolic function. Further, for the evaluation function described above, the weight value gradient of an independent component, a threshold value by the Monte Carlo simulation which can be calculated from an assumption of the structure data, or a value obtained by subtracting error sum of square at the time of fitting from the weight value gradient may be used. In other words, if the error sum of square is large, the reliability of the separated component is considered to be low. Therefore, the separated component is considered as a noise or a systemic signal component so that the separated component is not separated as a brain component. Accordingly, the component is removed, which allows only an appropriate separated component as a brain component to be extracted.

Further, other than the method of calculating the evaluation function as described above, if there is a plurality of data in the same SD distance when the weight value gradient of the independent component is calculated, a method that calculates a standard deviation using a weight value of the SD distance and calculates a gradient by weighting a reciprocal number thereof is considered. The method is based on an assumption that the value is probable as the standard deviation of the weight value is small. If the variation is large, a possibility that the value is obtained by chance is high. Therefore, according to the method, since the evaluation function is calculated to be low, a probability that the component is separated as the brain component is lowered. As described above, a component having a variation in the weight values even in the same SD distance may be removed from the brain component.

As another method of calculating an evaluation function, a method that considers a reciprocal number of a distance of a priority SD distance from the measurement point as a reliability to be weighted and calculates the weight value gradient using data of the measurement points in every SD distance is considered. If the measurement point is deviated, an optical path of light irradiated from the optical transmitter 50 is changed so that a possibility that a wrong part is measured is increased. Therefore, as closer to the measurement point in the priority SD distance, the optical path shared at the measurement points is increased, which becomes a proper condition to calculate the independent component by the independent component analysis. According to the method, it is possible to weight depending on the distance between the measurement points even when the distribution range of the scalp blood flow is small and the measurement wave is varied depending on the position of the measurement point. Therefore, it is possible to obtain a more precise result.

Further, a method that uses an intercept of an SD distance axis (X axis in FIG. 4B) of the regression line that indicates the SD distance dependency of each of the independence component obtained by the least-square method is considered. For example, in the case of an independence component having a large intercept of the SD distance axis, the weight value is increased when the SD distance is equal to or larger than a predetermined value. Therefore, the component may be from a hemodynamic status of a deep portion of the gray matter. Accordingly, a method that sets a threshold value in the intercept of the SD distance axis (X axis) is considered. According to a Modified Beer-Lambert law, a signal which is proportional to the optical path should be obtained (if a uniform change of blood flow in the corresponding partial optical path is assumed). Therefore, if an independence component is a signal from the gray matter, the X intercept of the regression line that represents the SD distance dependency is expected to be ideally approximately 10 mm and at least positive. Since the x intercept does not depend on the signal amplitude, the x intercept does not have task dependency and thus may be a threshold value which may be commonly used for the same subject.

For example, as illustrated in FIG. 4B, the threshold value of the x intercept may be set to be approximately 10 mm. By doing this, signals from the tissue in a shallow portion and a deep portion in the subject 10 may be precisely separated. Further, by combining the threshold value of the x intercept with the weight value gradient described above, it is expected to increase the precision.

Further, if the x intercept is approximately 10 mm or less and, specifically, has a negative value, in an ideal case that does not include a noise, a signal of a shallower portion than the gray matter is included. If the gradient is large simultaneously to the above, a signal of a deep portion including the gray matter is included. Therefore, it is interpreted that the component is commonly included in the deep portion and the shallow portion. For example, systemic hemodynamic component may be commonly included in both the deep portion and the shallow portion. As described above, by studying the x intercept and the gradient, it is possible to determine whether the component is included in only one of the deep portion or the shallow portion or both the deep portion and the shallow portion.

Figure 27:
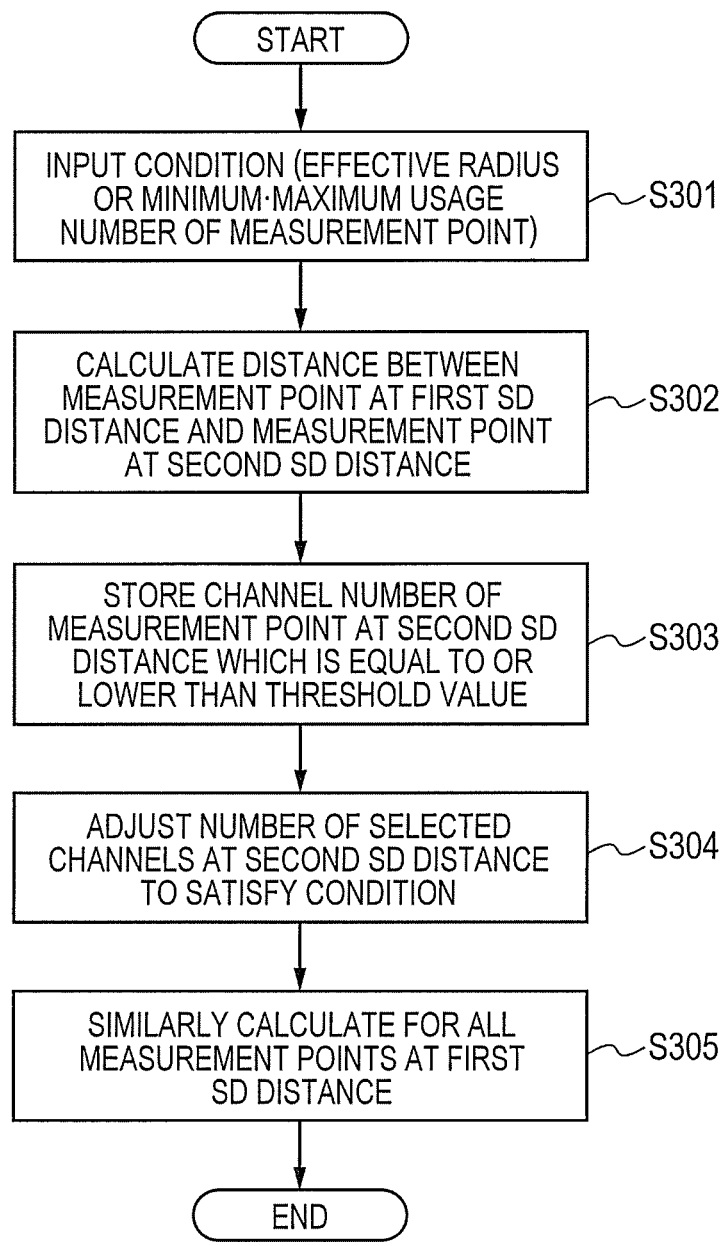
FIG. 27 is a flowchart of selecting a measurement point in a second SD distance corresponding to a measurement point in a first SD distance.

If a plurality of optical transmitters 50 and a plurality of optical receivers 60 are provided, as illustrated in FIG. 21, for example, independent component analysis is performed using a measurement point in the SD distance of 15 mm which is disposed within an effective radius of 22.5 mm with respect to the measurement point in each of the SD distances of 30 mm (priority SD distance). In the independent component analysis, in order to extract a plurality of independent components, data at a plurality of measurement points is required in principle so that it is required to select the used data. A flow when a measurement point to be used in the independent component analysis is selected corresponding to the measurement point in each of the priority SD distances will be described below. FIG. 27 is a flowchart of selecting a measurement point in the second SD distance corresponding to a measurement point in each of the first SD distances. At first, the operator inputs a condition such as an effective radius or minimum and maximum number of used measurement points (S301). Next, the calculation part 152 calculates a distance between the measurement point in the first SD distance (priority SD distance) and the measurement point in the second SD distance (S302) and stores a channel number of the measurement point in the second SD distance which is equal to or smaller than the threshold value (may be smaller than the threshold value) (S303). The calculation part 152 adjusts the number of selected channels at the second SD distance so as to satisfy the condition (S304). The calculation part 152 similarly calculates the above steps for all measurement points in the first SD distance (S305). By the flow, only the neighborhood measurement point is included in the analysis. If the scalp blood flow does not have a broad spectrum, that is, even when the scalp blood flow is locally distributed, only the neighborhood measurement point which has a measurement point with the priority SD distance on the head surface as a center is used to extract the independent component. Therefore, it is possible to efficiently separate and remove the scalp blood flow component. Even when the scalp blood flow has a broad spectrum, it is needless to say that the scalp blood flow component is similarly separated and removed. Therefore, the method is more general than a method that removes the scalp blood flow based on a measurement signal of a laser Doppler blood flowmeter or a blood pressure meter other than the brain function.

Figure 28:
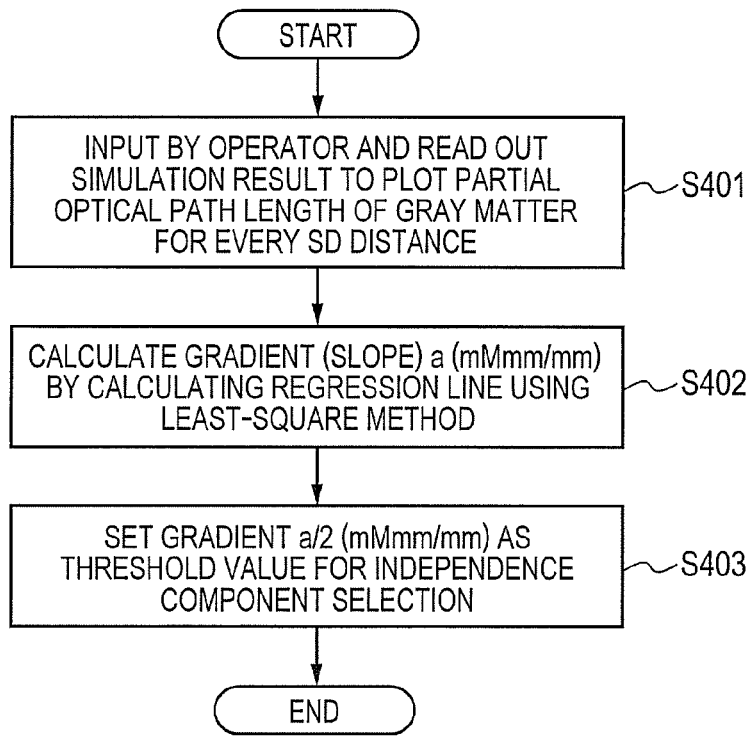
FIG. 28 is a flowchart of determining a threshold value of a weight value gradient of independent components in an SD distance.

FIG. 28 illustrates a flowchart of determining a threshold value of the weight value gradient of each of the independent components in a SD distance. At first, by inputting by the operator and the reading out of the simulation result, the calculation part 152 plots a partial optical path length of the gray matter for every SD distance (S401). Next, the calculation part 152 calculates the gradient (slope) a (mMmm/mm) by calculating a regression line using the least-square method (S402) and sets, for example, an amount a/2 (mMmm/mm) uniquely defined from the gradient a (mMmm/mm) as a threshold value for the independent component selection (S403). Here, in order to separate the scalp signal and the gray matter signal illustrated in FIG. 4, an average of the gradients with respect to the SD distance of both signals is defined as a threshold value. Further, the threshold value is not limited to a/2, but may be defined as a different value. By the method, an optimal threshold value which depends on the head structure of each of the subjects may be used so that it is possible to precisely separate the brain component and the scalp component.

Further, a measurement point in a short SD distance may be smoothly present within the effective radius to be close to the measurement point in the priority SD distance. However, it is also considered that the measurement point in a short SD distance does not exist depending on the probe arrangement, which is because the distribution density of the measurement points in each of the SD distances is varied. In this case, an exceptional processing that increases the effective radius of the measurement point in the priority SD distance around which there is no measurement point in a short SD distance and uses data of the nearest measurement point in the short SD distance is required.

Figure 29:
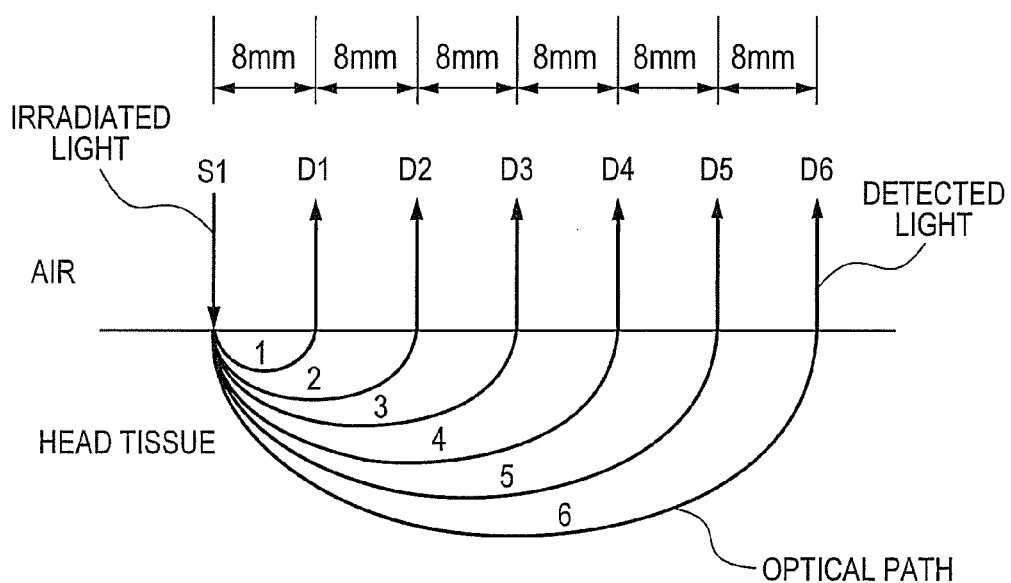
FIG. 29 is a view illustrating a multiple SD distance probe arrangement having one optical transmitter and six optical receivers.

Next, an actual measuring example that uses the present invention will be described. In order to confirm the basic principle of the present invention, a probe including one optical transmitter 50 and six optical receivers 60 is used to measure a human left frontal region at the time of performing a verbal working memory task. FIG. 29 illustrates a multiple SD distance probe arrangement having one optical transmitter and six optical receivers. The optical receivers 60 are disposed on a straight line with an interval of 8 mm. In the verbal working memory task, the subject memorizes two or four Hiragana which is displayed on a target screen for 1.5 seconds and judges whether Hiragana which is pronounced alike to one Katakana which is displayed in the probe screen after a delay period of seven seconds is present in the memorized screen as soon as quickly. If Hiragana is present, the subject presses "○" button and if not, the subject presses "X" button. The used button is in a game pad. When the button is pressed, the probe screen disappears. However, even when the button is not pressed, the probe screen disappears for at most two seconds. After displaying the probe screen, a rest time of 16 to 21 seconds is provided. During the delay period after the target screen and the rest period after the probe screen, a fixation point is displayed on the screen and the subject gazes the fixation point. One second immediately before displaying the target screen and one second between 14 second and 15 second after starting to display the probe screen are used to calculate a base line in each block. The sequence is repeated 16 times (total 16 trials).

Figure 30:
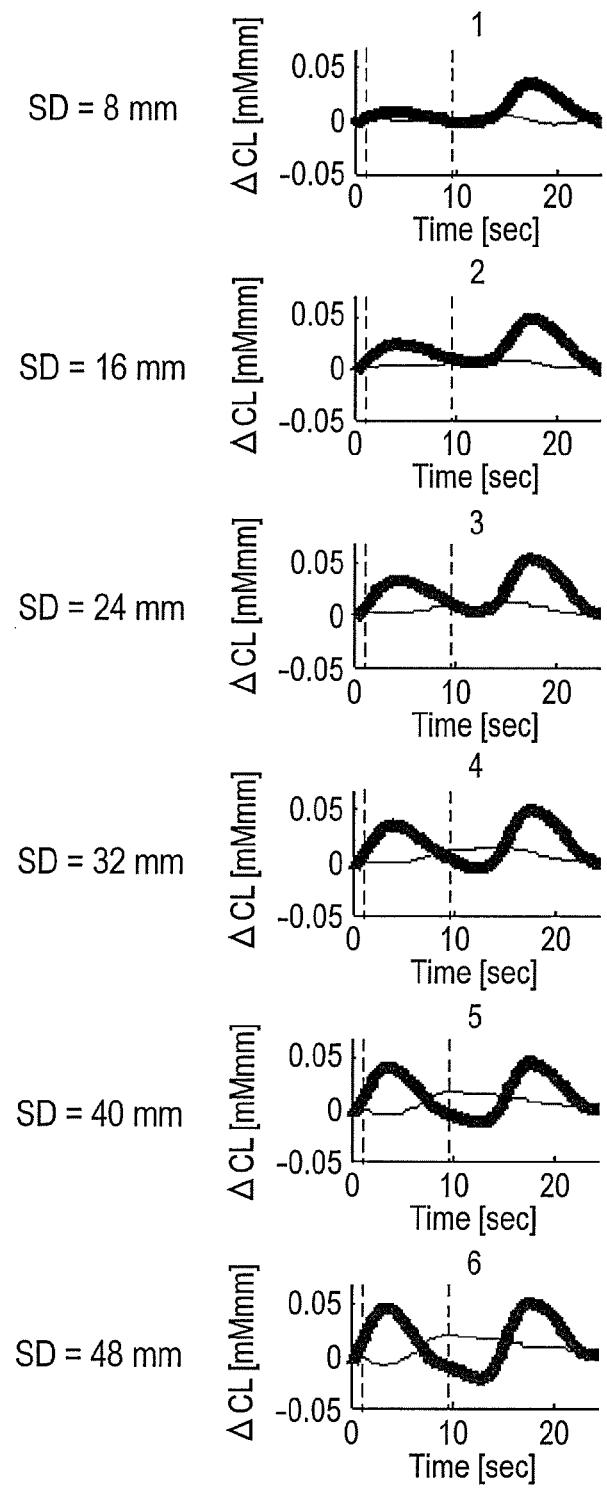
FIG. 30 is a view illustrating measurement data at each SD distance at the time of performing a verbal working memory task.

FIG. 30 illustrates measurement data in each of SD distances at the time of performing the verbal working memory task. The SD distances are 8, 16, 24, 32, 40, and 48 mm from the upper part. A dotted vertical line in the drawing is a mark indicating a starting/ending time of the task (t=1 s is a starting time). The bold lined waveform is a time change waveform of the oxygenated hemoglobin concentration length change (oxy-Hb) and a thin lined waveform is a time change waveform of the deoxygenated hemoglobin concentration length change (deoxy-Hb). Since the waveforms obtained in accordance with the SD distances are significantly different, it is considered that different hemodynamic changes occur in the shallow portion and the deep portion of the head. Two mountains (peaks) are represented. The first mountain is increased as the SD distance is increased while the second mountain has a substantially constant amplitude regardless of the SD distance. The first mountain and the second mountain are independent components. Further, it is easily understood that the gradient of the first mountain with respect to the SD distance of a product of the weight value and the root mean square is large but the gradient of the second mountain is small.

Figure 31:
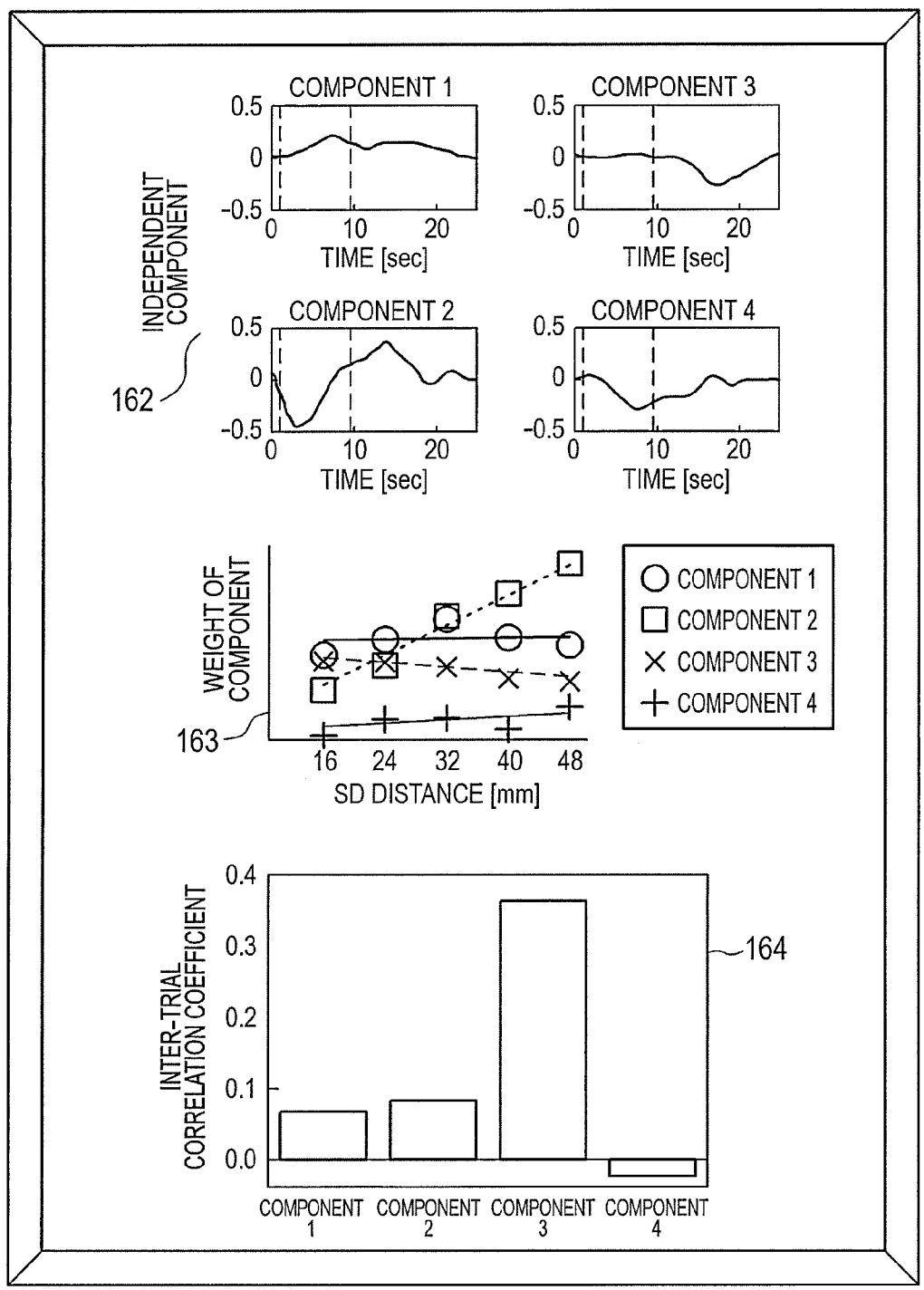
FIG. 31 is a view illustrating an extracted independent component, a weight value gradient, and an average of inter-trial correlation coefficients.

FIG. 31 illustrates an extracted independent component 162, a weight value gradient 163, and an average of an inter-trial correlation coefficients 164. Here, data of the SD distance of 8 mm is used to extract the independent component but not used to calculate the weight value gradient. As illustrated in FIG. 4B, if the SD distance is 10 mm or shorter, a partial mean optical path length in the gray matter is substantially 0 mm. Therefore, it is considered that if the data of the SD distance of 10 mm or shorter is used, the precision may be deteriorated. As a result, total four independent components are extracted and the component weight value gradient with respect to the SD distance of the components is as illustrated in the middle of FIG. 31. A gradient of a component 2 is large. Further, in the lower part of FIG. 31, an average value of the correlation coefficients of all combinations of the independent components during total 16 trials is illustrated, which indicates a strength of task synchrony of the independent components. By the display method, it is possible to search the correlation between the component weigh value gradient and the inter-trial correlation and the method is useful to search the task dependency of the brain component and the scalp blood flow.

Figure 32:
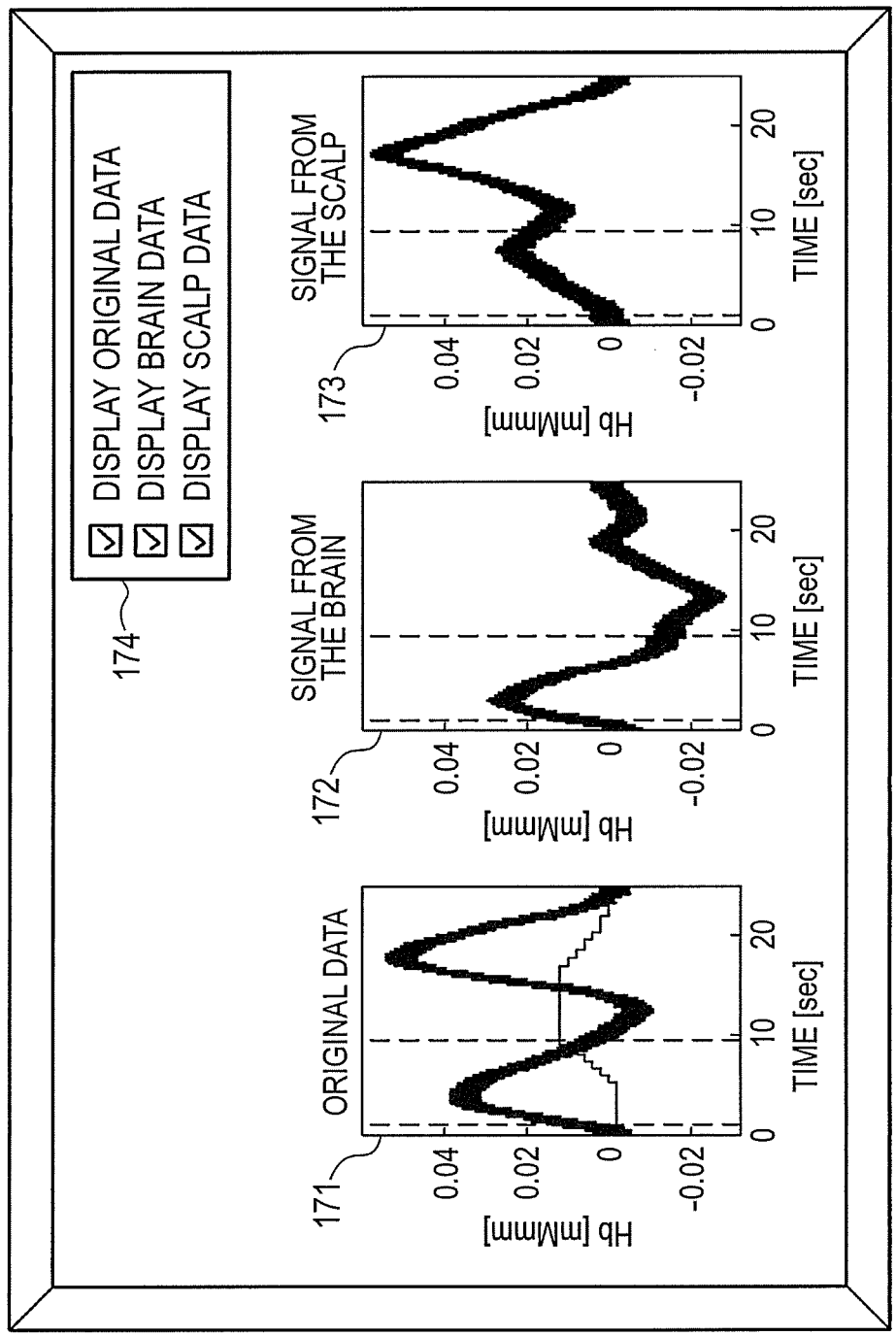
FIG. 32 is an example of result display of original data, a signal from the brain, and a signal from the scalp.

A result displaying example after separating the brain component and the scalp component by applying the method of the present invention is illustrated in FIG. 32. In FIG. 32, a result when the threshold value of the independent component is 0.0021 mMmm/mm is illustrated. In original data 171, the oxy-Hb and the deoxy-Hb measured in the SD distance of 32 mm are illustrated but the brain data 172 and the scalp data 173 are results that reconstruct only the oxy-Hb. This is because, in the experimental analysis, only oxy-Hb is used to separate the independent component. Here, data reconstructed as the brain data is a result reconstructed using only the component 2 in FIG. 31. The result has a positive-negative inversed waveform with respect to the waveform of the component 2, which is because the multiplied coefficient is negative at the time of reconstruction. In a check box 174 that selects a display method of the original data, the brain data, and the scalp data, data to be displayed may be selected and a display method in accordance with the purpose may be achieved. Even though not illustrated in FIG. 32, the SD distance of data to be displayed may be selected. Accordingly, a component having a larger amplitude is separated as a brain component and the other components are separated as the scalp data as the SD distance becomes longer. As described above, the original data 171, the brain data 172, and the scalp data 173 are simultaneously displayed with the same scale of the vertical axis so that it is possible to easily understand the state of the brain data or the scalp data included in the original data and the size of the contribution. Further, it helps to know the characteristics of the brain and scalp blood flow induced by the task.

Figure 33:
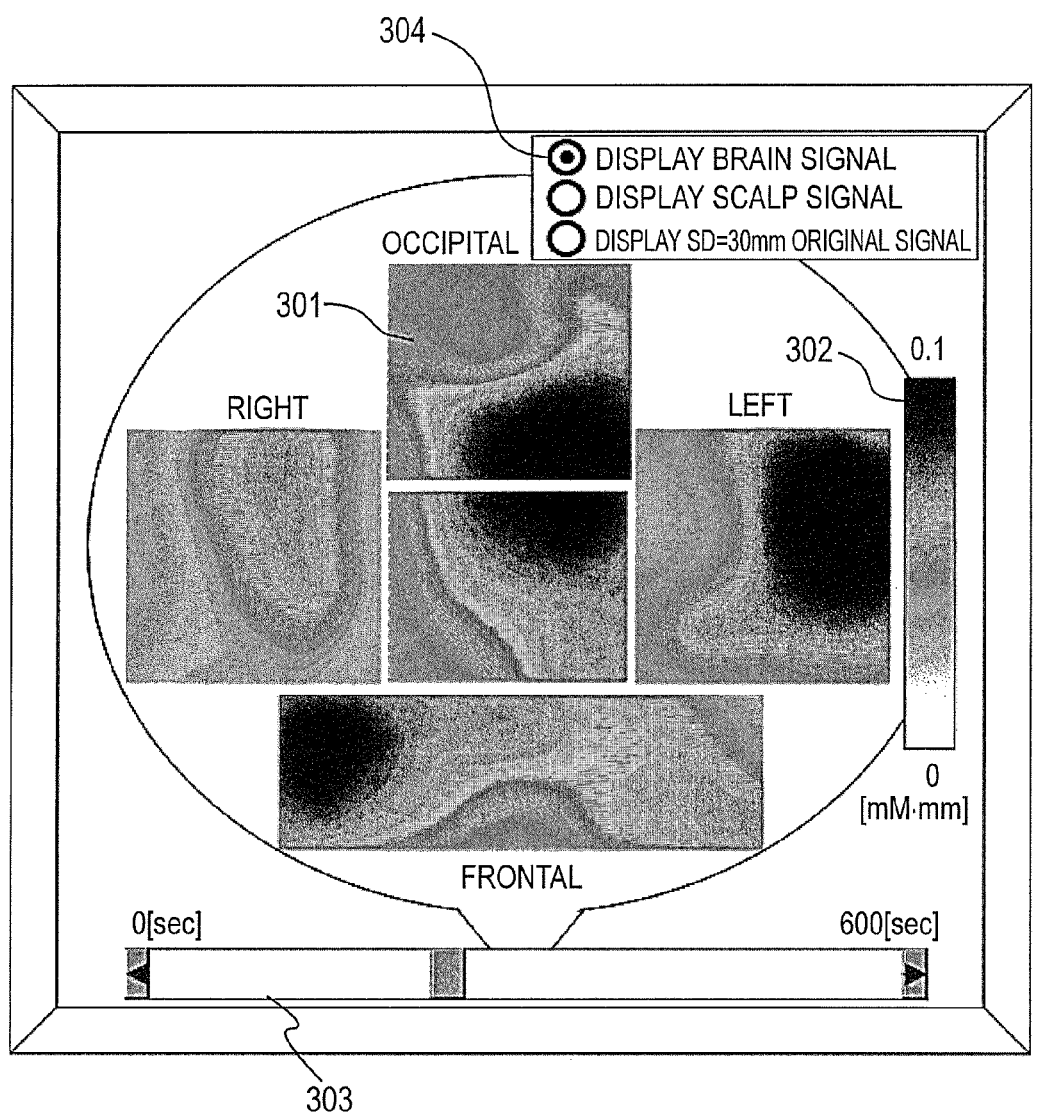
FIG. 33 is a display example of measurement result by a whole head measuring type brain function photometric device.
Figure 34:
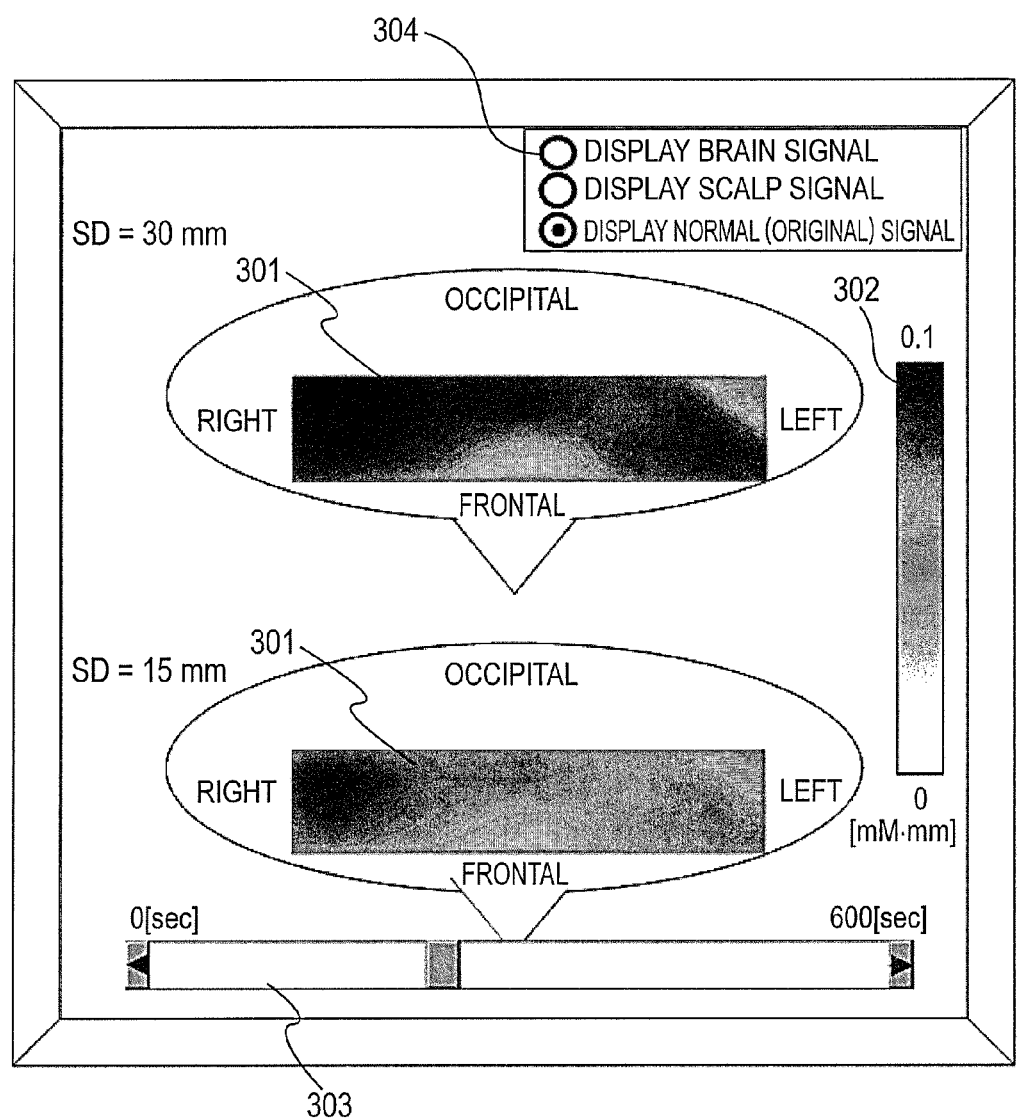
FIG. 34 is a display example of two dimensional data at every SD distance.

Next, a display example when the plurality of optical transmitters 50 and the plurality of optical receivers 60 are two-dimensionally disposed and the brain data and the scalp data are imaged to be measured is illustrated in FIG. 33. FIG. 33 is a display example of a measurement result by a whole head measuring type brain function photometric device. Oxygenated hemoglobin concentration length change (oxy-Hb) map 301 of a frontal region, a parietal region, a left and right temporal region, and an occipital region is displayed. An amplitude value is represented by shadings in a gray scale bar 302. A temporal axis may be adjusted by a scroll bar 303 for time display. Further, the radio button 304 allows the selecting whether to normally display the signal from the brain, the signal from the scalp, and the SD distance of 30 mm. Further, FIG. 34 illustrates a display example of two dimensional data at every SD distance. An upper portion of FIG. 34 illustrates original data (normal display) when the SD distance is 30 mm and a lower portion of FIG. 34 illustrates original data (normal display) when the SD distance is 15 mm. The radio button 304 allows the selection of the display method. As described above, by displaying the two dimensional measurement data for every SD distance, status of the signal from the brain and the signal from the scalp for every SD distance may be clearly understood.

In the display method in FIGS. 32 to 34, other than the original data, the brain data, and the scalp data, a component considered as a shared component included in both the deep portion and the shallow portion by the determination criterion of an x intercept may be simultaneously displayed.

Figure 35:
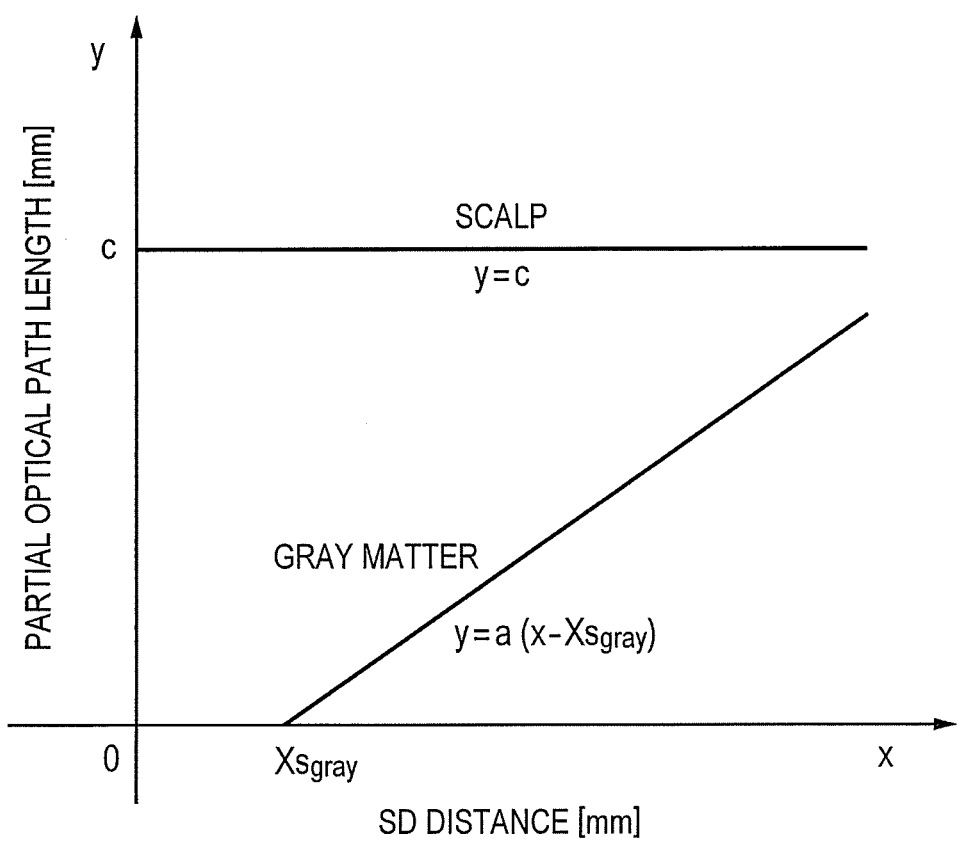
FIG. 35 is a view illustrating a model of a partial optical path length in the scalp and the gray matter.

Here, another method that classifies the brain data and the scalp data using the x intercept will be described. FIG. 35 illustrates a model of a partial optical path length in the scalp and the gray matter. The horizontal axis indicates the SD distance (mm) and the vertical axis indicates the partial optical path length (mm). In this case, if it is assumed that the scalp optical path length is a constant value and the gray matter is a straight line in which the x intercept is positive, a model may be obtained as represented by Equations 8 and 9.

[Equation 8]

$$y = c \qquad (8)$$

[Equation 9]

$$y = a(x - Xs_{gray}) \qquad (9)$$

Here, if a contribution ratio of the Hb concentration change in the brain (gray matter) in which optical path length influence of a "shared component" that contains both the signal from the brain and the signal from the scalp at a predetermined ratio is removed is t (0<t<1) (referred to as a brain contribution ratio) and a contribution ratio of a concentration change in the scalp (skin) is 1−t, a sum of optical path lengths of both signals weighted by t is represented by Equation 10.

[Equation 10]

$$y = a(x - Xs_{gray})t + c(1-t) \qquad (10)$$

Figure 36:
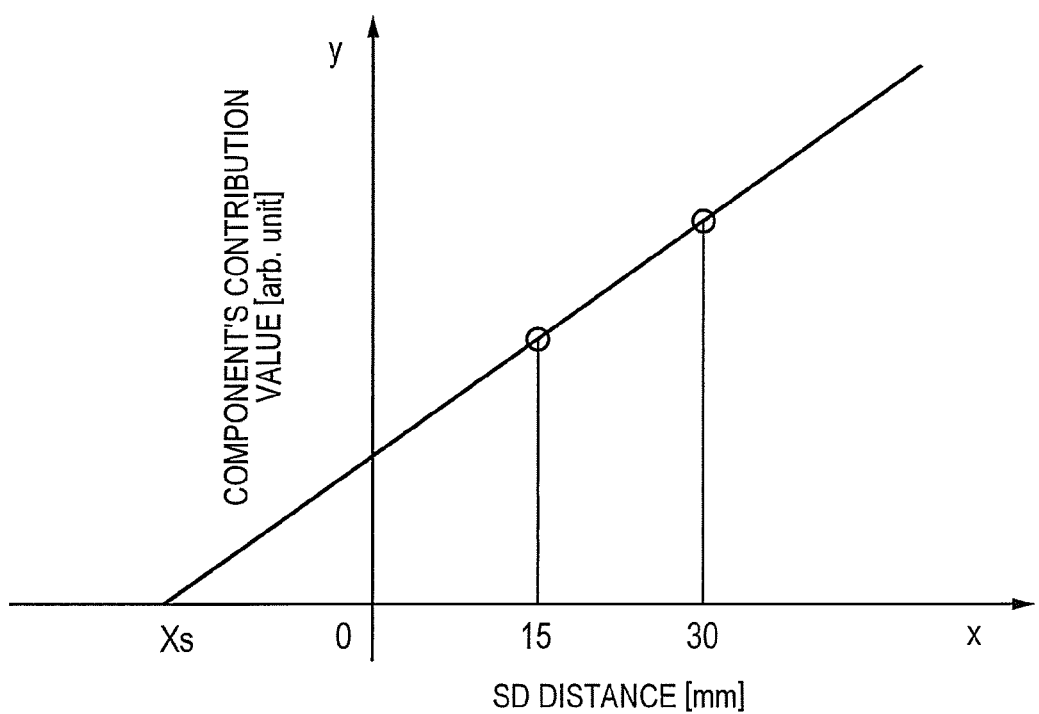
FIG. 36 is a view illustrating an example of an SD distance—component's contribution value distribution of a component which is shared by the scalp and the gray matter and a regression line thereof.

In this case, since a component's contribution value of the shared component at each measurement point is proportional to the optical path length, the component's contribution value is plotted with respect to the SD distance as illustrated in FIG. 36 (when using data of SD distances of 15 mm and 30 mm). In FIG. 36, the x intercept (Xs) is x when a left side of Equation 10 is substituted with 0 so that Xs is represented by Equation 11.

[Equation 11]

$$Xs = Xs_{gray} - \frac{c(1-t)}{at} \qquad (11)$$

Further, if Equation 11 is modified to be solved for t, Equation 12 is obtained.

[Equation 12]

$$t = \frac{c}{c - a(X_s - X_{s_{gray}})} = \frac{32.4}{41.4 - 0.833 X_s} \quad (12)$$

Here, it is assumed that a, Xs, and c are 0.833, 10.83, and 32.4, respectively from the Monte Carlo simulation result (FIG. 4) in which a typical human head model is assumed.

Therefore, the SD distance-component's contribution value distribution of the independent components from the actual measurement data is obtained and the x intercept (Xs) obtained by the linear regression by the least-square method is substituted in Equation 12 to obtain the contribution ratio t of the concentration change in the brain of the shared component. It is possible to reconstruct the shared component as a brain component and a scalp component by weighting with t and 1−t.

Figure 37:
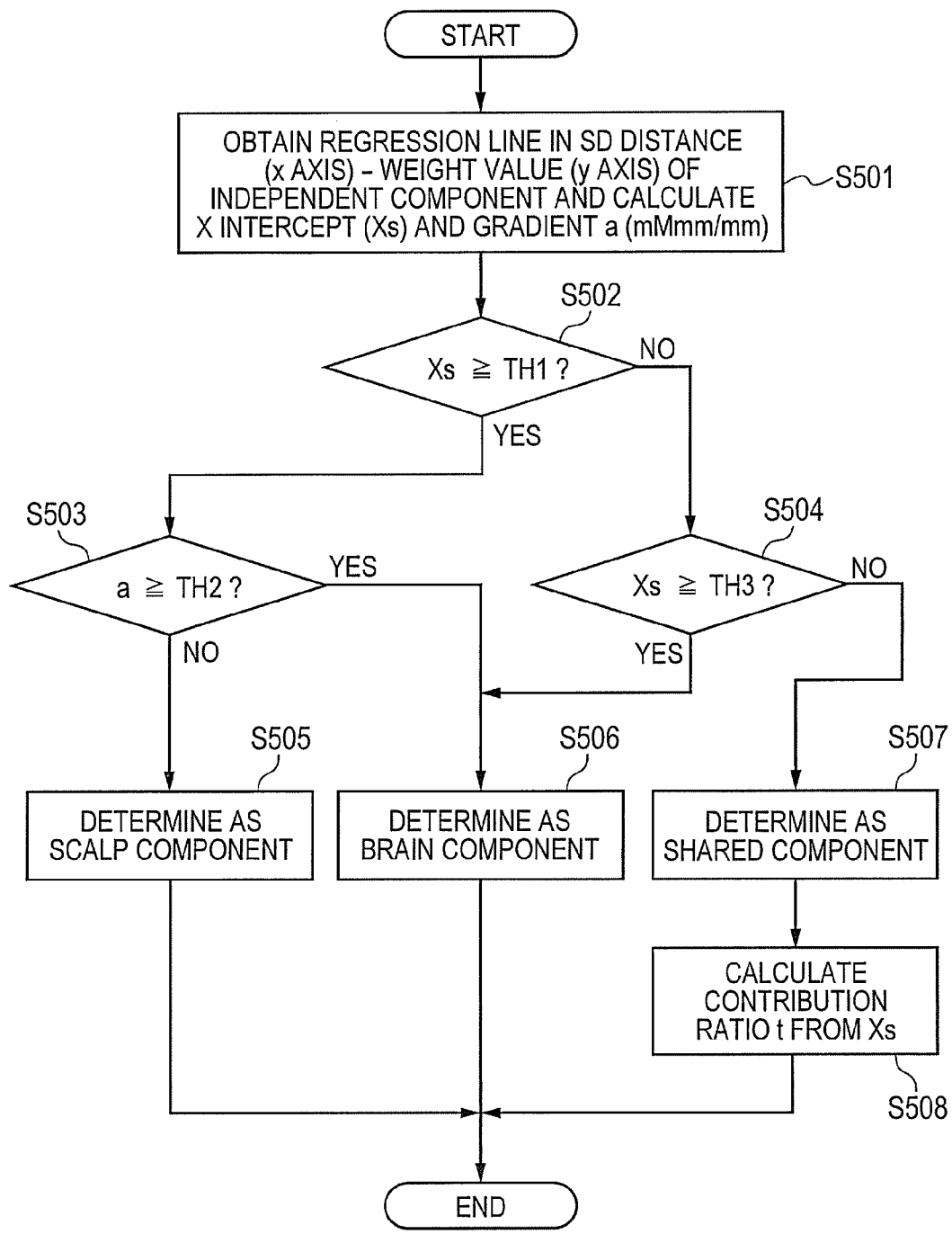
FIG. 37 is a flowchart illustrating a component separating method using an x-intercept of the regression line of an SD distance—component's contribution value distribution of each independent component.

FIG. 37 illustrates a flowchart of an example of a component separating method using an x intercept of the regression line of the SD distance—component's contribution value distribution of each independent component when measurement points in SD distances of 15 mm and 30 mm are used. The calculation part 152 obtains the regression line in the SD-distance (x axis)—weight value (y axis) distribution and calculates the x intercept Xs (mm) and a gradient a (mMmm/mm) for the independent components after performing independent component analysis using a plurality of measurement signals in an SD distance (S501). Next, the calculation part 152 determines whether the x intercept Xs is equal to or larger than the threshold value TH1 (for example, TH1=15 mm) (S502). Since the SD distances are 15 mm and 30 mm, if Xs≥15, a code of the weight value of SD distance of 15 m and 30 mm is different or an absolute value of the weight value of the SD distance of 15 mm is larger than that of the SD distance of 30 mm. Whether the code is different or the absolute value of the weight value of the SD distance of 15 mm is larger than that of the SD distance of 30 mm may be determined by determining whether the gradient a is equal to or larger than the threshold value TH2 (for example, TH2=0.003 mMmm/mm) (S503). If it is determined to be No, it is the latter case and it is considered as the scalp component (S505). Further, if it is determined to be Yes, it is the former case and it is considered as the brain component (S506). In the former case, the codes of the weight values in the SD distances of 15 mm and 30 mm are different but the gradient is large. Therefore, the absolute value of the weight value in the SD distance of 15 mm is smaller than the absolute value of the weight value in the SD distance of 30 mm and thus it is determined as artifact. Further, in step S502, if it is determined to be No, the calculation part 152 determines whether the x intercept Xs is equal to or larger than a threshold value TH3 (for example, TH3=10.83 mm) (S504). If it is determined to be Yes, it is considered as a brain component (S506). If it is determined to be No, it is considered as a shared component which is commonly included in the brain and the scalp (S507). TH3 may be obtained by the Monte Carlo simulation based on the head structure. The calculation part 152 calculates a brain contribution ratio t of shared component using the above Equation 12 (S508). The above calculation is performed for all independent components and then signals for the brain component or the scalp component may be reconstructed.

Here, a method that uses both the x intercept Xs and the gradient a will be described. However, only one of them may be used.

It is desirable to optimize TH1, TH2, and TH3 by the SD distance, the head structure, and the measurement condition to be used. By the analysis by the flow, a plurality of components having different contribution ratios from the brain and the scalp is weighted in accordance with the contribution ratio to be used to reconstruct the signal. Further, it is possible to prevent the erroneous analysis by classifying the components into any one of the brain component and the scalp component and precisely calculate the brain component and the scalp component. Even when the correlation between the signal from the brain and the signal from the scalp is high, it is possible to reconstruct the signal in consideration of the contribution ratio.

According to the embodiment, it is possible to separate the NIRS signal into the signal from the brain and the signal from the scalp, display the result, and precisely perform and analyze the various brain function measurement.

Second Embodiment

Figure 38A:
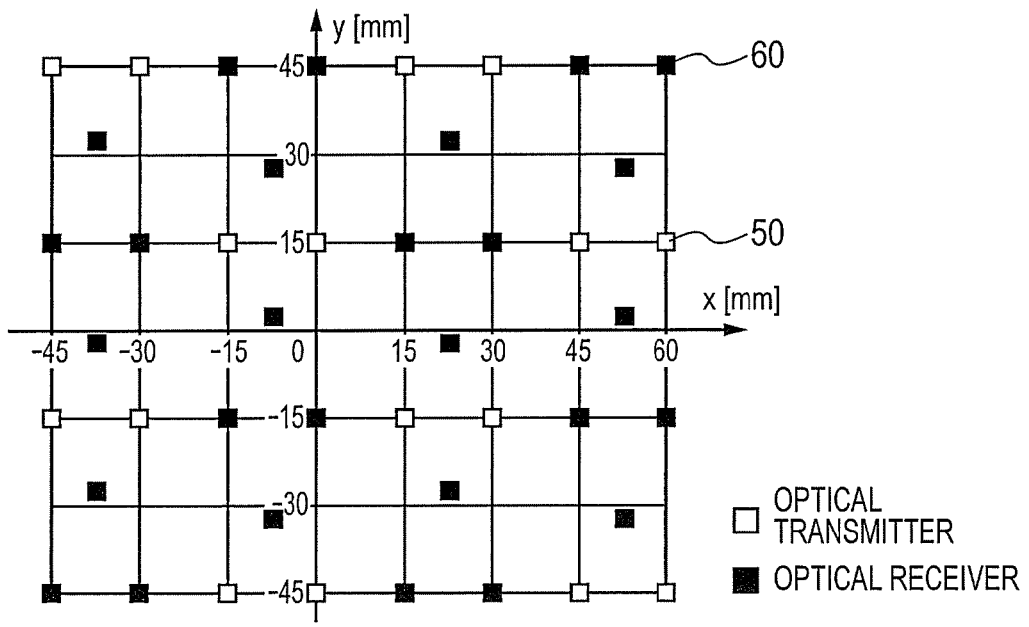
FIG. 38A is a view illustrating a probe arrangement that adds only an optical receiver to the double density probe arrangement.
Figure 38B:
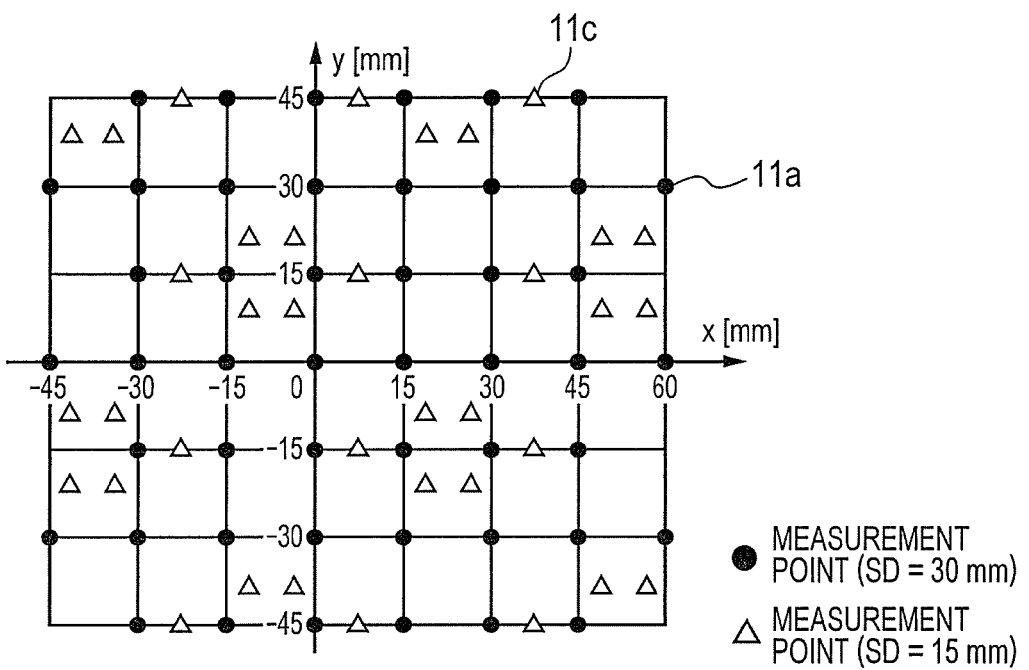
FIG. 38B is a view illustrating arrangement of measurement points of the probe arrangement that adds only an optical receiver to the double density probe arrangement.

In the first embodiment, the distribution density of the measurement points in the SD distance is varied depending on the probe arrangement. By adding only the optical receiver 60 to the probe arrangement described in the first embodiment, it is possible to easily increase the measurement points without lowering the temporal resolution. FIGS. 38A and 38B illustrate the probe arrangement where only the optical receiver 60 is added to the double density probe arrangement (see FIG. 8A) and arrangement of measurement points. The optical receiver is added in a position of the SD distance of 15 mm with respect to the optical transmitters 50. In this case, the measurement point in the SD distance 15 mm is doubled from the number of optical transmitters 50 if the measurement point for the optical transmitter 50 at the border above and below the probe arrangement is removed. The added optical receiver 60 receives light while being synchronized with at least one of the plurality of other optical receivers 60 to increase the measurement points without lowering the temporal resolution of the device and signal to noise ratio of the measurement point. Further, it is possible to further precisely separate the signal from the brain and the signal from the scalp. The added optical receiver 60 may be a detachable optical receiver 60 in accordance with a required precision.

Similarly to the embodiment, if only the optical transmitter 50 is added, in order to prevent the interference with the other measurement point, a processing that shifts the lighting timing or changes a modulation frequency is required. Further, if the neighboring optical receiver 60 is disposed to receive light, the shot noise by the photocurrent is increased in the optical receiver 60 so that the temporal resolution and/or the signal to noise ratio of other measurement points may be lowered. Therefore, a method of the present embodiment that adds only the optical receiver 60 is effective.

The arrangement of the optical receivers 60 illustrated in FIGS. 38A and 38B is illustrative but the invention is not limited to the above arrangement. In the probe arrangement illustrated in FIGS. 15 to 18, the embodiment may be applied by adding the optical receivers 60.

Third Embodiment

Figure 39:
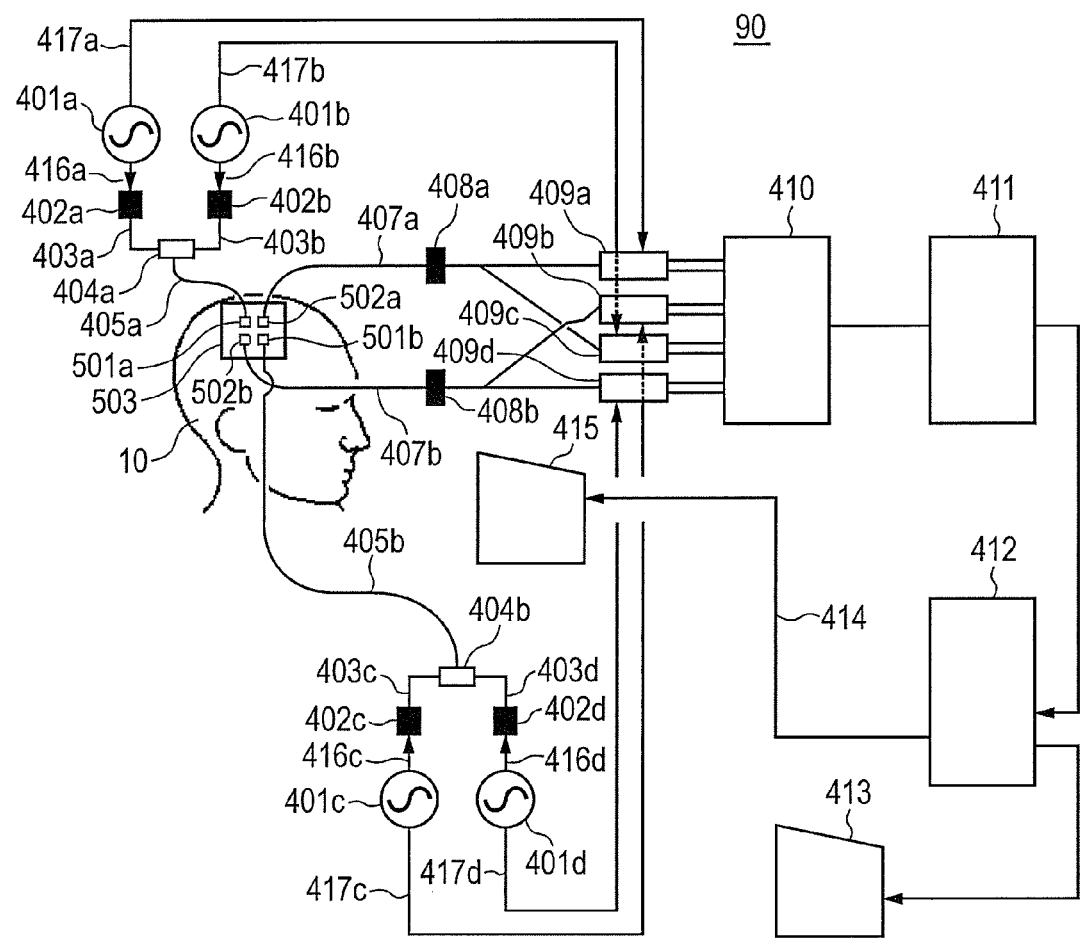
FIG. 39 is a view illustrating an experimental configuration using a whole head measuring type brain function photometric device.

FIG. 39 illustrates an experimental configuration view using a whole head measuring type brain function photometric device 90. A local cerebral blood volume (oxygenated hemoglobin, deoxygenated hemoglobin, and total hemoglobin concentration length change) is obtained in the brain function photometric device 90 by irradiating light having a wavelength which belongs to the visible ray to the infrared region onto the head of the subject and detecting and measuring the light of signals with a plurality of wavelengths which passes through the subject with the same light detector. During the measurement, an appropriate stimulus/instruction may be issued to the subject 10 by a stimulus/instruction presentation device 415. The stimulus/instruction presentation device 415 is controlled by a control signal 414 from the calculator 412.

A plurality of light sources 402a to 402d having different wavelengths (if there are two wavelengths, for example, the wavelength of the light sources 402a and 402c is 695 nm and the wavelength of the light sources 402b and 402d is 830 nm), modulators or oscillators 401a and 401b (401c and 401d) that modulates an intensity of light from the plurality of light sources 402a and 402b (402c and 402d) at different frequencies through driving signal lines 416a and 416b (416c and 416d), a plurality of light irradiating units that irradiates light from a coupler 404a (404b) that couples the light whose intensity is modulated through optical fibers 403a and 403b (403c and 403d) on the scalp of the subject 10 through the transmitting optical fiber 405a (405b), and a plurality of optical receiving units including optical receivers 408a and 408b provided in light receiving optical fibers 407a and 407b such that edges are positioned in a position with a distance (for example, 15 mm and 30 mm) set in advance from the light irradiating position close to the light irradiating position of the plurality of light irradiating units are provided. The light that passes through the living body is focused in the optical fiber by the light receiving optical fibers 407a and 407b and the light that passes through the living body is photoelectrically converted by the optical receivers 408a and 408b to be amplified. Here, at edges of the light transmitting optical fibers 405a and 405b and the light receiving optical fibers 407a and 407b, optical transmitting probes 501a and 501b and optical receiving probes 502a and 502b that support the optical fibers are appropriately disposed in the subject 10. Further, a probe holder 503 that supports the plurality of probes is fixed to the subject 10.

The optical receiving unit detects the light which is reflected and transmitted in the subject 10 and converts the light into an electric signal. Therefore, as the optical receiver 408, a photoelectric conversion element that is representative by a photomultiplier tube or a photodiode may be used. In FIG. 39, it is described that two kinds of wavelength is used. Further, three kinds of wavelength may be also used. Further, for the purpose of the simplicity, in FIG. 39, two light irradiating units and two optical receiving units are disposed. However, in the embodiment, it is required to be a multiple SD arrangement and thus a plurality of receiving units which are not illustrated is present.

Electrical signals that indicate the intensity of living body passed light which is photoelectrically converted by the optical receivers 408a and 408b are input to lock-in amplifiers 409a to 409d. In the lock-in amplifiers 409a to 409d, reference signals 417a to 417d from the oscillators (modulators) 401a and 401b (401c and 401d) are input. For example, in the lock-in amplifiers 409a and 409b, light of 695 nm of the light sources 402a and 402c is separated and output to be drawn by the lock-in processing. In the lock-in amplifiers 409c and 409d, light of 830 nm of the light sources 402b and 402d is separated and output. In this case, in FIG. 39, two points between the optical transmitting probe 501a and optical receiving probe 502a and between the light transmitting probe 501b and the light receiving probe 502b are considered as the measurement points for the purpose of the simplicity. With the similar configuration, two points between the light transmitting probe 501a and the light receiving probe 502b and between the light transmitting probe 501b and the light receiving probe 502a may be the measurement points.

After analog-to-digital converting separated passage light intensity signals having wavelengths which are outputs of the lock-in amplifiers 409a to 409d by the analog-to-digital converter 410, the signals are sent to a measurement and control calculator 411. The measurement and control calculator 411 uses the passage light intensity signal to calculate an oxygenated hemoglobin concentration and a deoxygenated hemoglobin concentration length change, and a total hemoglobin concentration length change from detecting signals of detection points by a method disclosed in Non-Patent Literature 1 and stores the calculated result in a storage device as temporal information in a plurality of measurement points. Here, an example of analog-to-digital conversion performed after performing the lock-in processing is described. However, after amplifying and analog-to-digital converting the signal from the optical receiver, the lock-in processing may be performed in a digital manner. Further, an embodiment that separates a plurality of light components by a modulating method is described, but the invention is not limited thereto. For example, a time divisional method that discriminates the plurality of light components by temporally shifting the timing when the plurality of light components is irradiated may be used.

The calculator 412 includes an input part, an analysis part, a memory part, and an extract part and the result calculated in the measurement and control calculator 411 is analyzed by the analysis part. The input part inputs setting such as analysis condition from the outside. When the calculator 412 has a displaying function, the display 413 may be omitted. The analysis result of the analysis part is stored in the memory part. The extract part extracts information concerning a local brain hemodynamic of the subject 10 from the signal analyzed in the analysis part. The information concerning the local brain hemodynamic of the subject 10 extracted in the extract part is displayed on the display 413. In FIG. 39, the measurement and control calculator 411 and the calculator 412 are separately illustrated. However, only one calculator may be used.

In the configuration, a separating method of the brain component and the scalp component described in the first embodiment may be applied. Using the configuration, at least one of a frontal region, a temporal region, a parietal region, and an occipital region of the head is measured for each of the subjects. If the frontal region is measured, a storage task and an emotional task are performed. If the temporal region is measured, a hearing task, a verbal task, and a motor task are performed. If the parietal region is measured, a motor task and a spatial cognition task are performed. If the occipital region is measured, a visual task and a sleeping task are performed. By performing the measurement in every measurement region and the tasks, it is possible to calculate the distribution of the contribution ratio of the brain component and the scalp component in the measurement region of the subject when the task is performed and thus the measurement may be applied when selecting an optimal task in accordance with the measurement region and the purpose. For example, in a predetermined region, it is possible to select a task that reduces the contribution ratio of the scalp component so as to be smaller as much as possible.

Figure 40:
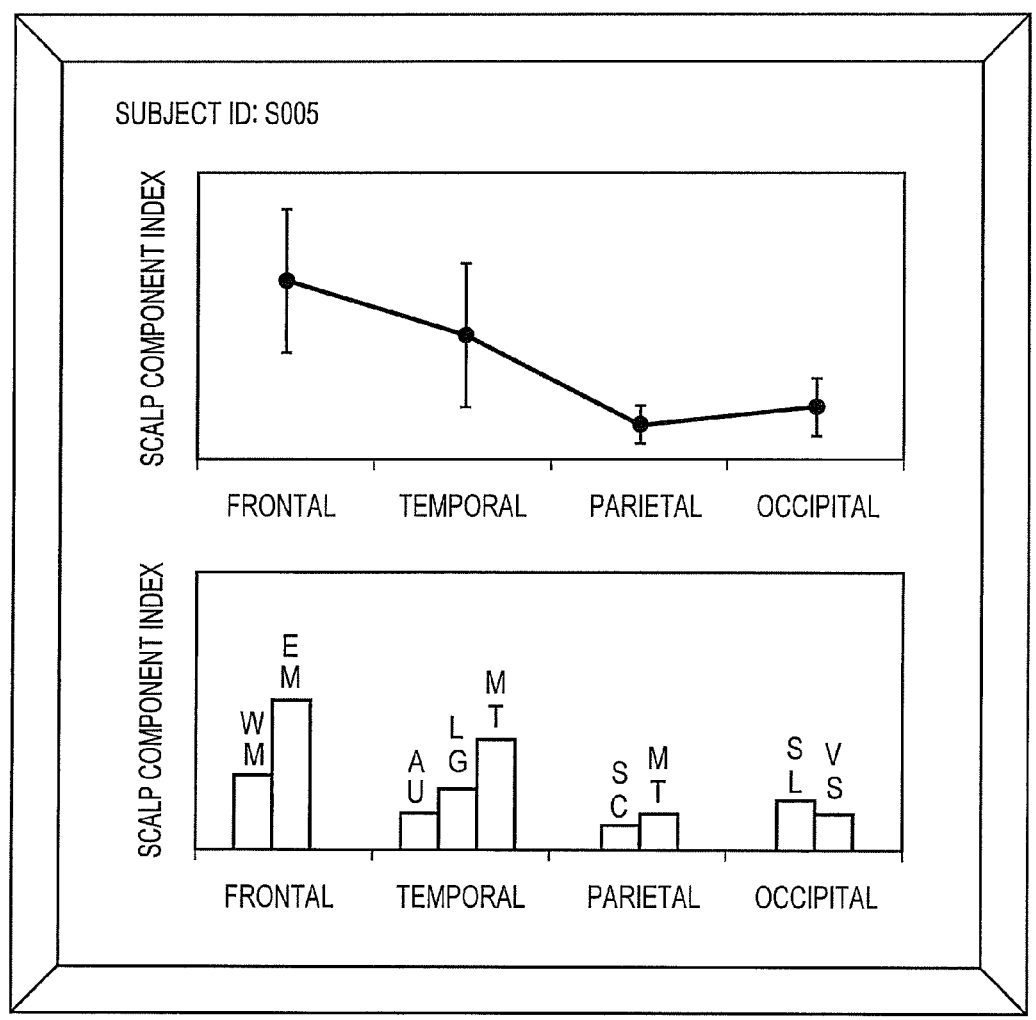
FIG. 40 is an example of a screen that displays task dependency of a brain component and a scalp component in respective regions of a subject.

FIG. 40 illustrates an example of a screen that displays the task dependence of the brain component and the scalp component in each region of the subject. An upper part of FIG. 40 illustrates a scalp component index in the measurement regions with an average value (black circle) and a standard deviation (error bar) and a lower part of FIG. 40 illustrates a scalp component index of the signals by the tasks in each region. A reference symbol WM denotes a working memory task, EM denotes the emotional task, AU denotes audio task, LG denotes a verbal task, MT denotes a motor task, SC denotes a spatial cognition task, SL denotes a sleeping task, and VS denotes the visual task. The scalp component index may use the contribution ratio used together with the brain component and the scalp component or an average amplitude value of the brain component and the scalp component. Here, the brain contribution ratio and the scalp contribution ratio which are used as an index may be represented by Equations 13 and 14.

[Equation 13]

$$\text{BRAIN CONTRIBUTION RATIO} = 100 \times \text{AMPLITUDE VALUE OF BRAIN COMPONENT} / (\text{AMPLITUDE VALUE OF BRAIN COMPONENT} + \text{AMPLITUDE VALUE OF SCALP COMPONENT})(\%) \quad (13)$$

[Equation 14]

$$\text{SCALP CONTRIBUTION RATIO} = 100 \times \text{AMPLITUDE VALUE OF SCALP COMPONENT} / (\text{AMPLITUDE VALUE OF BRAIN COMPONENT} + \text{AMPLITUDE VALUE OF SCALP COMPONENT})(\%) \quad (14)$$

Here, the following relationship of Equation 15 is established.

[Equation 15]

$$\text{BRAIN CONTRIBUTION RATIO} + \text{SCALP CONTRIBUTION RATIO} = 100(\%) \quad (15)$$

The amplitude value of the brain component and the amplitude value of the scalp component in Equations 13 and 14 are defined as a value acquired by obtaining an effective value of the separated independent components by the root mean square (RMS) and calculating a weight value (independent component's contribution value) at the measurement point, and taking the total of the independent component's contribution ratios of the independent components that configure each of the brain component and the scalp component. In FIG. 40, the scalp component index is illustrated, but the brain component index may be illustrated.

By the display method of FIG. 40, it is possible to understand the distribution of the scalp blood flow and the contribution ratios of the signal component from the brain for every region of the subject to be used to select optimal task.

INDUSTRIAL APPLICABILITY

According to the aspects of the invention, in a human head photometric device that uses visible light and near-infrared light, it is possible to separate and extract a brain component and a scalp component from a measurement signal in accordance with the purpose and improve the precision and reproducibility of the human brain function measurement.

REFERENCE SIGNS LIST

10 Subject
11 Measurement point
11a Measurement point (SD=30 mm)
11b Measurement point (SD=23.7 mm)
11c Measurement point (SD=15 mm)
11d Measurement point (SD=10.6 mm)
12 Irradiation point
13 Detection point
20 Main body
30 Light
40 Waveguide
50 Optical transmitter
60 Optical receiver
90 Brain function photometric device
101 Light source
102 Light detector
103 Light source driver
104 Amplifier
105 Analog-to-digital converter
106 Control and analysis part
107 Input part
108 Memory part
109 Display
110 Combo box for probe arrangement selection
111 Radio button for SD distance setting
112 Cell for inputting SD distance
113 OK button
114 Cancel button
121 Text box for inputting kinds of used SD distance
122 Text box for inputting priority SD distance
123 Text box for inputting SD distance
124 Text box for inputting effective radius
131 Radio button for setting light intensity
132 Radio button for setting detector gain
133 Setting button
134 Retry button of gain adjustment
135 Legend
136 Display indicating that detected light intensity is high
137 Display indicating that detected light intensity is moderate
138 Display indicating that detected light intensity is low
139 Automatic gain setting result at measurement point in SD distance of 30 mm
140 Automatic gain setting result at measurement point in SD distance of 15 mm
151 Setting input part
152 Calculation part
153 Subject shape data
154 Measurement point number
155 Light source/detector ID
156 Light source/detector coordinate
157 SD distance
158 Measurement point coordinate
159 Measurement data
160 Measurement part
161 Measurement point information region
162 Extracted independent component
163 Weight value gradient
164 Average of inter-trial correlation coefficient
171 Original data
172 Brain data
173 Scalp data
174 Check box of selecting display method of original data, brain data, and scalp data
301 Oxygenated hemoglobin concentration length change (oxy-Hb) map
302 Grayscale bar
303 Scroll bar of time display
304 Radio button
401 Oscillator (modulator)
402 Light source 403 Optical fiber
404 Coupler
405 Light transmitting optical fiber
407 Light receiving optical fiber
408 Optical receiver (including amplifier)
409 Lock-in amplifier
410 Analog-to-digital (A/D) converter
411 Measurement and control calculator
412 Calculator
413 Display
414 Control signal
415 Stimulus/instruction presentation device
416 Light source driving signal
417 Reference signal from oscillator (modulator)
501 Optical transmitting probe
502 Optical receiving probe
503 Probe holder

The invention claimed is:

1. A biological photometric device, comprising:
one or more light sources, each irradiating light on a subject;
a plurality of light detectors, each detecting the light, which is irradiated on an irradiation point on the subject from one of the light sources and propagated in the subject, at a detection point on the subject; and
a calculator that analyzes signals obtained by the light detectors,
wherein each of the light sources and each of the light detectors are configured to be disposed on the subject such that SD distance defined on the subject as a distance between the irradiation point and the detection point, is spaced as at least two types of spacing, and
the calculator extracts a plurality of separated components including a deep portion component reflecting signal from brain of the subject and a shallow portion component reflecting signal from scalp of the subject using a signal separation method from a plurality of measurement data respectively measured by combinations of the light source and the light detector having different values of the SD distances from one another, analyzes a first dependency of weight of the deep portion component within the measurement data with respect to the SD distance or a partial optical path length in gray matter and a second dependency of weight of the shallow portion component within measurement data with respect to the SD distance or the partial optical path length in gray matter by performing regression analysis and reconstructs the deep portion component and the shallow portion component of the measurement data according to the first dependency of weight of the deep portion component and the second dependency of weight of the shallow portion component.

2. The biological photometric device according to claim 1, wherein the calculator uses the parameter to calculate a contribution ratio of a deep portion and a shallow portion in a shared component that contains both of the signal from brain of the subject and signal from scalp of the subject and uses a weight which is proportional to the contribution ratio to reconstruct the deep portion component and the shallow portion component.

3. The biological photometric device according to claim 1, wherein the plurality of light detectors is disposed so as to detect a signal from at least two light sources having different SD distances among signals from the plurality of light sources which is configured to be disposed within a radius of 60 mm from the light detector on the subject.

4. The biological photometric device according to claim 1, wherein the one or plurality of light detectors detects a signal from at least two kinds of the plurality of light sources at different timing.

5. The biological photometric device according to claim 1, wherein the one or plurality of light detectors is disposed so as to detect the light that is irradiated from the one or plurality of light sources and propagated in a gray matter of the subject.

6. The biological photometric device according to claim 1, wherein the first and second dependencies are expressed as a function $g(w, u, \sigma) = w \times (u^2 + \sigma^2)^{0.5}$ or a function $g(w) = w$ (w is a weight value, u is a mean amplitude value of the separated component, and $\sigma$ is a standard deviation of an amplitude value of the separated component).

7. The biological photometric device according to claim 1, comprising:
a controller that controls the one or plurality of light sources and the one or plurality of light detectors:
wherein the controller controls a power of the light irradiated from the light sources depending on the SD distance or a power of the light detected by the light detectors.

8. The biological photometric device according to claim 1, comprising:
a controller that controls the one or plurality of light sources and the one or plurality of light detectors:
wherein the controller switches use or nonuse of respective ones of the light sources or the light detecting units detectors in accordance with time.

9. The biological photometric device according to claim 1, comprising:
a display that displays an analysis result in the calculator;
wherein the display displays the separated components so as to divide the separated components into a shallow portion signal, a deep portion signal, a signal which is commonly included in the shallow portion and the deep portion, or divide signals in a plurality of SD distances, or divide signals in a measurement portion including at least one of a frontal region, a temporal region, a parietal region, and an occipital region of head of the subject, or divide the separated components into a response signal of a task including at least one of a memory task, a motor task, a verbal task, and a visual task.

10. The biological photometric device according to claim 1, further comprising:
a support that supports the light sources and the light detectors;
wherein the support additionally or detachably supports an auxiliary light detector in order to increase measurement points, and
the auxiliary light detector detects the light at a timing when the auxiliary light detector is synchronized with at least one of the plurality of light detectors.

11. The biological photometric device according to claim 1, further comprising:
a controller that controls the one or plurality of light sources and the one or plurality of light detectors;
an input part that manually inputs a control method in the controller and an analysis method in the calculator.

12. The biological photometric device according to claim 1, wherein the plurality of light sources and the plurality of light detectors are disposed such that the SD distance in at least two measurement points is larger than approximately 10 mm and in this case, approximately 10 mm is 7 mm or larger and smaller than 13 mm.

13. The biological photometric device according to claim 1, wherein a component including at least one of a biological signal in a shallow portion of the subject, a biological signal in a deep portion, a systemic biological signal, a device noise, and a noise due to a body motion, is separated and extracted.

14. The biological photometric device according to claim 1, wherein the calculator analyzes the first dependency by deriving model parameters of a first regression curve through fitting the first regression curve to function values of weight of the deep portion component within the measurement data corresponding to various values of the SD distance, and analyzes the second dependency by deriving model parameters of a second regression curve through fitting the second regression curve to function values of weight of the shallow portion component within the measurement data corresponding to various values of the SD distance.

15. The biological photometric device according to claim 14, wherein the calculator reconstructs the deep portion component and the shallow portion component of the measurement data by determining a threshold value of gradient from the first gradient and the second gradient and by segregating respective ones of the separated components into deep portion components and shallow portion components based on the determined threshold value of gradient.

16. The biological photometric device according to claim 1, wherein the calculator analyzes the first dependency by deriving a first gradient of a first regression line through fitting the first regression line to function values of weight of the deep portion component within the measurement data corresponding to various values of the SD distance, and analyzes the second dependency by deriving a second gradient of a second regression line through fitting the second regression line to function values of weight of the shallow portion component within the measurement data corresponding to various values of the SD distance.

17. A biological photometric method that uses a biological photometric device including:
one or more light sources that irradiates light on a subject;
a plurality of light detectors that detects the light, which is irradiated on an irradiation point on the subject from the one or more light sources and propagated in the subject, at a detection point on the subject; and a calculator that analyzes a signal obtained by the one or plurality of light detectors, the method comprising:
disposing each of the light sources and each of the light detectors on the subject such that SD distance defined on the subject as a distance between the irradiation point and the detection point, is spaced as at least two types of spacing;
extracting a plurality of separated components including a deep portion component reflecting signal from brain of the subject and a shallow portion component reflecting signal from scalp of the subject using a signal separation method from a plurality of measurement data respectively measured by combinations of the light source and the light detector having different values of the SD distance from on another;
analyzing a first dependency of weight of the deep portion component within the measurement data with respect to the SD distance or a partial optical path length in gray matter and a second dependency of weight of the shallow portion component within measurement data with respect to the SD distance or the partial optical path length in gray matter by performing regression analysis; and
reconstructing the deep portion component and the shallow portion component of the measurement data according to the first dependency of weight of the deep portion component and the second dependency of weight of the shallow portion component.

* * * * *